United States Patent
Lange et al.

(10) Patent No.: US 11,878,967 B2
(45) Date of Patent: Jan. 23, 2024

(54) CRYSTALLINE FORMS OF 1-(4-{[6-AMINO-5-(4-PHENOXY-PHENYL)-PYRIMIDIN-4-YLAMINO]-METHYL}-4-FLUORO-PIPERIDIN-1-YL)-PROPENONE, SALT FORMS THEREOF, AND PROCESSES TO OBTAIN

(71) Applicant: Merck Patent GmbH, Darmstadt (DE)

(72) Inventors: Michael Lange, Darmstadt (DE); Clemens Kuehn, Darmstadt (DE); Tobias Schlueter, Riestadt (DE); Werner Mederski, Zwingenberg (DE); David Maillard, Darmstadt (DE); Edoardo Burini, Guidonia Montecelio (IT)

(73) Assignee: Merck Patent GmbH, Darmstadt (DE)

( * ) Notice: Subject to any disclaimer, the term of this patent is extended or adjusted under 35 U.S.C. 154(b) by 179 days.

(21) Appl. No.: 17/252,804

(22) PCT Filed: Jun. 17, 2019

(86) PCT No.: PCT/EP2019/065815
§ 371 (c)(1),
(2) Date: Dec. 16, 2020

(87) PCT Pub. No.: WO2019/243223
PCT Pub. Date: Dec. 26, 2019

(65) Prior Publication Data
US 2021/0261525 A1 Aug. 26, 2021

Related U.S. Application Data

(60) Provisional application No. 62/686,797, filed on Jun. 19, 2018.

(51) Int. Cl.
| | | |
|---|---|---|
| *C07D 401/12* | (2006.01) | |
| *A61P 35/00* | (2006.01) | |
| *A61P 37/00* | (2006.01) | |
| *A61K 31/506* | (2006.01) | |

(52) U.S. Cl.
CPC ........ *C07D 401/12* (2013.01); *C07B 2200/13* (2013.01)

(58) Field of Classification Search
CPC ... C07D 401/12; C07B 2200/13; A61P 35/00; A61P 37/00; A61K 31/506
See application file for complete search history.

(56) References Cited

U.S. PATENT DOCUMENTS

| | | |
|---|---|---|
| 9,751,889 B2 | 9/2017 | Chen et al. |
| 9,828,383 B1 | 11/2017 | Purro et al. |
| 2017/0119766 A1 | 5/2017 | Huck et al. |
| 2017/0136018 A1* | 5/2017 | Dellovade ............. A61K 45/06 |
| 2018/0051026 A1 | 2/2018 | Peddy et al. |
| 2020/0206224 A1 | 7/2020 | Huck et al. |

FOREIGN PATENT DOCUMENTS

| | | |
|---|---|---|
| JP | 2015-518885 | 7/2015 |
| JP | 2016-538314 T2 | 12/2016 |
| JP | 2018-511580 | 4/2018 |
| WO | 2012/170976 | 12/2012 |
| WO | 2017/087445 | 5/2017 |
| WO | 2018/154131 | 8/2018 |

OTHER PUBLICATIONS

Stieger, N., "Recrystallization of active pharmaceutical ingredients." Crystallization-Science and Technology [Internet]. InTech (2012): 183-204.*
U.S. Appl. No. 16/809,850, filed Mar. 5, 2020, 2020/0206224, Huck et al.
International Search Report dated Aug. 7, 2019 in PCT/EP2019/065815.
Written Opinion dated Aug. 7, 2019 in PCT/EP2019/065815.
Bastin et al., "Salt Selection and Optimisation Procedures for Pharmaceutical New Chemical Entities", Organic Process Research & Development, vol. 4, No. 5, 2000, pp. 427-435.
Mino R. Caira, "Crystalline Polymorphism of Organic Compounds", Topics in Current Chemistry, vol. 198, 1998, pp. 163-208.
Morissette et al., "High-throughput crystallization: polymorphs, salts, co-crystals and solvates of pharmaceutical solids", Advanced Drug Delivery Reviews, vol. 56, 2004, pp. 275-300.
Abu T.M. Serajuddin, "Salt formation to improve drug solubility", Advanced Drug Delivery Reviews, vol. 59, 2007, pp. 603-616.
Variankaval et al., "From Form to Function: Crystallization of Active Pharmaceutical Ingredients", AIChE Journal, vol. 54, No. 7, Jul. 2008, pp. 1682-1688.

* cited by examiner

*Primary Examiner* — John M Mauro
(74) *Attorney, Agent, or Firm* — Grüneberg and Myers PLLC

(57) ABSTRACT

A solid form of 1-(4-{[6-Amino-5-(4-phenoxy-phenyl)-pyrimidin-4-ylamino]-methy}-4-fluoro-piperidin-1-yl)-propenone, or pharmaceutically acceptable salts thereof, is useful as a BTK inhibitor.

23 Claims, 29 Drawing Sheets

CRYSTALLINE FORMS OF 1-(4-{[6-AMINO-5-(4-PHENOXY-PHENYL)-PYRIMIDIN-4-YLAMINO]-METHYL}-4-FLUORO-PIPERIDIN-1-YL)-PROPENONE, SALT FORMS THEREOF, AND PROCESSES TO OBTAIN

CROSS-REFERENCE TO RELATED APPLICATIONS

This application is the National Stage entry under § 371 of International Application No. PCT/EP2019/065815, filed on Jun. 17, 2019, and which claims the benefit of U.S. Application No. 62/686,797, filed on Jun. 19, 2018. The content of each of these applications is hereby incorporated by reference in its entirety.

BACKGROUND OF THE INVENTION

Field of the Invention

The present invention relates to solid forms of 1-(4-{[6-Amino-5-(4-phenoxy-phenyl)-pyrimidin-4-ylamino]-methyl}-4-fluoro-piperidin-1-yl)-propenone (Compound 1) in substantially crystalline form or amorphous form, pharmaceutical compositions thereof, and methods of treatment therewith. The present invention relates to HCl, HBr, oxalate, maleate, fumarate, and mesylate salts of (Compound 1), as well as solid forms of said salts, in substantially crystalline form, pharmaceutical compositions thereof, and methods of treatment therewith.

Description of Related Art

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes. Also, BTK has been reported to play a role in apoptosis (Islam and Smith Immunol. Rev. 2000 178:49,) and thus BTK inhibitors would be useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc-gamma signaling in myeloid cells. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors.

SUMMARY OF THE INVENTION

It has now been found that solid forms of 1-(4-{[6-Amino-5-(4-phenoxy-phenyl)-pyrimidin-4-ylamino]-methyl}-4-fluoro-piperidin-1-yl)-propenone (Compound 1), and pharmaceutically acceptable compositions thereof, are effective as inhibitors of BTK.

In one aspect, Compound 1 is in a substantially crystalline and salt free form referred to as Form A2 as described and characterized herein. In one aspect, Compound 1 is in a substantially crystalline and salt free form referred to as Form A1 as described and characterized herein. In one aspect, Compound 1 is in a substantially crystalline and salt free form referred to as Form HCl-NF1 as described and characterized herein. In one aspect, Compound 1 is in a substantially crystalline and salt free form referred to as Form HCl-NF2 as described and characterized herein. In one aspect, Compound 1 is in a substantially crystalline and salt free form referred to as Form HCl-NF3 as described and characterized herein. In one aspect, Compound 1 is in a substantially crystalline and salt free form referred to as Form HBr-NF1 as described and characterized herein. In one aspect, Compound 1 is in a substantially crystalline and salt free form referred to as Form HBr-NF2 as described and characterized herein. In certain aspects, Compound 1 is Oxalate salt form Oxalate-NF1. In certain aspects, Compound 1 is Maleate salt form Maleate-NFL In certain aspects, Compound 1 is Maleate salt form Maleate-NF2. In certain aspects, Compound 1 is Fumarate salt form Fumarate-NF1. In certain aspects, Compound 1 is Fumarate salt form Fumarate-NF2. In certain aspects, Compound 1 is Fumarate salt form Fumarate-NF3. In certain aspects, Compound 1 is Fumarate salt form Fumarate-NF4. In certain aspects, Compound 1 is Fumarate salt form Fumarate-NF5. In certain aspects, Compound 1 is Mesylate salt form Mesylate-NF1.

The properties of a solid relevant to its efficacy as a drug can be dependent on the form of the solid. For example, in a drug substance, variation in the solid form can lead to differences in properties such as melting point, dissolution rate, oral absorption, bioavailability, toxicology results and clinical trial results.

Certain advantages of the following solid forms include the following.

A1: crystalline morphic form with very good crystallinity; high thermal stability (mp~160° C.); slightly hygroscopic according to Ph. Eur. (section 5.11).

A2: crystalline morphic form with very good crystallinity; high thermal stability (mp~168° C.); slightly hygroscopic according to Ph. Eur. (section 5.11).

Hydrochloride salt form HCl-NF1: crystalline morphic form with very good crystallinity; high thermal stability (mp/dec~200° C.); slightly hygroscopic according to Ph. Eur. (section 5.11); 1:1 salt stoichiometry; higher dissolution levels (2 h) compared to crystalline neat form A1 in biorelevant intestinal media; FaSSIF approximately factor 4 higher than A1.

Hydrochloride salt form HCl-NF2: crystalline morphic form; high thermal stability (mp/dec~192° C.); 1:1 salt stoichiometry.

Hydrochloride salt form HCl-NF3: crystalline morphic form with very good crystallinity; high thermal stability (mp/dec~200° C.); 1:1 salt stoichiometry.

Hydrobromide salt form HBr-NF1: crystalline morphic form with very good crystallinity; high thermal stability (mp/dec~203° C.); slightly hygroscopic according to Ph. Eur. (section 5.11); 1:1 salt stoichiometry; higher dissolution levels (2 h) compared to crystalline neat form A1 in biorelevant intestinal media; FaSSIF approximately factor 3 higher than A1.

Hydrobromide salt form HBr-NF2: crystalline morphic form; high thermal stability (mp/dec~173° C.); slightly hygroscopic according to Ph. Eur. (section 5.11); 1:1 salt stoichiometry.

Oxalate salt form NF1: crystalline morphic form with very good crystallinity; high thermal stability (mp/dec~173° C.); slightly hygroscopic according to Ph. Eur. (section 5.11); 1:0.5 salt stoichiometry; higher dissolution levels (2 h) compared to crystalline neat form A1 in biorelevant intestinal media; FaSSIF approximately factor 4 higher than A1.

Maleate salt form NF1: crystalline morphic form with very good crystallinity; high thermal stability (mp/dec~139° C.); slightly hygroscopic according to Ph. Eur. (section 5.11); 1:1 salt stoichiometry.

Maleate salt form NF2: crystalline morphic form with very good crystallinity; 1:1 salt stoichiometry.

Fumarate salt form NF1: crystalline morphic form; high thermal stability (mp/dec 173° C.); slightly hygroscopic according to Ph. Eur. (section 5.11); 1:1 salt stoichiometry; higher dissolution levels (2 h) compared to crystalline neat form A1 in biorelevant intestinal media; FaSSIF approximately factor 2 higher than A1.

Fumarate salt form NF2: crystalline morphic form with good crystallinity; thermal stability (phase transition~90° C.; transition to NF-1); 1:1 salt stoichiometry.

Fumarate salt form NF3: crystalline morphic form with very good crystallinity; thermal stability (phase transition~70° C.; transition to NF-1); 1:1 salt stoichiometry.

Fumarate salt form NF4: crystalline morphic form with good crystallinity; high thermal stability (mp/dec~140° C.).

Fumarate salt form NF5: crystalline morphic form; high thermal stability (mp/dec 158° C.); 1:1 salt stoichiometry.

Mesylate salt form NF1: crystalline morphic form with good crystallinity; high thermal stability (mp/dec~196° C.); slightly hygroscopic according to Ph. Eur. (section 5.11); 1:1 salt stoichiometry.

Solid forms of Compound 1, and pharmaceutically acceptable compositions thereof, are useful for treating a variety of diseases, disorders or conditions, associated with BTK. Such diseases, disorders, or conditions include those described herein.

DETAILED DESCRIPTION OF THE INVENTION

Figure 1:
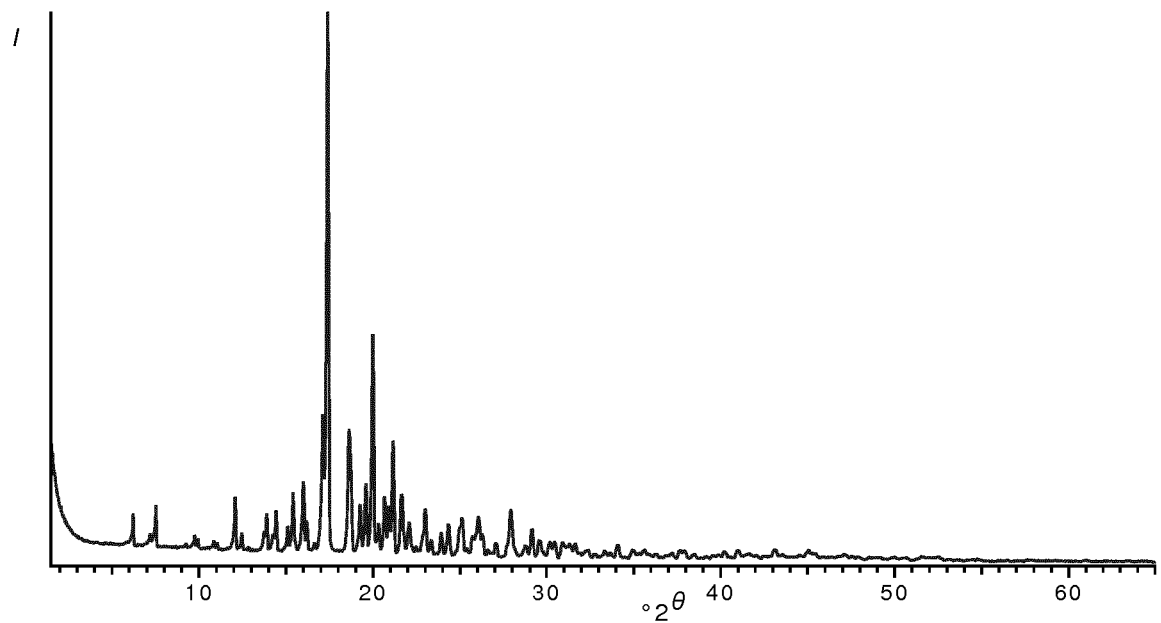
FIG. 1: Powder X-ray diffractogram of Form A1.
Figure 2:
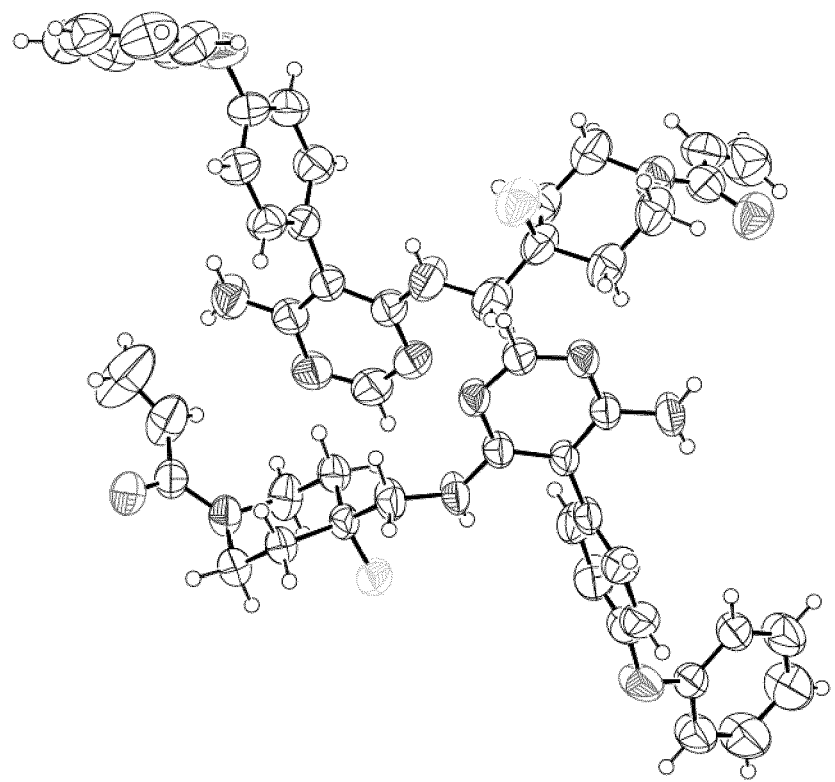
FIG. 2: Single Crystal Structure of Free Base Form A1 Viewed Approximately Along A-Axis.
Figure 3:
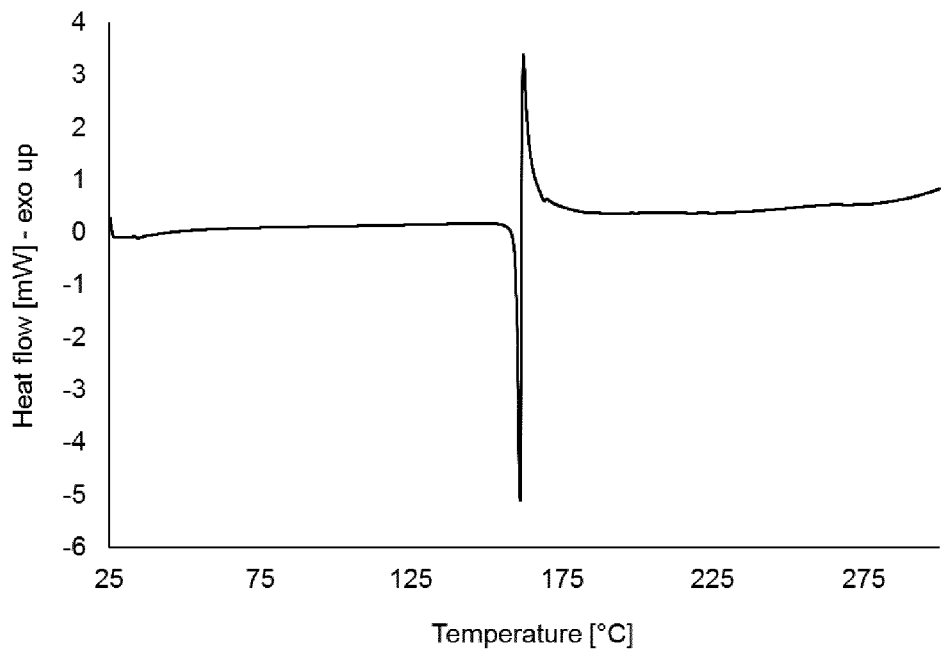
FIG. 3: DSC scan of free base form A1 (5 K/min).
Figure 4:
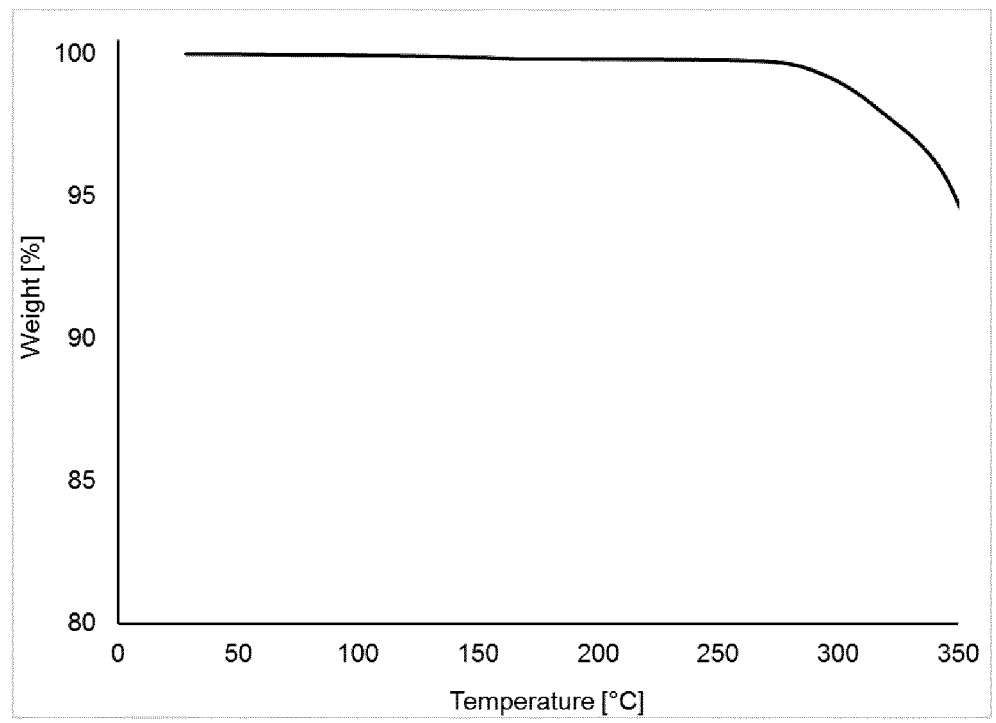
FIG. 4: TGA scan of free base form A1 (5 K/min).
Figure 5:
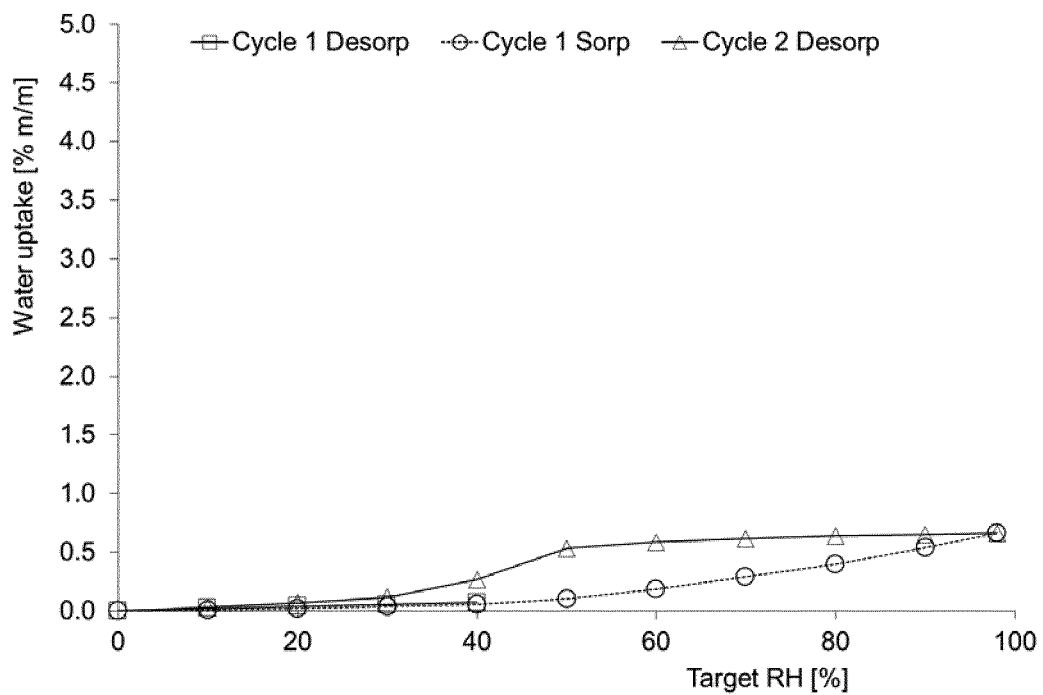
FIG. 5: Water Vapour Sorption Isotherm (25° C.) of free base form A1.

1. General Description of Compounds of the Invention

In certain aspects, the present invention provides for inhibitors of BTK. In some embodiments, such compounds include those of the formulae described herein, or a pharmaceutically acceptable salt thereof, wherein each variable is as defined and described herein.

2. Compounds and Definitions

As used herein the term "amorphous" refers to solid forms that consist of disordered arrangements of molecules and do not possess a distinguishable crystal lattice.

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

The term "chemically stable", as used herein, means that the solid form of Compound 1 does not decompose into one or more different chemical compounds when subjected to specified conditions, e.g., 40° C./75% relative humidity, for a specific period of time. e.g. 1 day, 2 days, 3 days, 1 week, 2 weeks, or longer. In some embodiments, less than 25% of the solid form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the solid form of Compound 1 decomposes.

The term "physically stable", as used herein, means that the solid form of Compound 1 does not change into one or more different physical forms of Compound 1 (e.g. different solid forms as measured by XRPD, DSC, etc.) when subjected to specific conditions, e.g., 40° C./75% relative humidity, for a specific period of time. e.g. 1 day, 2 days, 3 days, 1 week, 2 weeks, or longer. In some embodiments, less than 25% of the solid form of Compound 1 changes into one or more different physical forms when subjected to specified conditions. In some embodiments, less than about 20%, less than about 15%, less than about 10%, less than about 5%, less than about 3%, less than about 1%, less than about 0.5% of the solid form of Compound 1 changes into one or more different physical forms of Compound 1 when subjected to specified conditions. In some embodiments, no detectable amount of the solid form of Compound 1 changes into one or more physically different solid forms of Compound 1.

As used herein, the phrase "substantially amorphous Compound 1" is used interchangeably with the phrases "amorphous Compound 1," "amorphous Compound 1 substantially free of crystalline Compound 1," and "substantially amorphous 1-(4-{[6-Amino (4-phenoxy-phenyl)-pyrimidin-4-ylamino]-methyl}-4-fluoro-piperidin-1-yl)-propenone." In some embodiments, substantially amorphous Compound 1 has less than about 30% crystalline Compound 1, for example, less than about 30% of crystalline Compound 1, e.g., less than about 25% crystalline Compound 1, less than about 20% crystalline Compound 1, less than about 15% crystalline Compound 1, less than about 10% crystalline Compound 1, less than about 5% crystalline Compound 1, less than about 2% crystalline Compound 1.

As used herein, the phrase "substantially crystalline Compound 1" is used interchangeably with the phrases "Compound 1," and "crystalline Compound 1 substantially free of amorphous Compound 1." In some embodiments, substantially crystalline Compound 1 has less than about 30% amorphous Compound 1 or other solid forms, for example, less than about 30% of amorphous Compound 1 or other solid forms, e.g., less than about 25% amorphous Compound 1 or other solid forms, less than about 20% amorphous Compound 1 or other solid forms, less than about 15% amorphous Compound 1 or other solid forms, less than about 10% amorphous Compound 1 or other solid forms, less than about 5% amorphous Compound 1 or other solid forms, less than about 2% amorphous Compound 1 or other solid forms. In some embodiments, substantially crystalline Compound 1 has less than about 1% amorphous Compound 1 or other solid forms.

The term "substantially free" (as in the phrase "substantially free of form X") when referring to a designated solid form of Compound 1 (e.g., an amorphous or crystalline form described herein) means that there is less than 20% (by weight) of the designated form(s) or co-form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated form(s) present.

The term "substantially pure" when referring to a designated solid form of Compound 1 (e.g., an amorphous or crystalline solid form described herein) means that the designated solid form contains less than 20% (by weight) of residual components such as alternate polymorphic or isomorphic crystalline form(s) or co-form(s) of Compound 1. It is preferred that a substantially pure solid form of Compound 1 contains less than 10% (by weight) of alternate polymorphic or isomorphic crystalline forms of Compound 1, more preferably less than 5% (by weight) of alternate polymorphic or isomorphic crystalline forms of Compound 1, and most preferably less than 1% (by weight) of alternate polymorphic or isomorphic crystalline forms of Compound 1.

As used herein, a "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase), or alternatively, an amorphous drug (dispersed phase) in an amorphous polymer (continuous phase). In some embodiments an amorphous solid dispersion includes the polymer constituting the dispersed phase, and the drug constitutes the continuous phase. In some embodiments, the dispersion includes amorphous Compound 1 or substantially amorphous Compound 1.

The term "solid amorphous dispersion" generally refers to a solid dispersion of two or more components, usually a drug and polymer, but possibly containing other components such as surfactants or other pharmaceutical excipients, where Compound 1 is amorphous or substantially amorphous (e.g., substantially free of crystalline Compound 1), and the physical stability and/or dissolution and/or solubility of the amorphous drug is enhanced by the other components.

As used herein, the terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

The abbreviation "XRPD" stands for X-ray powder diffraction. The term XRPD is used interchangeably with PXRD.

The abbreviation "DSC" stands for differential scanning calorimetry.

The abbreviation "TGA" stands for thermogravimetric analysis.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydro iodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

3. Description of Exemplary Compounds

According to one aspect, the present invention provides a solid form of compound 1,

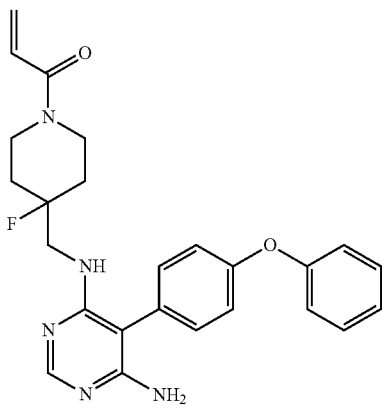

1 or a pharmaceutically acceptable salt thereof.

In certain aspects, the invention provides solid form A2 of Compound 1, solid form A1 of Compound 1, HCl salt HCl-NF1 of Compound 1, HCl salt HCl-NF2 of Compound 1, HCl salt HCl-NF3 of Compound 1, HBr salt HBr-NF1 of Compound 1, HBr salt HBr-NF2 of Compound 1, Oxalate salt form Oxalate-NF1 of Compound 1, Maleate salt form Maleate-NF1 of Compound 1, Maleate salt form Maleate-NF2 of Compound 1, Fumarate salt form Fumarate-NF1 of Compound 1, Fumarate salt form Fumarate-NF2 of Compound 1, Fumarate salt form Fumarate-NF3 of Compound 1, Fumarate salt form Fumarate-NF4 of Compound 1, Fumarate salt form Fumarate-NF5 of Compound 1, or Mesylate salt form Mesylate-NF1 of Compound 1.

In one embodiment, the invention provides Compound 1 characterized as crystalline form A1.

In certain embodiments, form A1 is characterized by one or more 2θ peaks at 17.4 and 20.0 degrees. In certain embodiments, form A1 is characterized by one or more 2θ peaks at 17.1, 17.4, 18.8, 20.0, and 21.1, degrees. In certain embodiments, form A1 is characterized by two or more 2θ peaks at 17.1, 17.4, 18.8, 20.0, and 21.1, degrees. In certain embodiments, form A1 is characterized by three or more 2θ peaks at 17.1, 17.4, 18.8, 20.0, and 21.1, degrees. In certain embodiments, form A1 is characterized by four or more 2θ peaks at 17.1, 17.4, 18.8, 20.0, and 21.1, degrees. In certain embodiments, form A2 is characterized by 2θ peaks at 17.1, 17.4, 18.8, 20.0, and 21.1, degrees.

In certain embodiments, form A1 is characterized by 2θ peaks at

| No. | °2θ (Cu-K$\alpha_1$ radiation) ± 0.2° |
|---|---|
| 1 | 6.2 |
| 2 | 7.5 |
| 3 | 12.1 |
| 4 | 12.5 |
| 5 | 13.9 |
| 6 | 14.5 |
| 7 | 15.4 |
| 8 | 16.0 |
| 9 | 16.2 |
| 10 | 17.1 |
| 11 | 17.4 |
| 12 | 18.6 |
| 13 | 18.8 |
| 14 | 19.3 |
| 15 | 19.6 |
| 16 | 20.0 |
| 17 | 20.7 |
| 18 | 21.1 |
| 19 | 21.7 |
| 20 | 23.0 |
| 21 | 25.1 |

In another embodiment, form A1 is characterized by a diffraction pattern substantially similar to that of FIG. 1.

A Powder X-Ray Diffraction pattern of free base form A1 was obtained by standard techniques as described in the European Pharmacopeia 6$^{th}$ Edition chapter 2.9.33, and was characterised by the following X-ray powder diffractogram (monochromatic Cu-K$\alpha_1$ radiation, λ=1.5406 Å, Stoe StadiP 611 KL transmission diffractometer).

In certain embodiments, form A1 is characterized by a crystal form, having a monoclinic space group P21/n with the lattice parameters (at 298 K) a=12.8483(4) Å, b=12.8585 (3) Å, c=28.5734(9) Å, and β=97.950(3)° (with α=γ=90°). Reasonably rounded, the parameters are a=12.8±0.1 Å, b=12.9±0.1 Å, c=28.6±0.1 Å, and β=98.0±0.1° (with α=γ=90°). From the single crystal structure it is clear that form A1 represents an anhydrous form. Single crystal X-Ray Structure data were obtained on free base form A1 as well (SuperNova diffractometer from Agilent, equipped with CCD Detector using Cu K$_\alpha$ radiation at 298 K).

In certain embodiments, form A1 is an anhydrous form.

Other physical properties of form A1 include the following: Thermal behaviour of form A1 showed a melting peak onset at approx. 160° C. Thermogravimetric analysis revealed a low weight loss of approx. 0.2% m/m up to this temperature. DSC and TGA profiles are displayed below. DSC scan of form A1 was acquired on a Mettler-Toledo DSC 1 with a heating rate of 5 K/min, using nitrogen purge gas at 50 mL/min. TGA scan of form A1 was acquired on a Mettler-Toledo TGA 851 with a heating rate of 5 K/min, using nitrogen purge gas at 50 mL/min. Water Vapour Sorption behaviour of form A1 revealed small water uptake levels ≤1% m/m in the relative humidity (rh) range 0-80% rh, and very slightly elevated water uptake levels ≤2% m/m in the relative humidity (rh) range 90-98% rh. Form A1 can be classified as slightly hygroscopic acc. to Ph. Eur. Criteria (section 5.11.). Water Vapor Sorption isotherm (25° C.) of form A1 is provided in the figures. Water Vapour Sorption isotherm was acquired on a DVS-Intrinsic system from SMS. Thermodynamic solubility (24 h) of form A1 at 37° C. was determined to be approx. 17 µg/mL in Fasted-State Simulated Intestinal Fluid [FaSSIF, pH 6.5], and approx. 1 µg/mL in USP Phosphate buffer [pH 7.4], respectively (see example 6). Dissolution level of form A1 in Fasted-State Simulated Intestinal Fluid [FaSSIF, pH 6.5] at 37° C. was determined to be approx. 17 µg/mL after 2 h (see example 7). Overall, free base form A1 revealed good solid-state properties (good crystallinity, slightly hygroscopic, high thermal stability) with good manufacturability in larger scale.

In one embodiment, the invention provides for Compound 1 characterized as crystalline form A2.

In certain embodiments, form A2 is characterized by one or more 2θ peaks at 17.0, 18.7, and 21.7 degrees. In certain embodiments, form A2 is characterized by two or more 2θ peaks at 17.0, 18.7, and 21.7 degrees. In certain embodiments, form A2 is characterized by 2θ peaks at 17.0, 18.7, and 21.7 degrees.

In certain embodiments, form A2 is characterized by one or more 2θ peaks at 7.5, 10.8, 17.0, 17.5, 18.7, 20.5, 21.7, 22.3, 23.6, and 24.0, degrees. In certain embodiments, form A2 is characterized by two or more 2θ peaks at 7.5, 10.8, 17.0, 17.5, 18.7, 20.5, 21.7, 22.3, 23.6, and 24.0, degrees. In certain embodiments, form A2 is characterized by three or more 2θ peaks at 7.5, 10.8, 17.0, 17.5, 18.7, 20.5, 21.7, 22.3, 23.6, and 24.0, degrees. In certain embodiments, form A2 is characterized by four or more 2θ peaks at 7.5, 10.8, 17.0, 17.5, 18.7, 20.5, 21.7, 22.3, 23.6, and 24.0, degrees. In certain embodiments, form A2 is characterized by five or more 2θ peaks at 7.5, 10.8, 17.0, 17.5, 18.7, 20.5, 21.7, 22.3, 23.6, and 24.0, degrees. In certain embodiments, form A2 is characterized by six or more 2θ peaks at 7.5, 10.8, 17.0, 17.5, 18.7, 20.5, 21.7, 22.3, 23.6, and 24.0, degrees. In certain embodiments, form A2 is characterized by seven or more 2θ peaks at 7.5, 10.8, 17.0, 17.5, 18.7, 20.5, 21.7, 22.3, 23.6, and 24.0, degrees. In certain embodiments, form A2 is characterized by 2θ peaks at 7.5, 10.8, 17.0, 17.5, 18.7, 20.5, 21.7, 22.3, 23.6, and 24.0, degrees.

In certain embodiments, form A2 is characterized by 2θ peaks at

| No. | °2θ (Cu-Kα$_1$ radiation) ± 0.2° |
|---|---|
| 1 | 7.5 |
| 2 | 10.8 |
| 3 | 15.6 |
| 4 | 16.4 |
| 5 | 16.6 |
| 6 | 17 |
| 7 | 17.5 |
| 8 | 18.7 |
| 9 | 19.4 |
| 10 | 20.3 |
| 11 | 20.5 |
| 12 | 20.8 |
| 13 | 21.7 |
| 14 | 22.3 |
| 15 | 23.1 |
| 16 | 23.6 |
| 17 | 24 |
| 18 | 26.5 |
| 19 | 27.5 |
| 20 | 29.4 |

Figure 6:
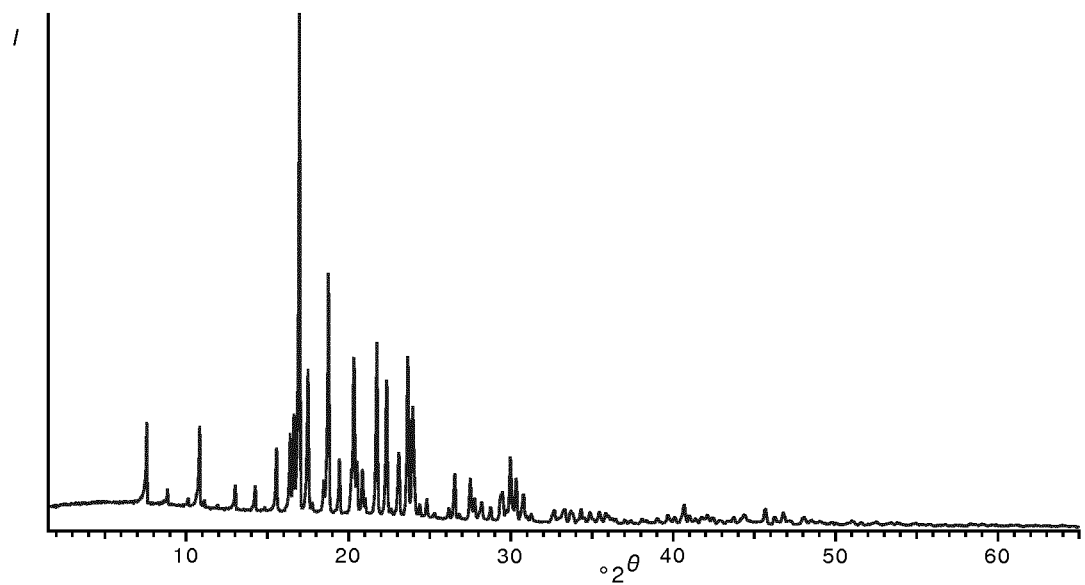
FIG. 6: Powder X-ray diffractogram of free base form A2.
Figure 7:
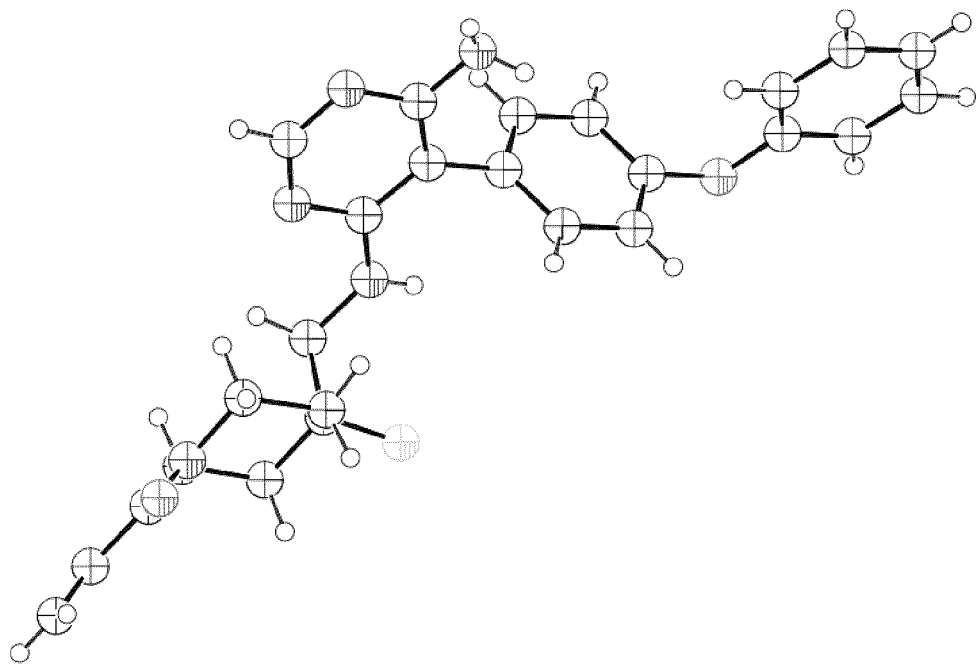
FIG. 7: Single crystal structure of free base form A2 viewed approx. along a-axis.
Figure 8:
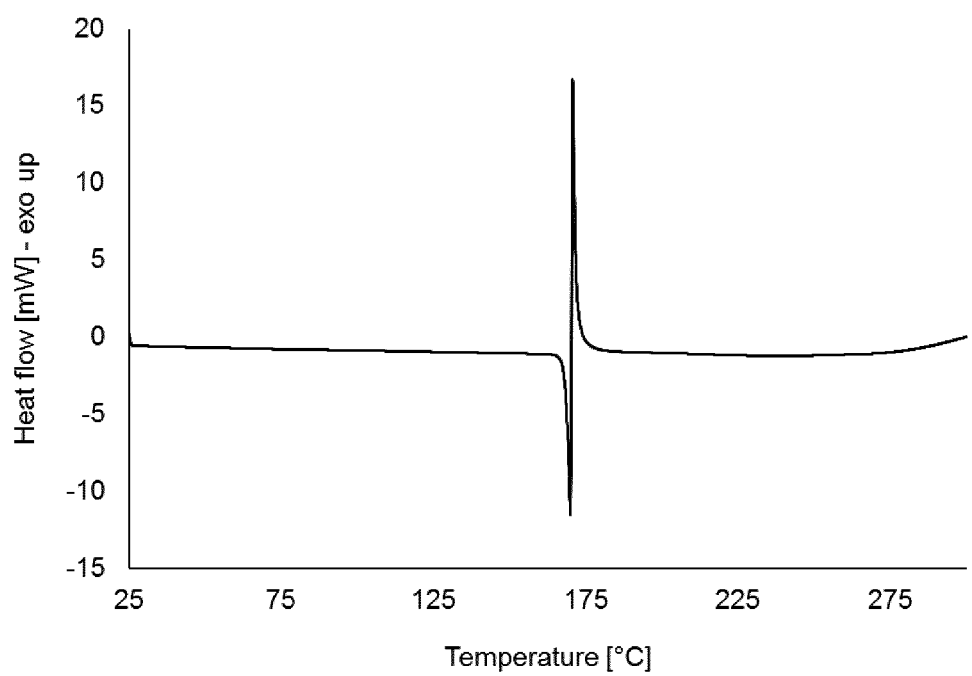
FIG. 8: DSC scan of free base form A2 (5 K/min).
Figure 9:
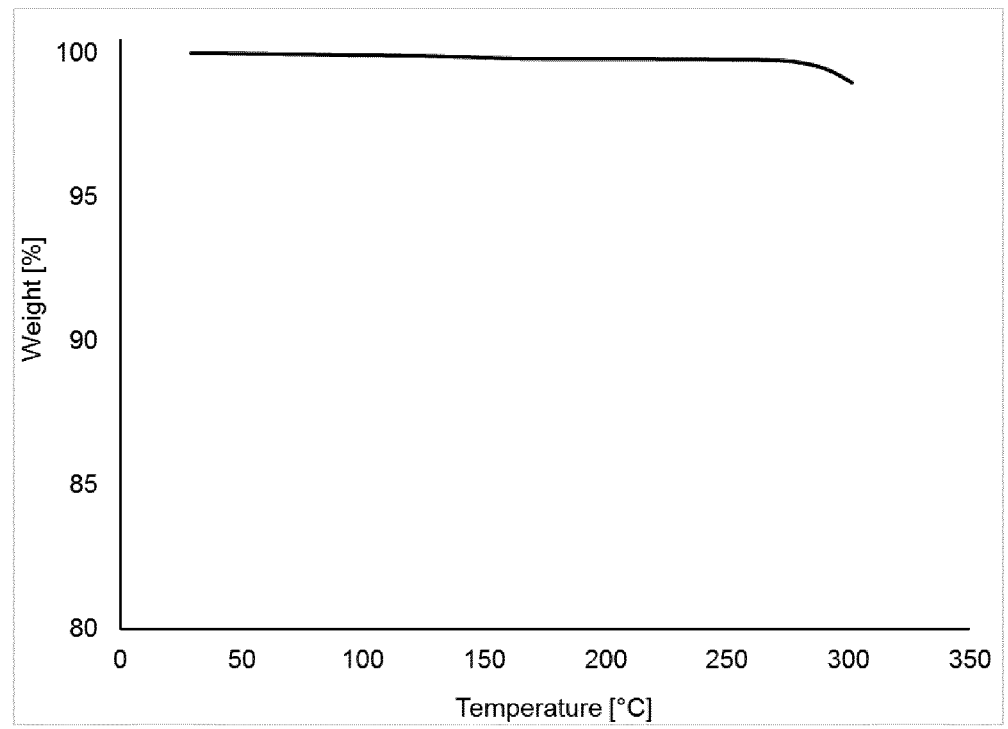
FIG. 9: TGA scan of free base form A2 (5 K/min).
Figure 10:
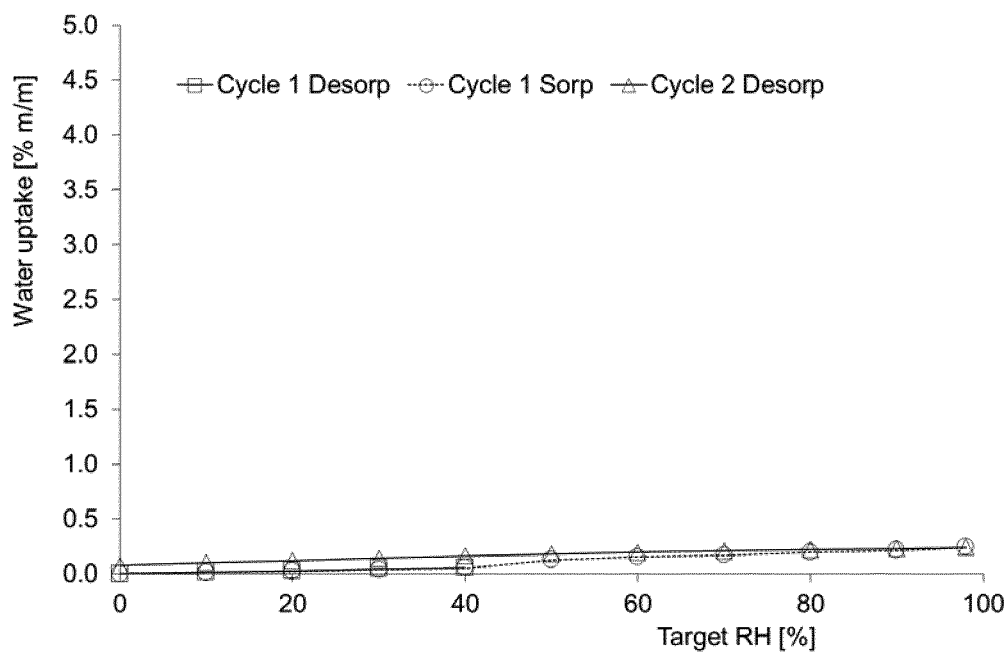
FIG. 10: Water Vapour Sorption Isotherm (25° C.) of free base form A2.

In another embodiment, form A2 is characterized by a diffraction pattern substantially similar to that of FIG. 6.

A Powder X-Ray Diffraction pattern of free base form A2 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In certain embodiments, form A2 crystallises in the triclinic space group P-1 with the lattice parameters (at 200 K) a=9.5326(12) Å, b=10.7284(14) Å, c=12.7734(16) Å, and α=70.960(12°), β=68.852(11°), γ=71.900(11°). Reasonably rounded, the parameters are a=9.5±0.1 Å, b=10.7±0.1 Å, c=12.8±0.1 Å, and α=71.0±0.1°, β=68.9±0.1°, γ=71.9±0.1°. From the single crystal structure it is clear that form A2 represents an anhydrous form.

In certain embodiments, form A2 is an anhydrous form. In certain embodiments, free base form A2 is a crystalline anhydrous form.

Other physical properties of form A2 include the following: T Thermal behaviour of form A2 showed a melting peak onset at approx. 168° C. Thermogravimetric analysis revealed a low weight loss of approx. 0.2% m/m up to this temperature. DSC and TGA profiles are displayed in the figures. DSC scan of form A2 was acquired on a Mettler-Toledo DSC 821e with a heating rate of 5 K/min, using nitrogen purge gas at 50 mL/min. TGA scan of form A2 was acquired on a Mettler-Toledo TGA 851 with a heating rate of 5 K/min, using nitrogen purge gas at 50 mL/min. Water Vapour Sorption behaviour of form A2 revealed small water uptake levels ≤1% m/m in the relative humidity (rh) range 0-80% rh, and very slightly elevated water uptake levels ≤2% m/m in the relative humidity (rh) range 90-98% rh. Form A2 can be classified as slightly hygroscopic acc. to Ph. Eur. Criteria (section 5.11.). Water Vapor Sorption isotherm (25° C.) of form A2 was displayed below. Water Vapour Sorption isotherm was acquired on a DVS-Intrinsic system from SMS. Thermodynamic solubility (24 h) of form A2 at 37° C. was determined to be approx. 10 µg/mL in Fasted-State Simulated Intestinal Fluid [FaSSIF, pH 6.5], and approx. 2 µg/mL in USP Phosphate buffer [pH 7.4], respectively (see example 6). Dissolution level of form A2 in Fasted-State Simulated Intestinal Fluid [FaSSIF, pH 6.5] at 37° C. was determined to be approx. 8 µg/mL after 2 h (see example 7). Overall, free base form A2 revealed good solid-state properties (good crystallinity, slightly hygroscopic, high thermal stability) with good manufacturability in larger scale.

In one embodiment, the invention provides for Compound 1 characterized as hydrochloride form HCl-NF1.

In certain embodiments, form HCl-NF1 is characterized by one or more 2θ peaks at 15.7, 19.1, 20.3, and 20.8 degrees. In certain embodiments, form HCl-NF1 is characterized by two or more 2θ peaks at 15.7, 19.1, 20.3, and 20.8 degrees. In certain embodiments, form HCl-NF1 is characterized by 2θ peaks at 15.7, 19.1, 20.3, and 20.8 degrees.

In certain embodiments, form HCl-NF1 is characterized by one or more 2θ peaks at 10.3, 13.7, 15.7, 19.1, 20.3, 20.8, and 21.9 degrees. In certain embodiments, form HCl-NF1 is characterized by two or more 2θ peaks at 10.3, 13.7, 15.7, 19.1, 20.3, 20.8, and 21.9 degrees. In certain embodiments, form HCl-NF1 is characterized by three or more 2θ peaks at 10.3, 13.7, 15.7, 19.1, 20.3, 20.8, and 21.9 degrees. In certain embodiments, form HCl-NF1 is characterized by four or more 2θ peaks at 10.3, 13.7, 15.7, 19.1, 20.3, 20.8, and 21.9 degrees. In certain embodiments, form HCl-NF1 is characterized by five or more 2θ peaks at 10.3, 13.7, 15.7, 19.1, 20.3, 20.8, and 21.9 degrees. In certain embodiments, form HCl-NF1 is characterized by six or more 2θ peaks at 10.3, 13.7, 15.7, 19.1, 20.3, 20.8, and 21.9 degrees. In certain embodiments, form HCl-NF1 is characterized by 2θ peaks at 10.3, 13.7, 15.7, 19.1, 20.3, 20.8, and 21.9 degrees.

In certain embodiments, form HCl-NF1 is characterized by 2θ peaks at

| No. | °2θ (Cu-Kα$_1$ radiation) ± 0.2° |
| --- | --- |
| 1 | 6.9 |
| 2 | 10.3 |
| 3 | 12.9 |
| 4 | 13.7 |
| 5 | 15.7 |
| 6 | 16.5 |
| 7 | 17.2 |
| 8 | 17.7 |
| 9 | 18.1 |
| 10 | 18.5 |
| 11 | 19.1 |
| 12 | 20.3 |
| 13 | 20.8 |
| 14 | 21.9 |
| 15 | 22.6 |
| 16 | 22.8 |
| 17 | 23.3 |
| 18 | 23.7 |
| 19 | 24.4 |
| 20 | 26 |
| 21 | 26.6 |

Figure 11:
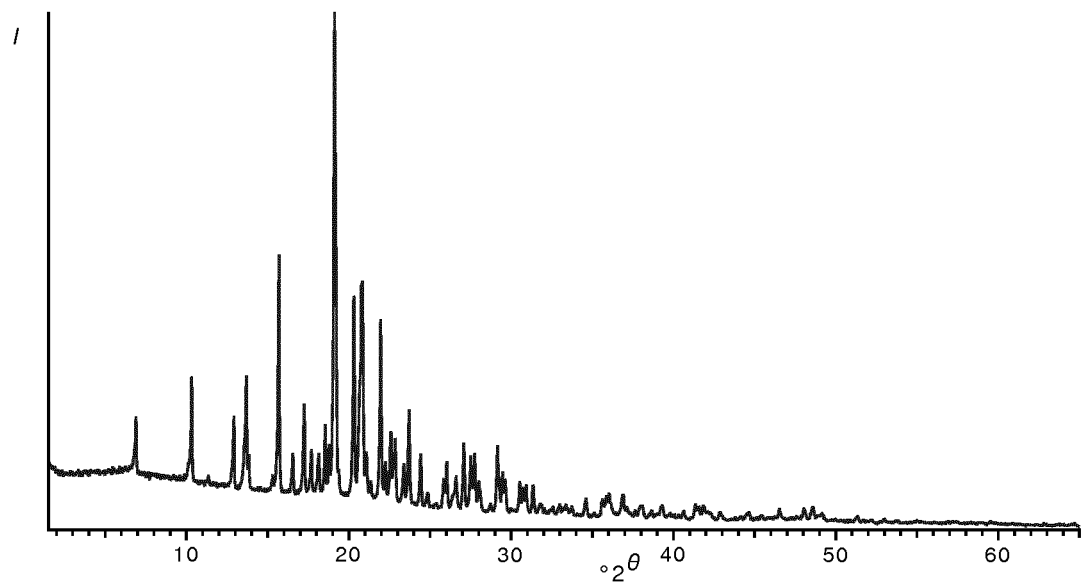
FIG. 11: Powder X-ray diffractogram of Hydrochloride form HCl-NF1.
Figure 12:
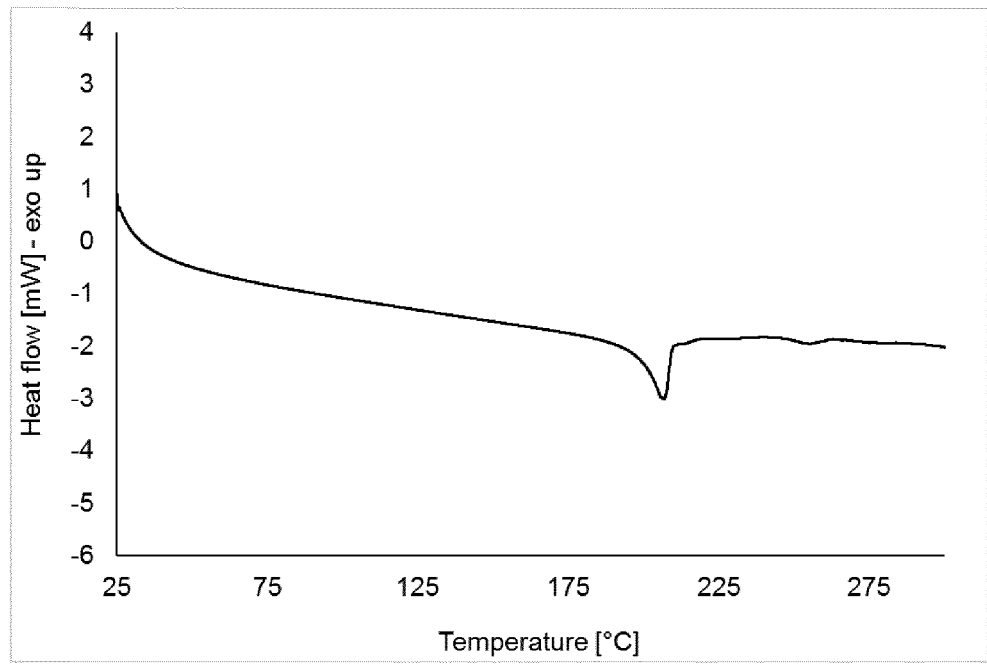
FIG. 12: DSC scan of Hydrochloride form HCl-NF1 (5 K/min).
Figure 13:
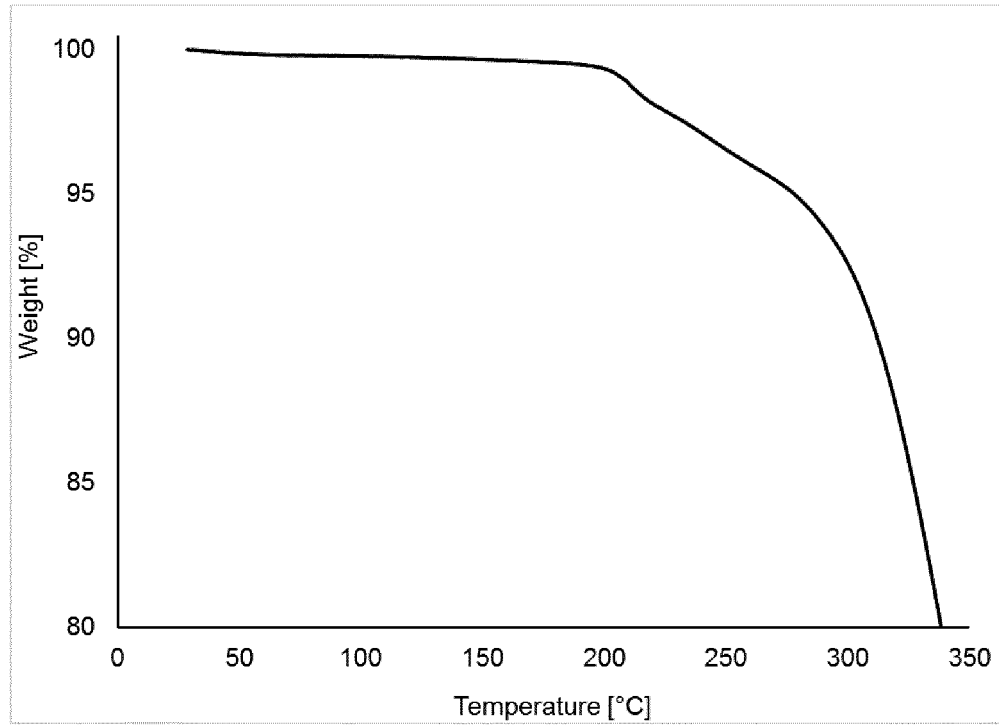
FIG. 13: TGA scan of Hydrochloride form HCl-NF1 (5 K/min).
Figure 14:
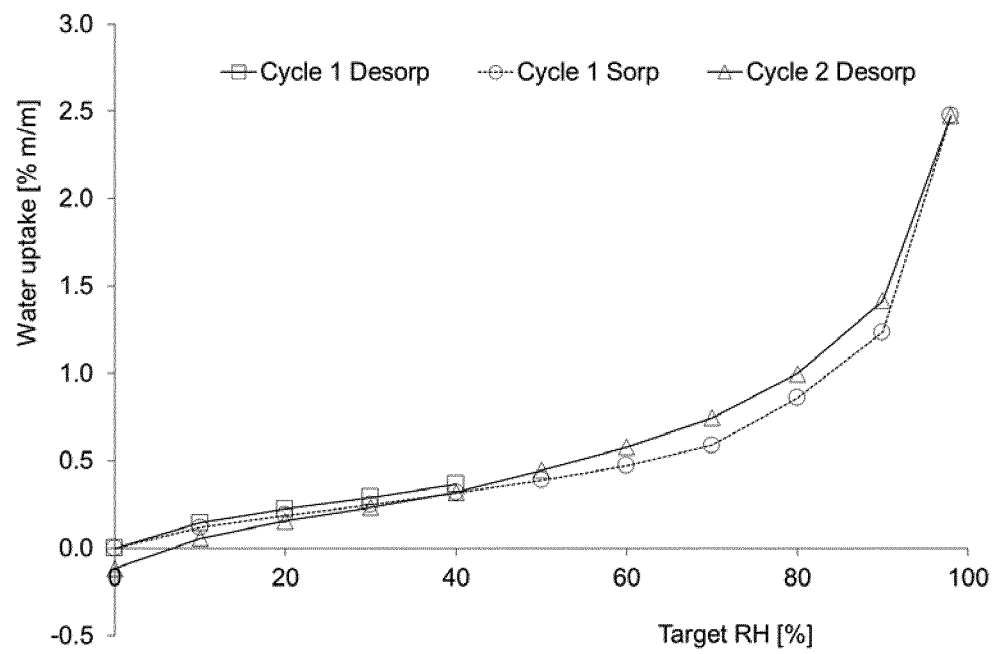
FIG. 14: Water Vapour Sorption Isotherm (25° C.) of Hydrochloride form HCl-NF1.

In another embodiment, form HCl-NF1 is characterized by a diffraction pattern substantially similar to that of FIG. 11.

A Powder X-Ray Diffraction pattern of form HCl-NF1 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe Sta-diP 611 KL transmission diffractometer).

In another embodiment, form HCl-NF1 is characterized as a crystalline anhydrous form.

Other physical properties of form HCl-NF1 include the following: Thermal behaviour of Hydrochloride form HCl-NF1 showed a melting peak onset at approx. 200° C. Thermogravimetric analysis revealed a low weight loss of approx. 0.7% m/m up to this temperature. DSC and TGA profiles are displayed in the figures. DSC scan of Hydrochloride form HCl-NF1 was acquired on a Mettler-Toledo DSC 821e with a heating rate of 5 K/min, using nitrogen purge gas at 50 mL/min. TGA scan of Hydrochloride form HCl-NF1 was acquired on a Mettler-Toledo TGA 851 with a heating rate of 5 K/min, using nitrogen purge gas at 50 mL/min. Water Vapour Sorption behaviour of Hydrochloride form HCl-NF1 revealed small water uptake levels ≤1% m/m in the relative humidity (rh) range 0-80% rh, and slightly elevated water uptake levels ≤5% m/m in the relative humidity (rh) range 90-98% rh. Hydrochloride form HCl-NF1 can be classified as slightly hygroscopic acc. to Ph. Eur. Criteria (section 5.11.). Water Vapor Sorption isotherm (25° C.) of Hydrochloride form HCl-NF1 is displayed in the figures. Water Vapour Sorption isotherm was acquired on a DVS-Intrinsic system from SMS. Dissolution level of Hydrochloride form HCl-NF1 in Fasted-State Simulated Intestinal Fluid [FaSSIF, pH 6.5] at 37° C. was determined to be approx. 46 μg/mL after 2 h (see example 7). Overall, Hydrochloride form HCl-NF1 revealed good solid-state properties (good crystallinity, slightly hygroscopic, high thermal stability).

In one embodiment, the invention provides for Compound 1 characterized as hydrochloride form HCl-NF2.

In certain embodiments, form HCl-NF2 is characterized by one or more 2θ peaks at 7.8, 13.0, and 15.6 degrees. In certain embodiments, form HCl-NF2 is characterized by two or more 2θ peaks at 7.8, 13.0, and 15.6 degrees. In certain embodiments, form HCl-NF2 is characterized by 2θ peaks at 7.8, 13.0, and 15.6 degrees.

In certain embodiments, form HCl-NF2 is characterized by one or more 2θ peaks at 6.5, 7.8, 9.1, 13.0, and 22.0 degrees. In certain embodiments, form HCl-NF2 is characterized by two or more 2θ peaks at 6.5, 7.8, 9.1, 13.0, and 22.0 degrees. In certain embodiments, form HCl-NF2 is characterized by three or more 2θ peaks at 6.5, 7.8, 9.1, 13.0, and 22.0 degrees. In certain embodiments, form HCl-NF2 is characterized by four or more 2θ peaks at 6.5, 7.8, 9.1, 13.0, and 22.0 degrees. In certain embodiments, form HCl-NF2 is characterized by 2θ peaks at 6.5, 7.8, 9.1, 13.0, and 22.0 degrees.

In certain embodiments, form HCl-NF2 is characterized by 2θ peaks at

| No. | °2θ (Cu-Kα$_1$ radiation) ± 0.2° |
| --- | --- |
| 1 | 6.5 |
| 2 | 7.8 |
| 3 | 8.2 |
| 4 | 9.1 |
| 5 | 10.0 |
| 6 | 13.0 |
| 7 | 15.6 |
| 8 | 16.4 |
| 9 | 17.3 |
| 10 | 17.6 |
| 11 | 18.2 |
| 12 | 21.2 |
| 13 | 22.0 |
| 14 | 23.0 |
| 15 | 26.2 |
| 16 | 31.7 |

Figure 15:
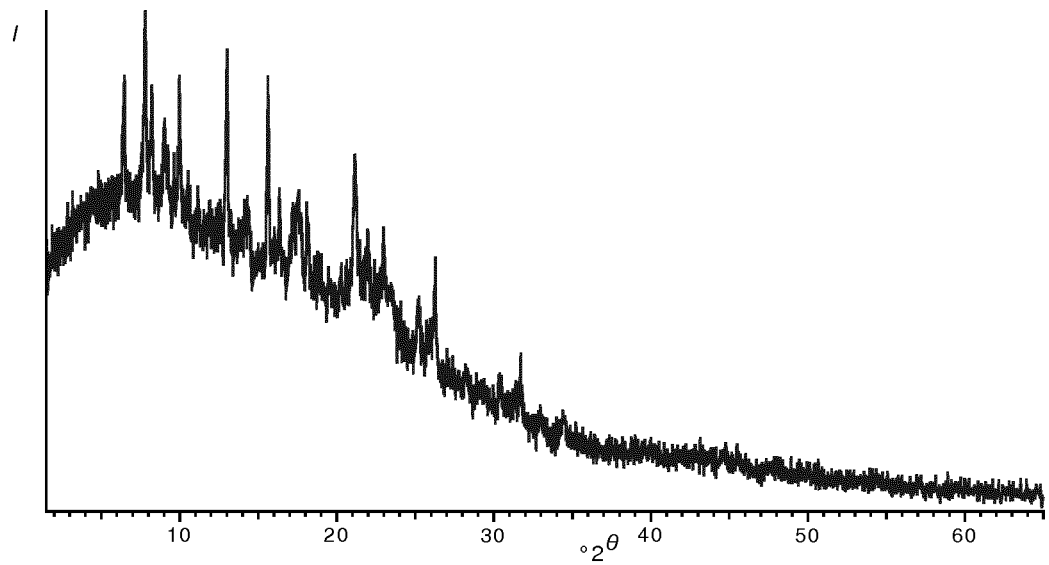
FIG. 15: Powder X-ray diffractogram of Hydrochloride form HCl-NF2.
Figure 16:
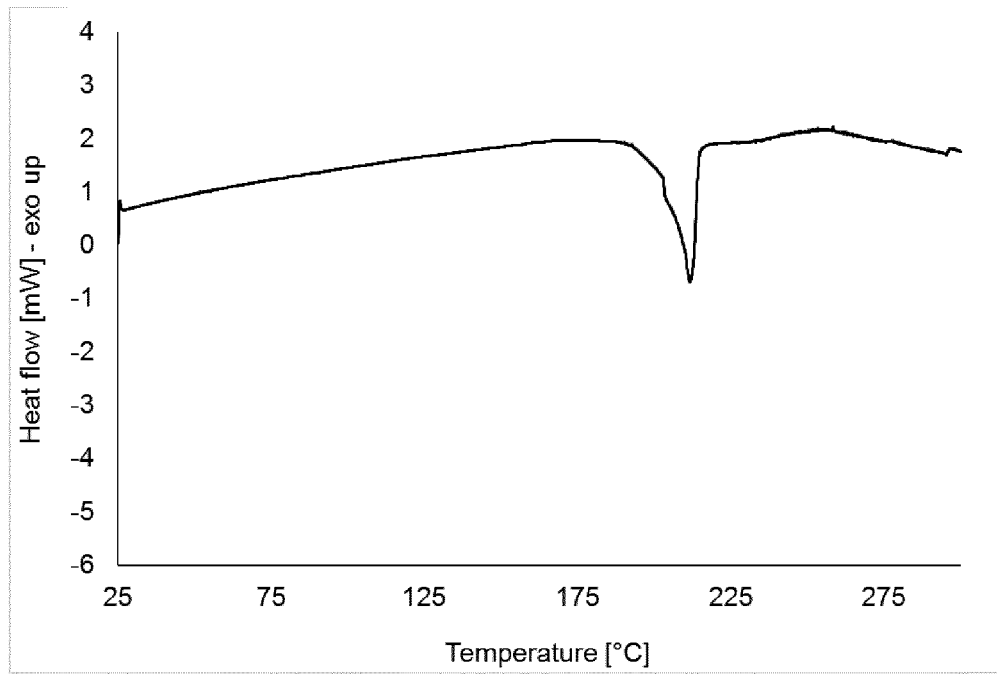
FIG. 16: DSC scan of Hydrochloride form HCl-NF2 (5 K/min).
Figure 17:
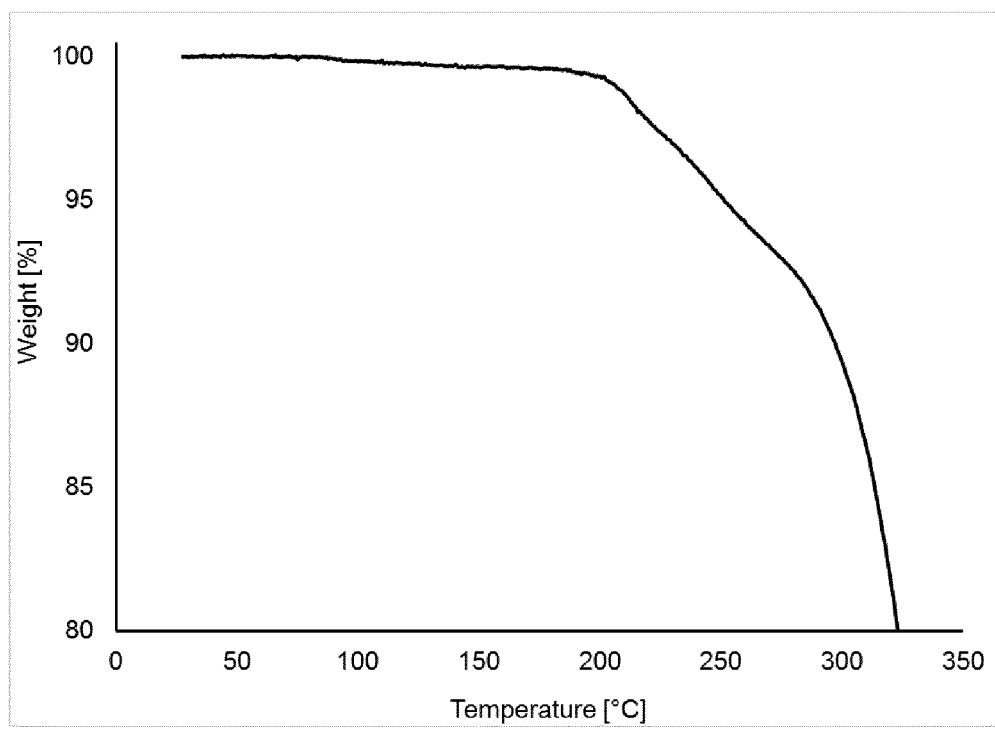
FIG. 17: TGA scan of Hydrochloride form HCl-NF2 (5 K/min).

In another embodiment, form HCl-NF2 is characterized by a diffraction pattern substantially similar to that of FIG. 15.

A Powder X-Ray Diffraction pattern of form HCl-NF2 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe Sta-diP 611 KL transmission diffractometer).

In another embodiment, form HCl-NF2 is characterized as a crystalline anhydrous form.

Other physical properties of form HCl-NF2 include the following: Thermal behaviour of Hydrochloride form HCl-NF2 showed a melting peak onset at approx. 192° C. Thermogravimetric analysis revealed a low weight loss of approx. 0.6% m/m up to this temperature. DSC and TGA profiles are displayed in the figures. DSC scan of Hydrochloride form HCl-NF2 was acquired on a Mettler-Toledo DSC 821e with a heating rate of 5 K/min, using nitrogen purge gas at 50 mL/min. TGA scan of Hydrochloride form HCl-NF2 was acquired on a Mettler-Toledo TGA/DSC 1 with a heating rate of 5 K/min, using nitrogen purge gas at 50 mL/min. Overall, Hydrochloride form HCl-NF2 reveals good solid-state properties (crystallinity, high thermal stability).

In one embodiment, the invention provides for Compound 1 characterized as hydrochloride form HCl-NF3.

In certain embodiments, form HCl-NF3 is characterized by one or more 2θ peaks at 14.8, 16.8, 20.1, and 20.4, degrees. In certain embodiments, form HCl-NF3 is characterized by two or more 2θ peaks at 14.8, 16.8, 20.1, and 20.4, degrees. In certain embodiments, form HCl-NF3 is characterized by 2θ peaks at 14.8, 16.8, 20.1, and 20.4, degrees.

In certain embodiments, form HCl-NF3 is characterized by one or more 2θ peaks at 9.7, 13.5, 14.8, 16.8, 20.1, 20.4, and 23.0 degrees. In certain embodiments, form HCl-NF3 is characterized by two or more 2θ peaks at 9.7, 13.5, 14.8, 16.8, 20.1, 20.4, and 23.0 degrees. In certain embodiments, form HCl-NF3 is characterized by three or more 2θ peaks at 9.7, 13.5, 14.8, 16.8, 20.1, 20.4, and 23.0 degrees. In certain embodiments, form HCl-NF3 is characterized by four or more 2θ peaks at 9.7, 13.5, 14.8, 16.8, 20.1, 20.4, and 23.0 degrees. In certain embodiments, form HCl-NF3 is characterized by five or more 2θ peaks at 9.7, 13.5, 14.8, 16.8, 20.1, 20.4, and 23.0 degrees. In certain embodiments, form HCl-NF3 is characterized by six or more 2θ peaks at 9.7, 13.5, 14.8, 16.8, 20.1, 20.4, and 23.0 degrees. In certain embodiments, form HCl-NF3 is characterized by 2θ peaks at 9.7, 13.5, 14.8, 16.8, 20.1, 20.4, and 23.0 degrees.

In certain embodiments, form HCl-NF3 is characterized by 2θ peaks at

| No. | °2θ (Cu-Kα$_1$ radiation) ± 0.2° |
|---|---|
| 1 | 9.7 |
| 2 | 10.9 |
| 3 | 13.5 |
| 4 | 13.9 |
| 5 | 14.8 |
| 6 | 16.8 |
| 7 | 18.3 |
| 8 | 19.4 |
| 9 | 19.7 |
| 10 | 20.1 |
| 11 | 20.4 |
| 12 | 22.2 |
| 13 | 23 |
| 14 | 24.1 |
| 15 | 27.5 |
| 16 | 27.9 |

Figure 18:
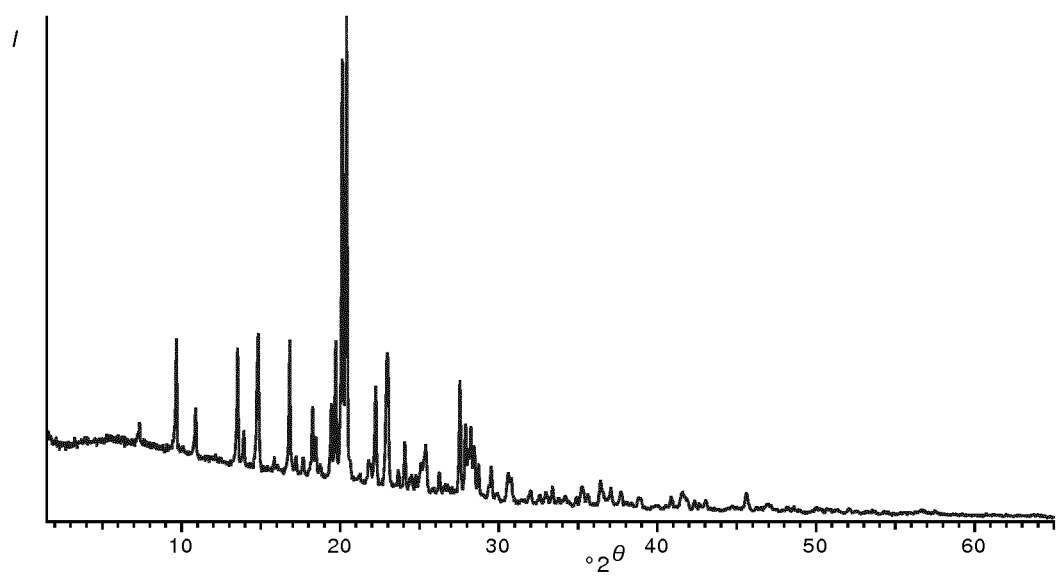
FIG. 18: Powder X-ray diffractogram of Hydrochloride form HCl-NF3.
Figure 19:
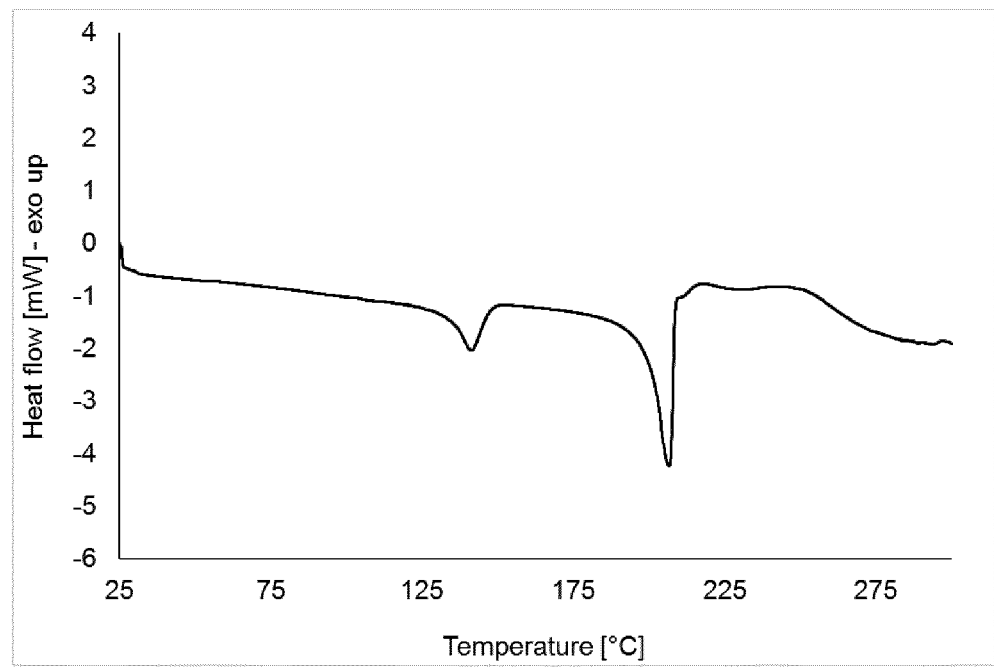
FIG. 19: DSC scan of Hydrochloride form HCl-NF3 (5 K/min).
Figure 20:
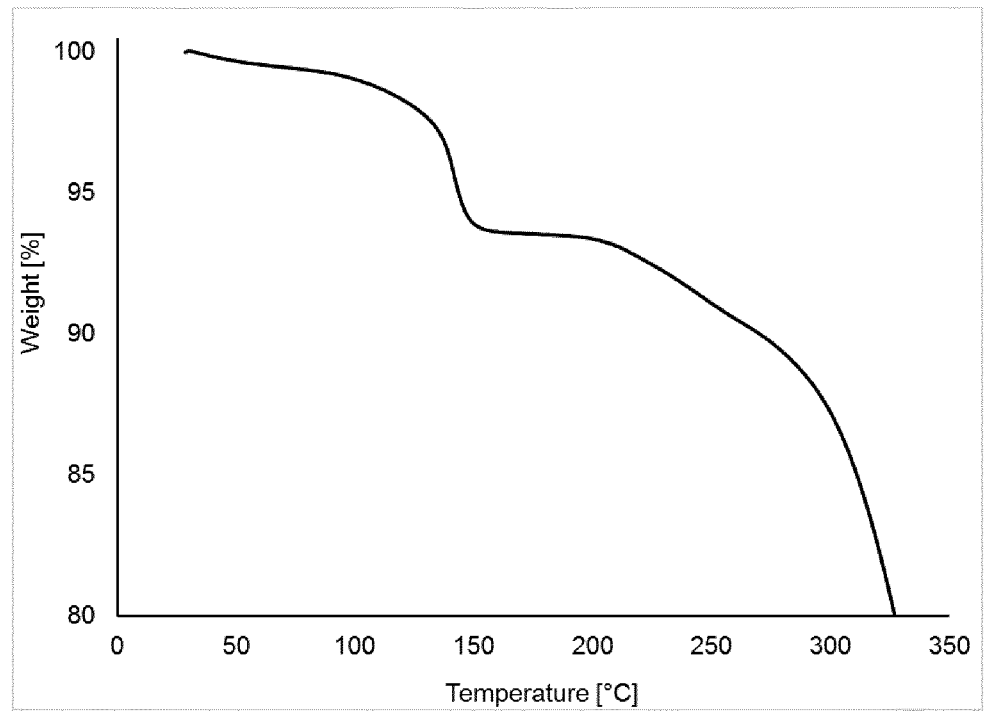
FIG. 20: TGA scan of Hydrochloride form HCl-NF3 (5 K/min).

In another embodiment, form HCl-NF3 is characterized by a diffraction pattern substantially similar to that of FIG. 18.

A Powder X-Ray Diffraction pattern of form HCl-NF3 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form HCl-NF3 is characterized as a crystalline solvate form.

Other physical properties of form HCl-NF3 include the following: Thermal behaviour of Hydrochloride form HCl-NF3 showed a melting peak onset at approx. 200° C. Thermogravimetric analysis revealed a weight loss of approx. 7% m/m up to this temperature. DSC and TGA profiles are displayed in the figures. DSC scan of Hydrochloride form HCl-NF3 was acquired on a Mettler-Toledo DSC 821e with a heating rate of 5 K/min, using nitrogen purge gas at 50 mL/min. TGA scan of Hydrochloride form HCl-NF3 was acquired on a Mettler-Toledo TGA 851 with a heating rate of 5 K/min, using nitrogen purge gas at 50 mL/min. Overall, Hydrochloride form HCl-NF3 revealed good solid-state properties (good crystallinity, high thermal stability).

In one embodiment, the invention provides for Compound 1 characterized as hydrobromide form HBr-NF1.

In certain embodiments, form HBr-NF1 is characterized by one or more 2θ peaks at 6.9, 19.1, 20.4, 20.8, and 21.9 degrees. In certain embodiments, form HBr-NF1 is characterized by two or more 2θ peaks at 6.9, 19.1, 20.4, 20.8, and 21.9 degrees. In certain embodiments, form HBr-NF1 is characterized by 2θ peaks at 6.9, 19.1, 20.4, 20.8, and 21.9 degrees.

In certain embodiments, form HBr-NF1 is characterized by one or more 2θ peaks at 6.9, 13.6, 15.5, 16.5, 19.1, 20.4, 20.8, 21.9, and 23.5 degrees. In certain embodiments, form HBr-NF1 is characterized by two or more 2θ peaks at 6.9, 13.6, 15.5, 16.5, 19.1, 20.4, 20.8, 21.9, and 23.5 degrees. In certain embodiments, form HBr-NF1 is characterized by three or more 2θ peaks at 6.9, 13.6, 15.5, 16.5, 19.1, 20.4, 20.8, 21.9, and 23.5 degrees. In certain embodiments, form HBr-NF1 is characterized by four or more 2θ peaks at 6.9, 13.6, 15.5, 16.5, 19.1, 20.4, 20.8, 21.9, and 23.5 degrees. In certain embodiments, form HBr-NF1 is characterized by five or more 2θ peaks at 6.9, 13.6, 15.5, 16.5, 19.1, 20.4, 20.8, 21.9, and 23.5 degrees. In certain embodiments, form HBr-NF1 is characterized by six or more 2θ peaks at 6.9, 13.6, 15.5, 16.5, 19.1, 20.4, 20.8, 21.9, and 23.5 degrees. In certain embodiments, form HBr-NF1 is characterized by seven or more 2θ peaks at 6.9, 13.6, 15.5, 16.5, 19.1, 20.4, 20.8, 21.9, and 23.5 degrees. In certain embodiments, form HBr-NF1 is characterized by 2θ peaks at 6.9, 13.6, 15.5, 16.5, 19.1, 20.4, 20.8, 21.9, and 23.5 degrees.

In certain embodiments, form HBr-NF1 is characterized by 2θ peaks at

| No. | °2θ (Cu-Kα$_1$ radiation) ± 0.2° |
|---|---|
| 1 | 6.9 |
| 2 | 9 |
| 3 | 10.9 |
| 4 | 11.3 |
| 5 | 12.6 |
| 6 | 13.6 |
| 7 | 15.5 |
| 8 | 16.5 |
| 9 | 17.8 |
| 10 | 18.7 |
| 11 | 19.1 |
| 12 | 20 |
| 13 | 20.4 |
| 14 | 20.8 |

-continued

| No. | °2θ (Cu-Kα$_1$ radiation) ± 0.2° |
|---|---|
| 15 | 21.9 |
| 16 | 22.5 |
| 17 | 22.8 |
| 18 | 23.5 |
| 19 | 23.9 |
| 20 | 24.8 |
| 21 | 25.4 |

Figure 21:
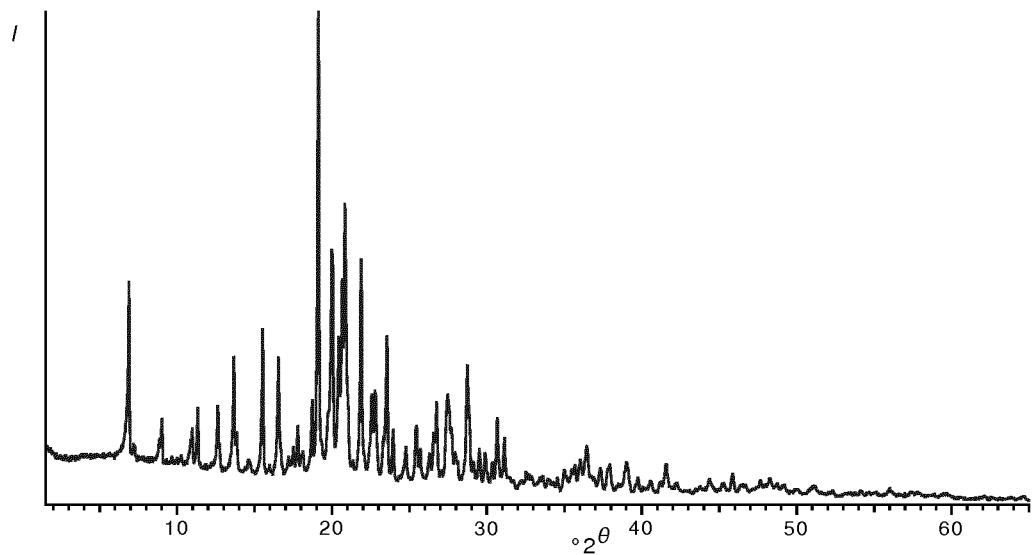
FIG. 21: Powder X-ray diffractogram of Hydrobromide form HBr-NF1.
Figure 22:
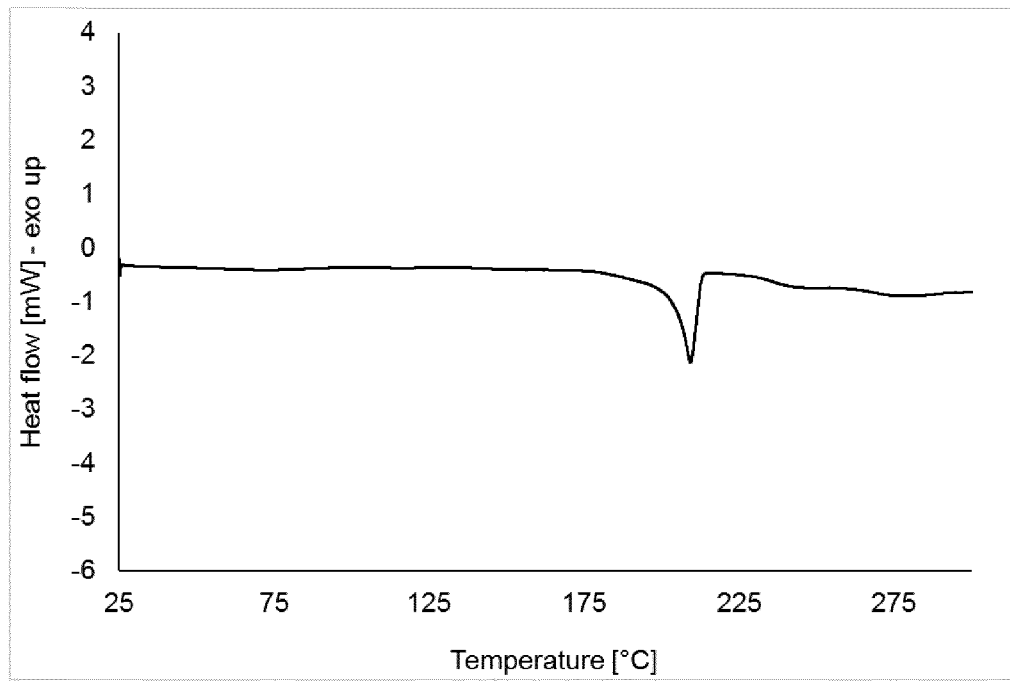
FIG. 22: DSC scan of Hydrobromide form HBr-NF1 (5 K/min).
Figure 23:
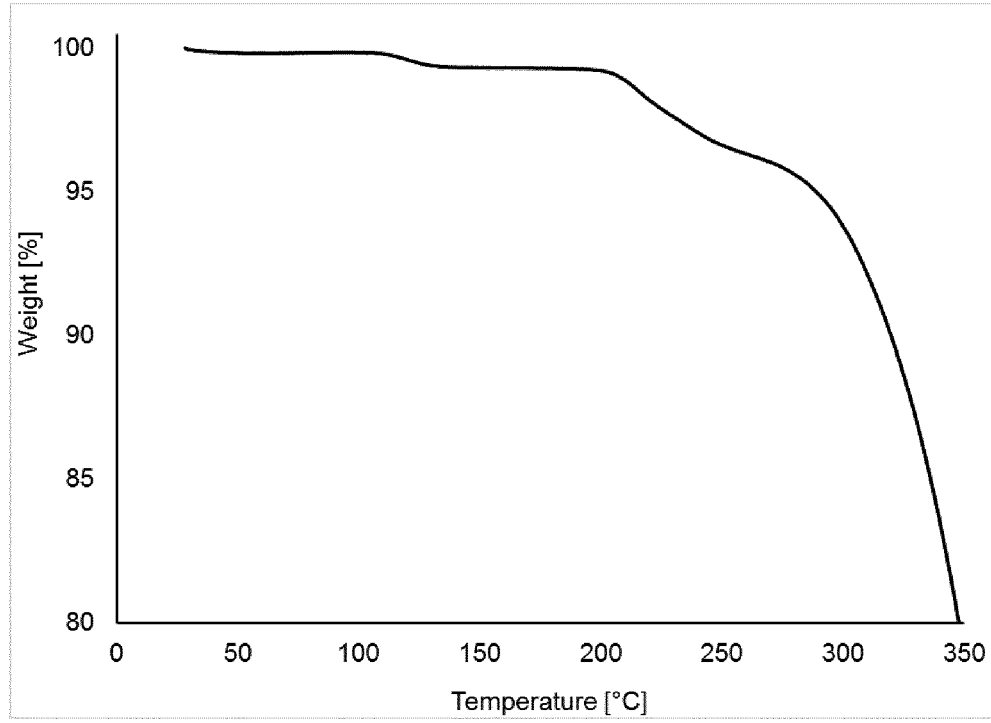
FIG. 23: TGA scan of Hydrobromide form HBr-NF1 (5 K/min).
Figure 24:
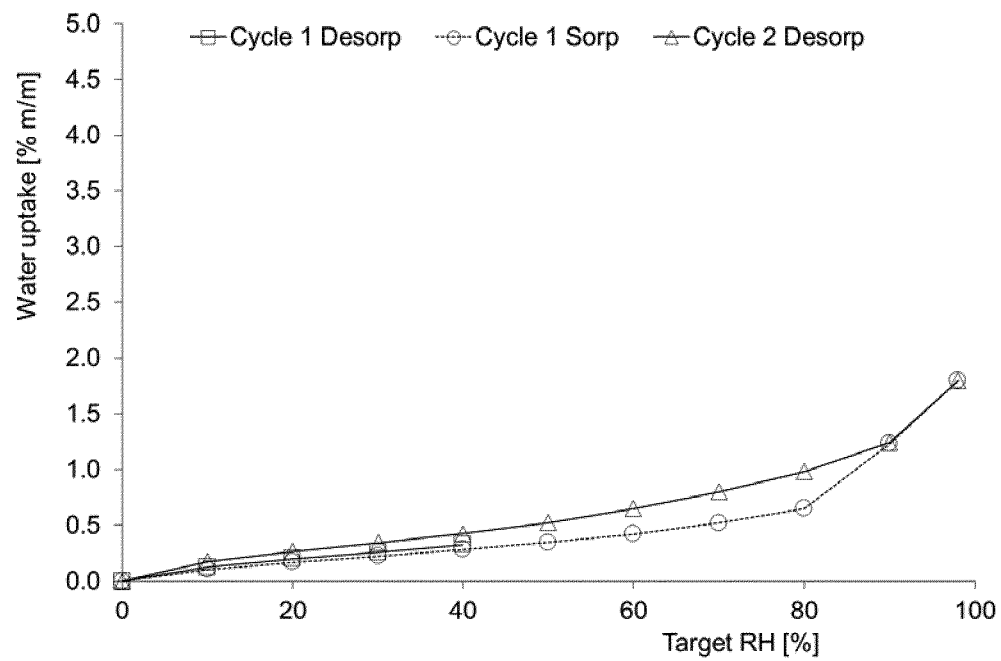
FIG. 24: Water Vapour Sorption Isotherm (25° C.) of Hydrobromide form HBr-NF1.

In another embodiment, form HBr-NF1 is characterized by a diffraction pattern substantially similar to that of FIG. 21.

A Powder X-Ray Diffraction pattern of free base form HBr-NF1 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form HBr-NF1 is characterized as a crystalline anhydrous form.

Other physical properties of form HBr-NF1 include the following: Thermal behaviour of Hydrobromide form HBr-NF1 showed a melting peak onset at approx. 203° C. Thermogravimetric analysis revealed a low weight loss of approx. 0.8% m/m up to this temperature. DSC and TGA profiles are displayed in the figures. DSC scan of Hydrobromide form HBr-NF1 was acquired on a Mettler-Toledo DSC 821e with a heating rate of 5 K/min, using nitrogen purge gas at 50 mL/min. TGA scan of Hydrobromide form HBr-NF1 was acquired on a Mettler-Toledo TGA 851 with a heating rate of 5 K/min, using nitrogen purge gas at 50 mL/min. Water Vapour Sorption behaviour of Hydrobromide form HBr-NF1 revealed small water uptake levels ≤1% m/m in the relative humidity (rh) range 0-80% rh, and slightly elevated water uptake levels ≤5% m/m in the relative humidity (rh) range 90-98% rh. Hydrobromide form HBr-NF1 can be classified as slightly hygroscopic acc. to Ph. Eur. Criteria (section 5.11.). Water Vapor Sorption isotherm (25° C.) of Hydrobromide form HBr-NF1 is displayed in the figures. Water Vapour Sorption isotherm was acquired on a DVS-Intrinsic system from SMS. Dissolution level of Hydrobromide form HBr-NF1 in Fasted-State Simulated Intestinal Fluid [FaSSIF, pH 6.5] at 37° C. was determined to be approx. 35 µg/mL after 2 h (see example 7). Overall, Hydrobromide form HBr-NF1 revealed good solid-state properties (good crystallinity, slightly hygroscopic, high thermal stability).

In one embodiment, the invention provides for Compound 1 characterized as hydrobromide form HBr-NF2.

In certain embodiments, form HBr-NF2 is characterized by one or more 2θ peaks at 4.9, 13.2, and 20.0 degrees. In certain embodiments, form HBr-NF2 is characterized by two or more 2θ peaks at 4.9, 13.2, and 20.0 degrees. In certain embodiments, form HBr-NF2 is characterized by 2θ peaks at 4.9, 13.2, and 20.0 degrees.

In certain embodiments, form HBr-NF2 is characterized by one or more 2θ peaks at 4.9, 7.5, 13.2, 20.0, and 20.6 degrees. In certain embodiments, form HBr-NF2 is characterized by two or more 2θ peaks at 4.9, 7.5, 13.2, 20.0, and 20.6 degrees. In certain embodiments, form HBr-NF2 is characterized by three or more 2θ peaks at 4.9, 7.5, 13.2, 20.0, and 20.6 degrees. In certain embodiments, form HBr-NF2 is characterized by four or more 2θ peaks at 4.9, 7.5, 13.2, 20.0, and 20.6 degrees. In certain embodiments, form HBr-NF2 is characterized by 2θ peaks at 4.9, 7.5, 13.2, 20.0, and 20.6 degrees.

In certain embodiments, form HBr-NF2 is characterized by 2θ peaks at

| No. | °2θ (Cu-Kα$_1$ radiation) ± 0.2° |
|---|---|
| 1 | 4.9 |
| 2 | 7.5 |
| 3 | 13.2 |
| 4 | 19.6 |
| 5 | 20.0 |
| 6 | 20.6 |

Figure 25:
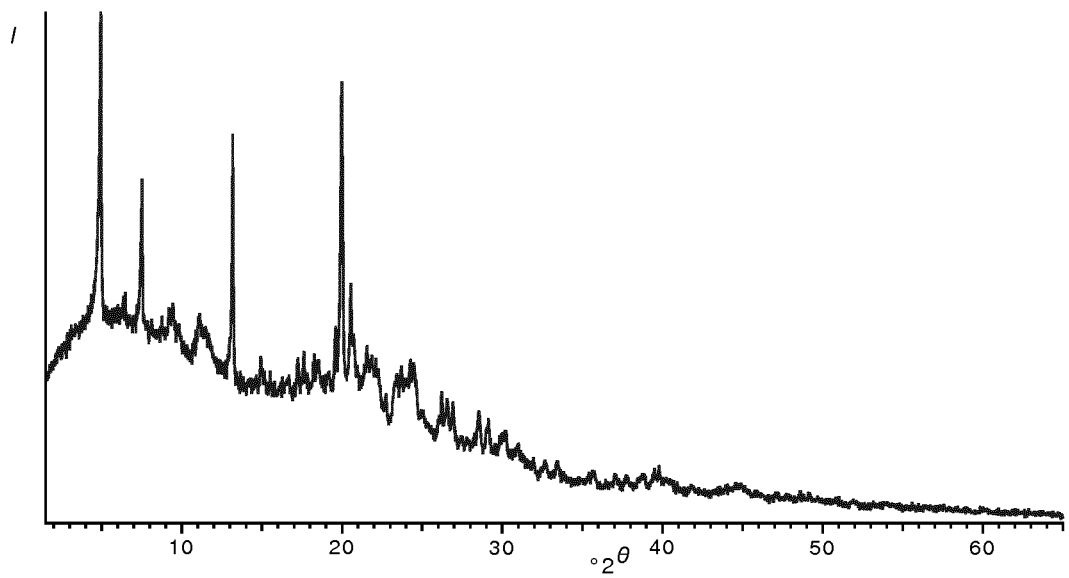
FIG. 25: Powder X-ray diffractogram of Hydrobromide form HBr-NF2.
Figure 26:
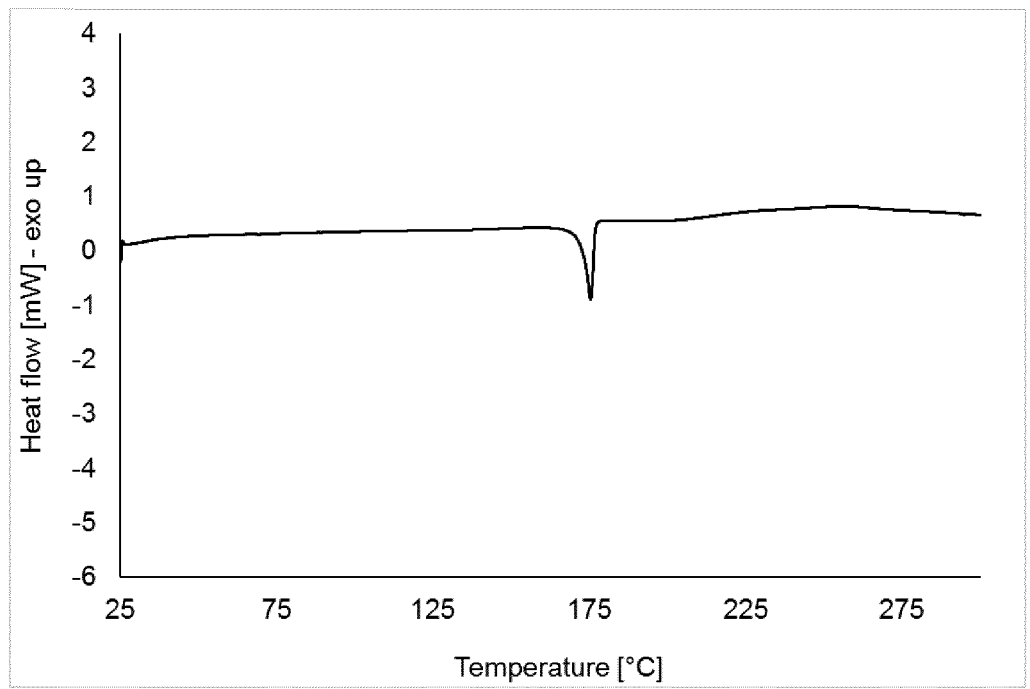
FIG. 26: DSC scan of Hydrobromide form HBr-NF2 (5 K/min).
Figure 27:
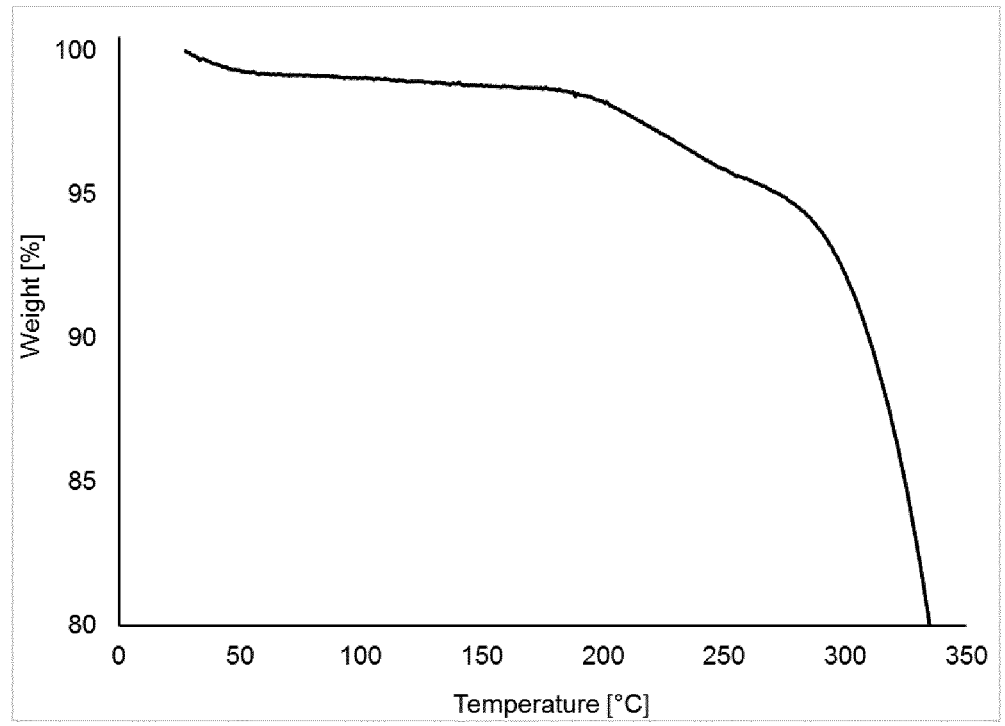
FIG. 27: TGA scan of Hydrobromide form HBr-NF2 (5 K/min).
Figure 28:
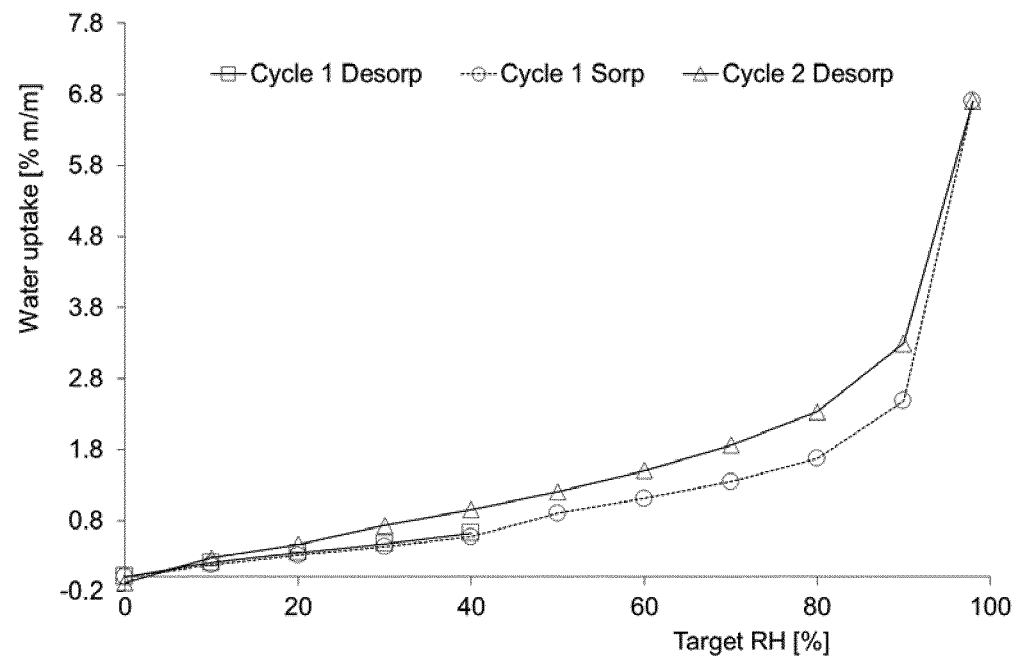
FIG. 28: Water Vapour Sorption Isotherm (25° C.) of Hydrobromide form HBr-NF2.

In another embodiment, form HBr-NF2 is characterized by a diffraction pattern substantially similar to that of FIG. 25.

A Powder X-Ray Diffraction pattern of free base form HBr-NF2 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form HBr-NF2 is characterized as a crystalline anhydrous form.

Other physical properties of form HBr-NF2 include the following: Thermal behaviour of Hydrobromide form HBr-NF2 showed a melting peak onset at approx. 173° C. Thermogravimetric analysis revealed a weight loss of approx. 1.3% m/m up to this temperature. DSC and TGA profiles are displayed in the figures. DSC scan of Hydrobromide form HBr-NF2 was acquired on a Mettler-Toledo DSC 821e with a heating rate of 5 K/min, using nitrogen purge gas at 50 mL/min. TGA scan of Hydrobromide form HBr-NF2 was acquired on a Mettler-Toledo TGA/DSC 1 with a heating rate of 5 K/min, using nitrogen purge gas at 50 mL/min. Water Vapour Sorption behaviour of Hydrobromide form HBr-NF2 revealed small water uptake levels ≤1% m/m in the relative humidity (rh) range 0-80% rh, and elevated water uptake levels ≥5% m/m in the relative humidity (rh) range 90-98% rh. Hydrobromide form HBr-NF2 can be classified as slightly hygroscopic acc. to Ph. Eur. Criteria (section 5.11.). Water Vapor Sorption isotherm (25° C.) of Hydrobromide form HBr-NF2 is displayed in the figures. Water Vapour Sorption isotherm was acquired on a DVS-Intrinsic system from SMS. Overall, Hydrobromide form HBr-NF2 revealed good solid-state properties (good crystallinity, slightly hygroscopic, high thermal stability).

In one embodiment, the invention provides for Compound 1 characterized as oxalate form Oxalate-NF1.

In certain embodiments, form Oxalate-NF1 is characterized by one or more 2θ peaks at 16.2, 17.7, 18.6, 21.1, and 21.3, degrees. In certain embodiments, form Oxalate-NF1 is characterized by two or more 2θ peaks at 16.2, 17.7, 18.6, 21.1, and 21.3, degrees. In certain embodiments, form Oxalate-NF1 is characterized by 2θ peaks at 16.2, 17.7, 18.6, 21.1, and 21.3, degrees.

In certain embodiments, form Oxalate-NF1 is characterized by one or more 2θ peaks at 8.2, 10.4, 13.0, 16.2, 17.7, 18.6, 21.1, 21.3, and 23.2 degrees. In certain embodiments, form Oxalate-NF1 is characterized by two or more 2θ peaks at 8.2, 10.4, 13.0, 16.2, 17.7, 18.6, 21.1, 21.3, and 23.2 degrees. In certain embodiments, form Oxalate-NF1 is characterized by three or more 2θ peaks at 8.2, 10.4, 13.0, 16.2, 17.7, 18.6, 21.1, 21.3, and 23.2 degrees. In certain embodiments, form Oxalate-NF1 is characterized by four or more 2θ peaks at 8.2, 10.4, 13.0, 16.2, 17.7, 18.6, 21.1, 21.3, and 23.2 degrees. In certain embodiments, form Oxalate-NF1 is characterized by five or more 2θ peaks at 8.2, 10.4, 13.0, 16.2, 17.7, 18.6, 21.1, 21.3, and 23.2 degrees. In certain embodiments, form Oxalate-NF1 is characterized by six or more 2θ peaks at 8.2, 10.4, 13.0, 16.2, 17.7, 18.6, 21.1, 21.3, and 23.2 degrees. In certain embodiments, form Oxalate-NF1 is characterized by seven or more 2θ peaks at 8.2, 10.4, 13.0, 16.2, 17.7, 18.6, 21.1, 21.3, and 23.2 degrees. In certain embodiments, form Oxalate-NF1 is characterized by 2θ peaks at 8.2, 10.4, 13.0, 16.2, 17.7, 18.6, 21.1, 21.3, and 23.2 degrees.

In certain embodiments, form Oxalate-NF1 is characterized by 2θ peaks at

| No. | °2θ (Cu-Kα$_1$ radiation) ± 0.2° |
|---|---|
| 1 | 8.2 |
| 2 | 9.6 |
| 3 | 10.4 |
| 4 | 13 |
| 5 | 13.8 |
| 6 | 16.2 |
| 7 | 17.2 |
| 8 | 17.7 |
| 9 | 18.6 |
| 10 | 19 |
| 11 | 20.2 |
| 12 | 20.4 |
| 13 | 21.1 |
| 14 | 21.3 |
| 15 | 22.4 |
| 16 | 23.2 |
| 17 | 24 |
| 18 | 24.5 |
| 19 | 25 |
| 20 | 25.5 |
| 21 | 27.6 |

Figure 29:
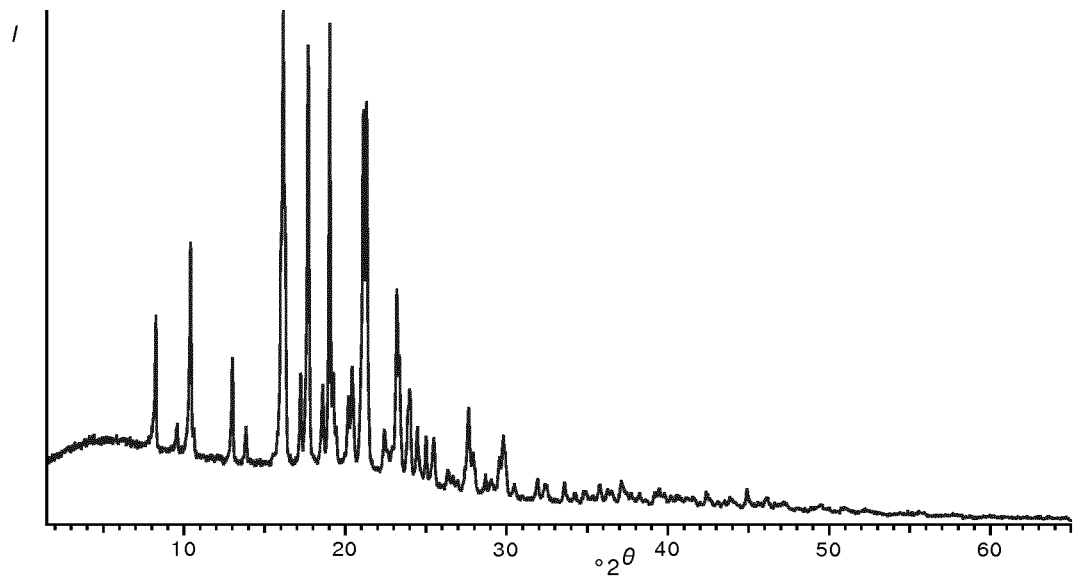
FIG. 29: Powder X-ray diffractogram of Oxalate form Oxalate-NF1.
Figure 30:
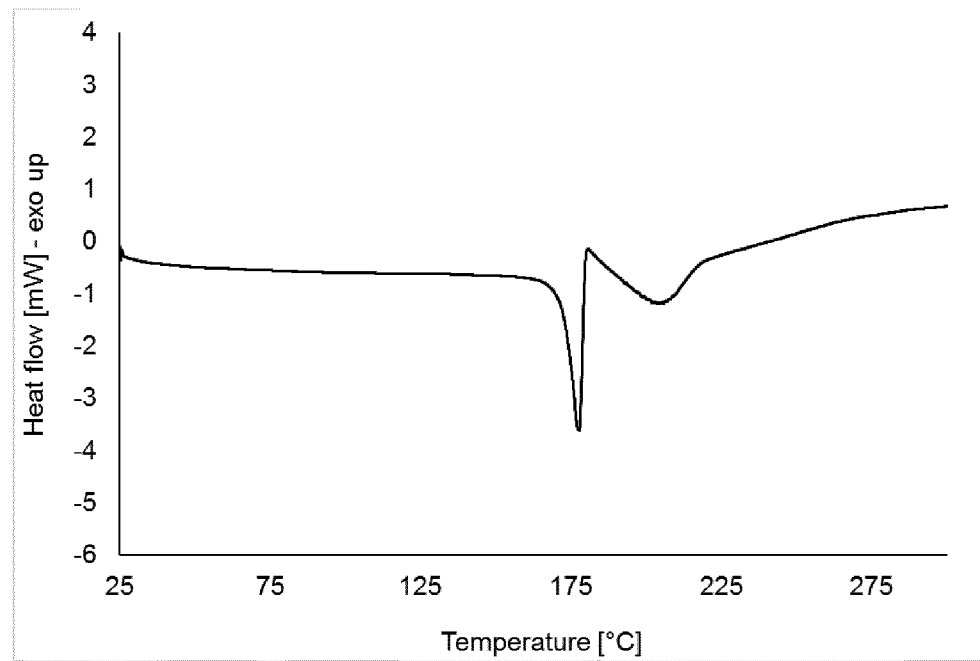
FIG. 30: DSC scan of Oxalate form Oxalate-NF1 (5 K/min).
Figure 31:
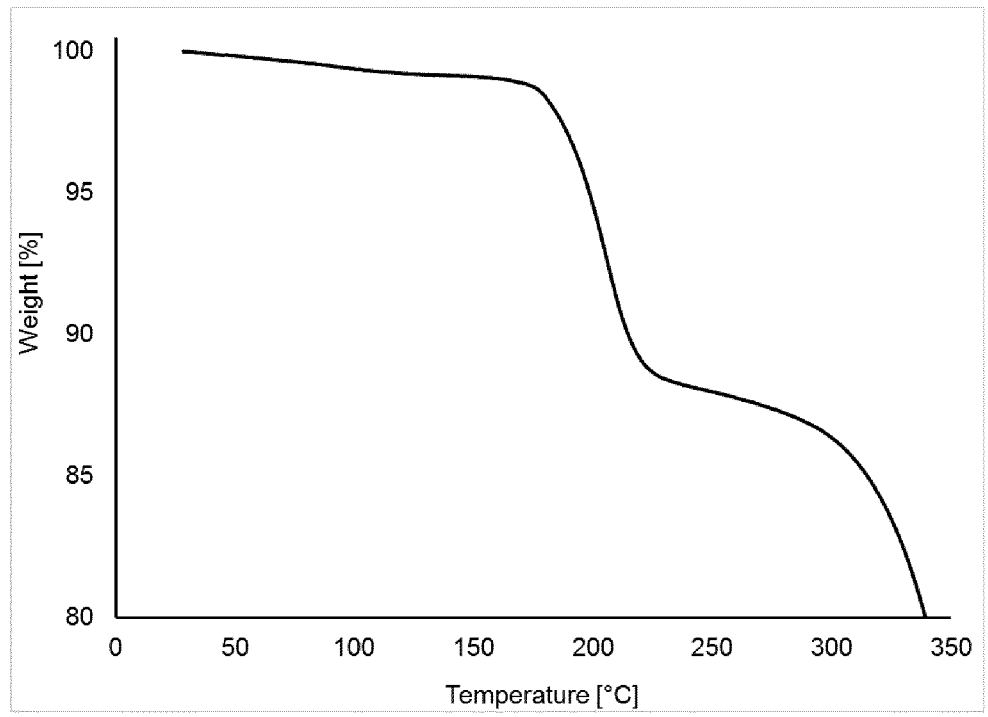
FIG. 31: TGA scan of Oxalate form Oxalate-NF1 (5 K/min).
Figure 32:
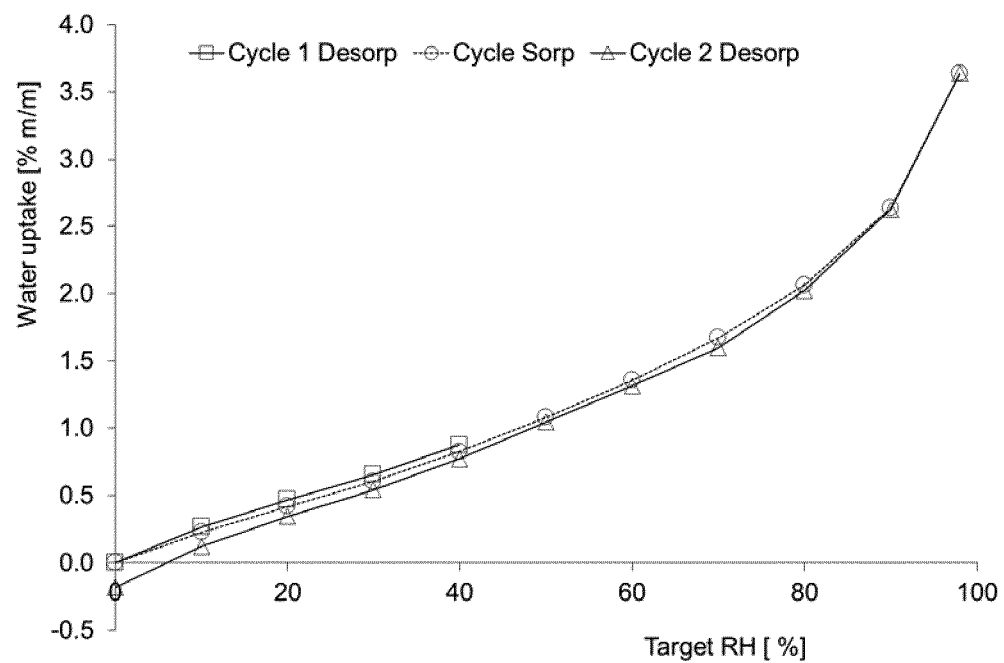
FIG. 32: Water Vapour Sorption Isotherm (25° C.) of Oxalate form Oxalate-NF1.

In another embodiment, form Oxalate-NF1 is characterized by a diffraction pattern substantially similar to that of FIG. 29.

A Powder X-Ray Diffraction pattern of free base form Oxalate-NF1 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form Oxalate-NF1 is characterized as a crystalline anhydrous form.

Other physical properties of form Oxalate-NF1 include the following: Thermal behaviour of Oxalate form Oxalate-NF1 showed a melting peak onset at approx. 173° C. Thermogravimetric analysis revealed a weight loss of approx. 1.2% m/m up to this temperature. DSC and TGA profiles are displayed in the figures. DSC scan of Oxalate form Oxalate-NF1 was acquired on a Mettler-Toledo DSC 821e with a heating rate of 5 K/min, using nitrogen purge gas at 50 mL/min. TGA scan of Oxalate form Oxalate-NF1 was acquired on a Mettler-Toledo TGA 851 with a heating rate of 5 K/min, using nitrogen purge gas at 50 mL/min. Water Vapour Sorption behaviour of Oxalate form Oxalate-NF1 revealed small water uptake levels ≤1% m/m in the relative humidity (rh) range 0-80% rh, and slightly elevated water uptake levels ≤5% m/m in the relative humidity (rh) range 90-98% rh. Oxalate form Oxalate-NF1 can be classified as slightly hygroscopic acc. to Ph. Eur. Criteria (section 5.11.). Water Vapor Sorption isotherm (25° C.) of Oxalate form Oxalate-NF1 is displayed in the figures. Water Vapour Sorption isotherm was acquired on a DVS-Intrinsic system from SMS. Dissolution level of Oxalate form Oxalate-NF1 in Fasted-State Simulated Intestinal Fluid [FaSSIF, pH 6.5] at 37° C. was determined to be approx. 53 μg/mL after 2 h (see example 7). Overall, Oxalate form Oxalate-NF1 revealed good solid-state properties (good crystallinity, slightly hygroscopic, high thermal stability).

In one embodiment, the invention provides for Compound 1 characterized as maleate form Maleate-NF1.

In certain embodiments, form Maleate-NF1 is characterized by one or more 2θ peaks at 18.1, 19.1, 20.8, and 24.8 degrees. In certain embodiments, form Maleate-NF1 is characterized by two or more 2θ peaks at 18.1, 19.1, 20.8, and 24.8 degrees. In certain embodiments, form Maleate-NF1 is characterized by 2θ peaks at 18.1, 19.1, 20.8, and 24.8 degrees.

In certain embodiments, form Maleate-NF1 is characterized by one or more 2θ peaks at 6.5, 10.3, 11.5, 12.8, 18.1, 18.7, 19.1, 20.8, and 24.8 degrees. In certain embodiments, form Maleate-NF1 is characterized by two or more 2θ peaks at 6.5, 10.3, 11.5, 12.8, 18.1, 18.7, 19.1, 20.8, and 24.8 degrees. In certain embodiments, form Maleate-NF1 is characterized by three or more 2θ peaks at 6.5, 10.3, 11.5, 12.8, 18.1, 18.7, 19.1, 20.8, and 24.8 degrees. In certain embodiments, form Maleate-NF1 is characterized by four or more 2θ peaks at 6.5, 10.3, 11.5, 12.8, 18.1, 18.7, 19.1, 20.8, and 24.8 degrees. In certain embodiments, form Maleate-NF1 is characterized by five or more 2θ peaks at 6.5, 10.3, 11.5, 12.8, 18.1, 18.7, 19.1, 20.8, and 24.8 degrees. In certain embodiments, form Maleate-NF1 is characterized by six or more 2θ peaks at 6.5, 10.3, 11.5, 12.8, 18.1, 18.7, 19.1, 20.8, and 24.8 degrees. In certain embodiments, form Maleate-NF1 is characterized by seven or more 2θ peaks at 6.5, 10.3, 11.5, 12.8, 18.1, 18.7, 19.1, 20.8, and 24.8 degrees. In certain embodiments, form Maleate-NF1 is characterized by 2θ peaks at 6.5, 10.3, 11.5, 12.8, 18.1, 18.7, 19.1, 20.8, and 24.8 degrees.

In certain embodiments, form Maleate-NF1 is characterized by 2θ peaks at

| No. | °2θ (Cu-Kα$_1$ radiation) ± 0.2° |
|---|---|
| 1 | 6.5 |
| 2 | 10.3 |
| 3 | 11.5 |
| 4 | 12.8 |
| 5 | 14.8 |
| 6 | 17.1 |
| 7 | 17.3 |
| 8 | 17.8 |
| 9 | 18.1 |
| 10 | 18.7 |
| 11 | 19.1 |
| 12 | 19.4 |
| 13 | 19.8 |
| 14 | 20.2 |
| 15 | 20.8 |
| 16 | 21.5 |
| 17 | 22.6 |
| 18 | 24.5 |
| 19 | 24.8 |
| 20 | 25.3 |
| 21 | 26.4 |

Figure 33:
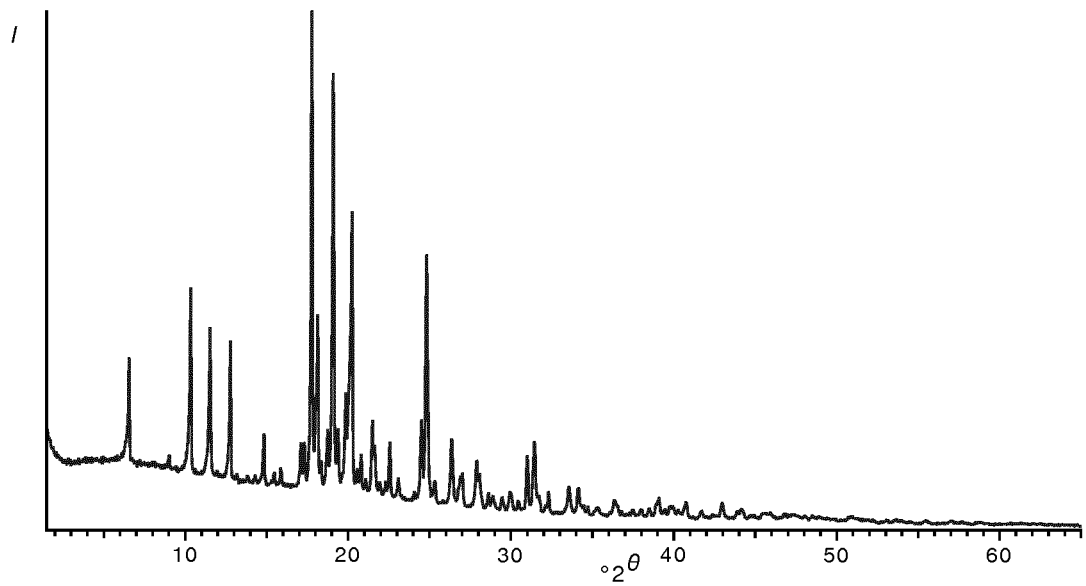
FIG. 33: Powder X-ray diffractogram of Maleate salt form Maleate-NF1.
Figure 34:
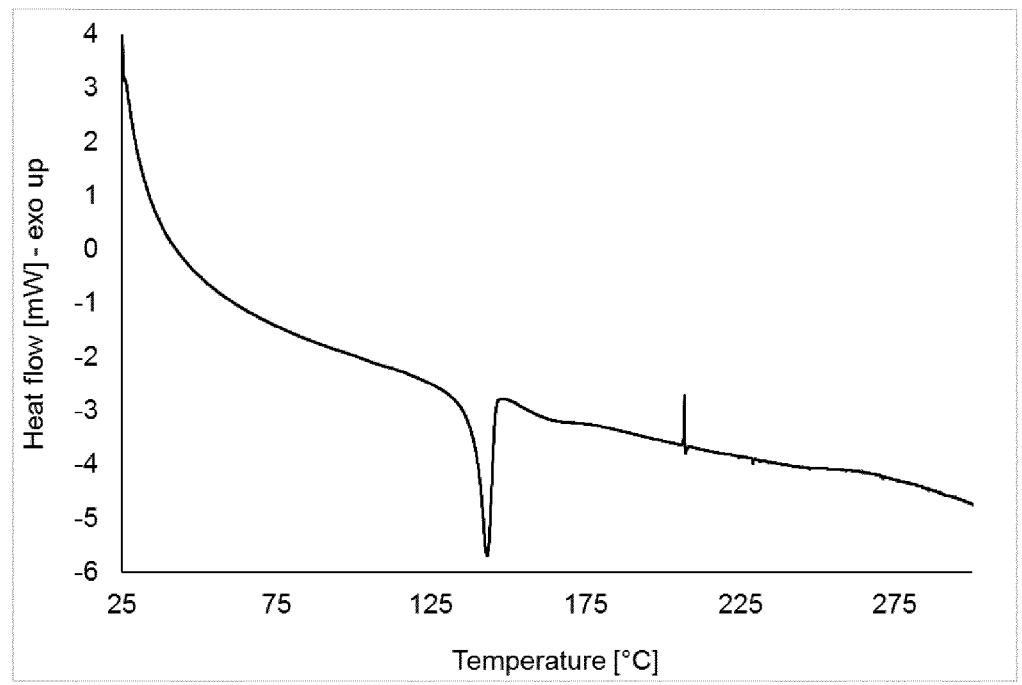
FIG. 34: DSC scan of Maleate salt form Maleate-NF1 (5 K/min).
Figure 35:
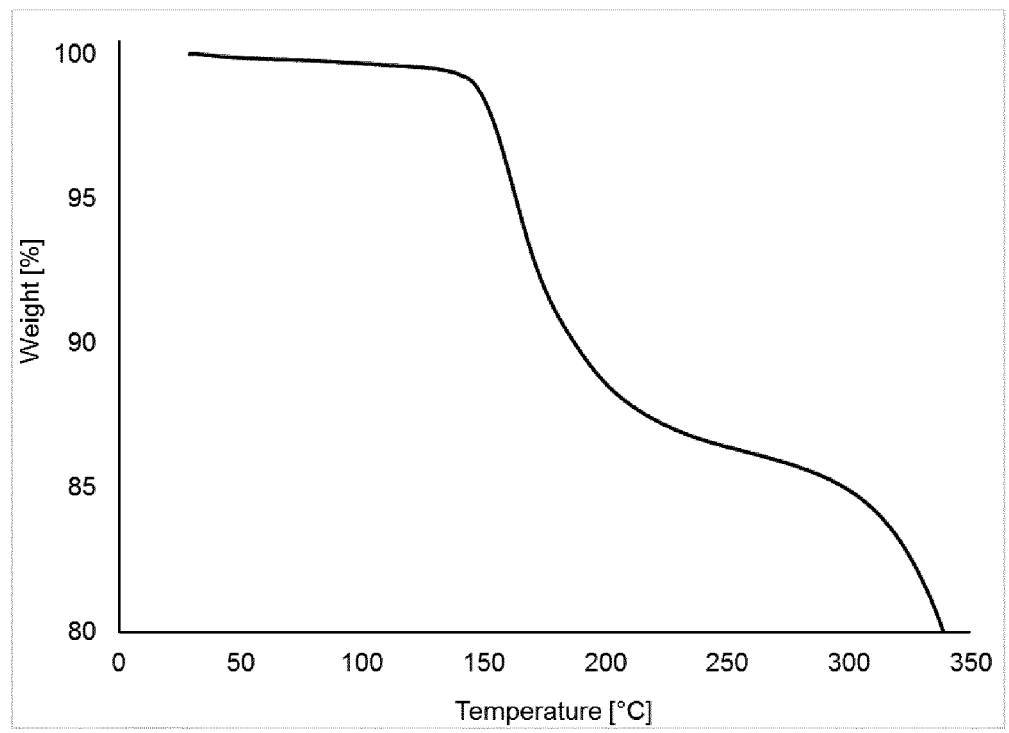
FIG. 35: TGA scan of Maleate salt form Maleate-NF1 (5 K/min).
Figure 36:
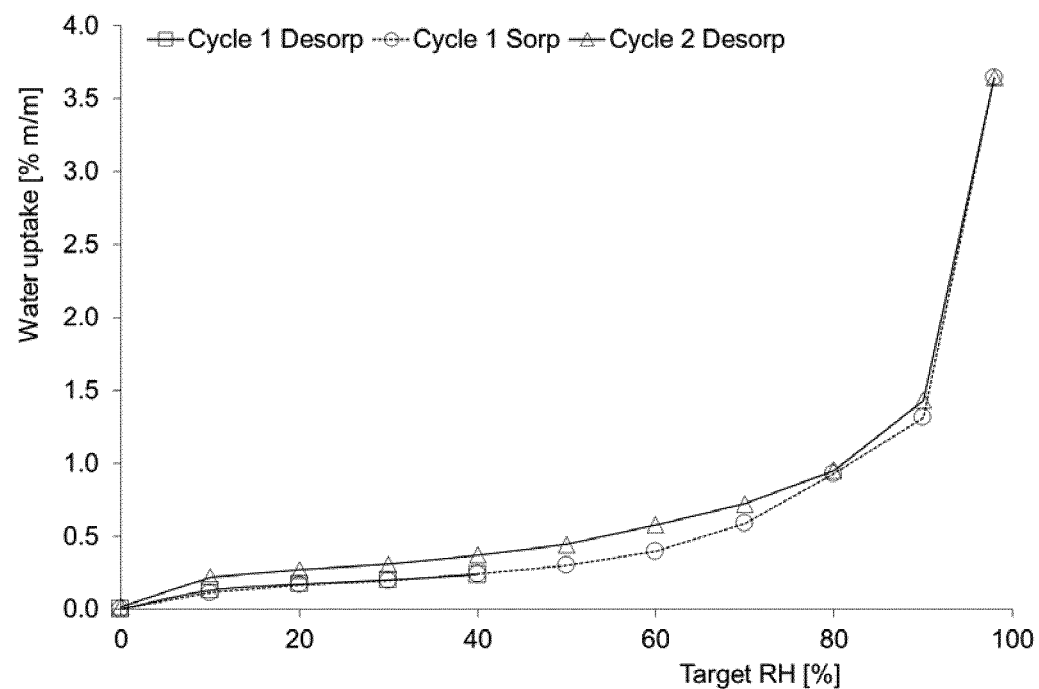
FIG. 36: Water Vapour Sorption Isotherm (25° C.) of Maleate salt form Maleate-NF1.

In another embodiment, form Maleate-NF1 is characterized by a diffraction pattern substantially similar to that of FIG. 33.

A Powder X-Ray Diffraction pattern of free base form Maleate-NF1 was obtained by standard techniques as described in the European Pharmacopeia 6$^{th}$ Edition chapter 2.9.33, and was characterised by the following X-ray powder diffractogram (monochromatic Cu-K$\alpha_1$ radiation, $\lambda$=1.5406 Å, Stoe StadiP 611 KL transmission diffractometer).

In another embodiment, form Maleate-NF1 is characterized as a crystalline anhydrous form.

Other physical properties of form Maleate-NF1 include the following: Thermal behaviour of Maleate salt form Maleate-NF1 showed a melting peak onset at approx. 139° C. Thermogravimetric analysis revealed a low weight loss of approx. 0.7% m/m up to this temperature. DSC and TGA profiles are displayed in the figures. DSC scan of Maleate salt form Maleate-NF1 was acquired on a Mettler-Toledo DSC 821e with a heating rate of 5 K/min, using nitrogen purge gas at 50 mL/min. TGA scan of Maleate salt form Maleate-NF1 was acquired on a Mettler-Toledo TGA 851 with a heating rate of 5 K/min, using nitrogen purge gas at 50 mL/min. Water Vapour Sorption behaviour of Maleate salt form Maleate-NF1 revealed small water uptake levels ≤1% m/m in the relative humidity (rh) range 0-80% rh, and slightly elevated water uptake levels ≤5% m/m in the relative humidity (rh) range 90-98% rh. Maleate salt form Maleate-NF1 can be classified as slightly hygroscopic acc. to Ph. Eur. Criteria (section 5.11.). Water Vapor Sorption isotherm (25° C.) of Maleate salt form Maleate-NF1 is displayed in the figures. Water Vapour Sorption isotherm was acquired on a DVS-Intrinsic system from SMS. Overall, Maleate salt form Maleate-NF1 revealed good solid-state properties (good crystallinity, slightly hygroscopic, high thermal stability).

In one embodiment, the invention provides for Compound 1 characterized as maleate form Maleate-NF2.

In certain embodiments, form Maleate-NF2 is characterized by one or more 2θ peaks at 10.8, 17.1, 19.2, and 20.7 degrees. In certain embodiments, form Maleate-NF2 is characterized by two or more 2θ peaks at 10.8, 17.1, 19.2, and 20.7 degrees. In certain embodiments, form Maleate-NF2 is characterized by 2θ peaks at 10.8, 17.1, 19.2, and 20.7 degrees.

In certain embodiments, form Maleate-NF2 is characterized by one or more 2θ peaks at 8.5, 10.8, 17.1, 18.1, 18.5, 19.2, 20.7, 21.7, and 23.2 degrees. In certain embodiments, form Maleate-NF2 is characterized by two or more 2θ peaks at 8.5, 10.8, 17.1, 18.1, 18.5, 19.2, 20.7, 21.7, and 23.2 degrees. In certain embodiments, form Maleate-NF2 is characterized by three or more 2θ peaks 8.5, 10.8, 17.1, 18.1, 18.5, 19.2, 20.7, 21.7, and 23.2 degrees. In certain embodiments, form Maleate-NF2 is characterized by four or more 2θ peaks at 8.5, 10.8, 17.1, 18.1, 18.5, 19.2, 20.7, 21.7, and 23.2 degrees. In certain embodiments, form Maleate-NF2 is characterized by five or more 2θ peaks at 8.5, 10.8, 17.1, 18.1, 18.5, 19.2, 20.7, 21.7, and 23.2 degrees. In certain embodiments, form Maleate-NF2 is characterized by six or more 2θ peaks at 8.5, 10.8, 17.1, 18.1, 18.5, 19.2, 20.7, 21.7, and 23.2 degrees. In certain embodiments, form Maleate-NF2 is characterized by seven or more 2θ peaks at 8.5, 10.8, 17.1, 18.1, 18.5, 19.2, 20.7, 21.7, and 23.2 degrees. In certain embodiments, form Maleate-NF2 is characterized by 2θ peaks at 8.5, 10.8, 17.1, 18.1, 18.5, 19.2, 20.7, 21.7, and 23.2 degrees.

In certain embodiments, form Maleate-NF2 is characterized by 2θ peaks at

| No. | °2θ (Cu-K$\alpha_1$ radiation) ± 0.2° |
|---|---|
| 1 | 6.8 |
| 2 | 8.5 |
| 3 | 9.2 |
| 4 | 10.8 |
| 5 | 11.3 |
| 6 | 13.6 |
| 7 | 14.6 |
| 8 | 16.4 |
| 9 | 17.1 |
| 10 | 18.1 |
| 11 | 18.5 |
| 12 | 19.2 |
| 13 | 19.7 |
| 14 | 20.1 |
| 15 | 20.7 |
| 16 | 21.7 |
| 17 | 22.1 |
| 18 | 22.7 |
| 19 | 23.2 |
| 20 | 24.1 |
| 21 | 24.4 |

Figure 37:
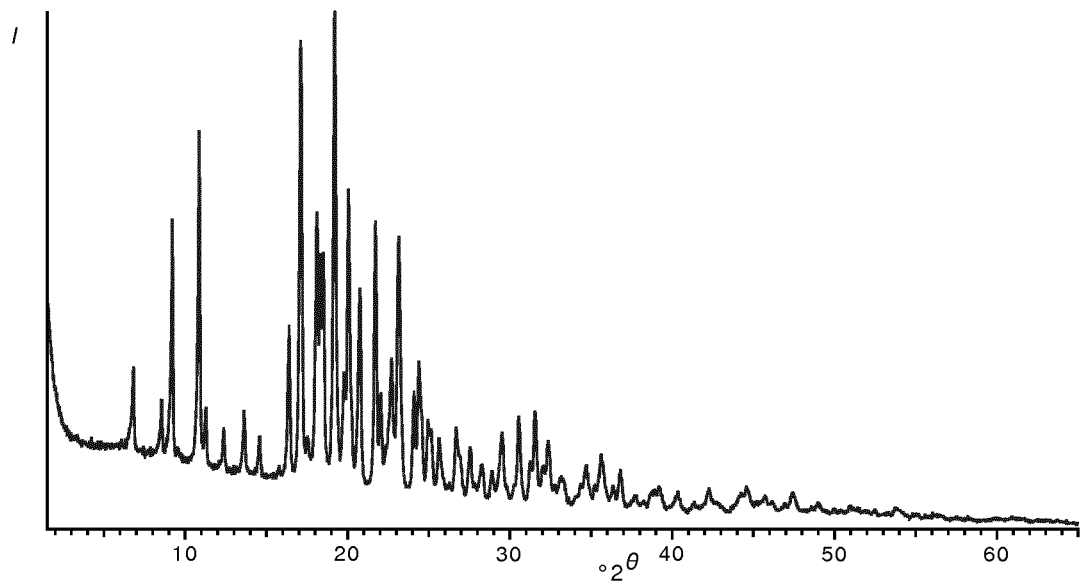
FIG. 37: Powder X-ray diffractogram of Maleate salt form Maleate-NF2.

In another embodiment, form Maleate-NF2 is characterized by a diffraction pattern substantially similar to that of FIG. 37.

A Powder X-Ray Diffraction pattern of free base form Maleate-NF2 was obtained by standard techniques as described in the European Pharmacopeia 6$^{th}$ Edition chapter 2.9.33, and was characterised by the following X-ray powder diffractogram (monochromatic Cu-K$\alpha_1$ radiation, $\lambda$=1.5406 Å, Stoe StadiP 611 KL transmission diffractometer).

In another embodiment, form Maleate-NF2 is characterized as a crystalline form.

In one embodiment, the invention provides for Compound 1 characterized as fumarate form Fumarate-NF1.

In certain embodiments, form Fumarate-NF1 is characterized by one or more 2θ peaks at 9.0, 17.0, 18.4, and 22.1 degrees. In certain embodiments, form Fumarate-NF1 is characterized by two or more 2θ peaks at 9.0, 17.0, 18.4, and 22.1 degrees. In certain embodiments, form Fumarate-NF1 is characterized by 2θ peaks at 9.0, 17.0, 18.4, and 22.1 degrees.

In certain embodiments, form Fumarate-NF1 is characterized by one or more 2θ peaks at 9.0, 16.7, 17.0, 18.4, 18.7, 20.9, and 22.1 degrees. In certain embodiments, form Fumarate-NF1 is characterized by two or more 2θ peaks at 9.0, 16.7, 17.0, 18.4, 18.7, 20.9, and 22.1 degrees. In certain embodiments, form Fumarate-NF1 is characterized by three or more 2θ peaks 9.0, 16.7, 17.0, 18.4, 18.7, 20.9, and 22.1 degrees. In certain embodiments, form Fumarate-NF1 is characterized by four or more 2θ peaks at 9.0, 16.7, 17.0, 18.4, 18.7, 20.9, and 22.1 degrees. In certain embodiments, form Fumarate-NF1 is characterized by five or more 2θ peaks at 9.0, 16.7, 17.0, 18.4, 18.7, 20.9, and 22.1 degrees. In certain embodiments, form Fumarate-NF1 is characterized by 2θ peaks at 9.0, 16.7, 17.0, 18.4, 18.7, 20.9, and 22.1 degrees.

In certain embodiments, form Fumarate-NF1 is characterized by 2θ peaks at

| No. | °2θ (Cu-K$\alpha_1$ radiation) ± 0.2° |
|---|---|
| 1 | 8.1 |
| 2 | 9 |

-continued

| No. | °2θ (Cu-Kα₁ radiation) ± 0.2° |
|---|---|
| 3 | 13.4 |
| 4 | 14.2 |
| 5 | 15.4 |
| 6 | 16.3 |
| 7 | 16.7 |
| 8 | 17 |
| 9 | 18.4 |
| 10 | 18.7 |
| 11 | 19.2 |
| 12 | 20.3 |
| 13 | 20.6 |
| 14 | 20.9 |
| 15 | 21.2 |
| 16 | 21.5 |
| 17 | 21.8 |
| 18 | 22.1 |
| 19 | 22.5 |
| 20 | 23.7 |
| 21 | 24.3 |

Figure 38:
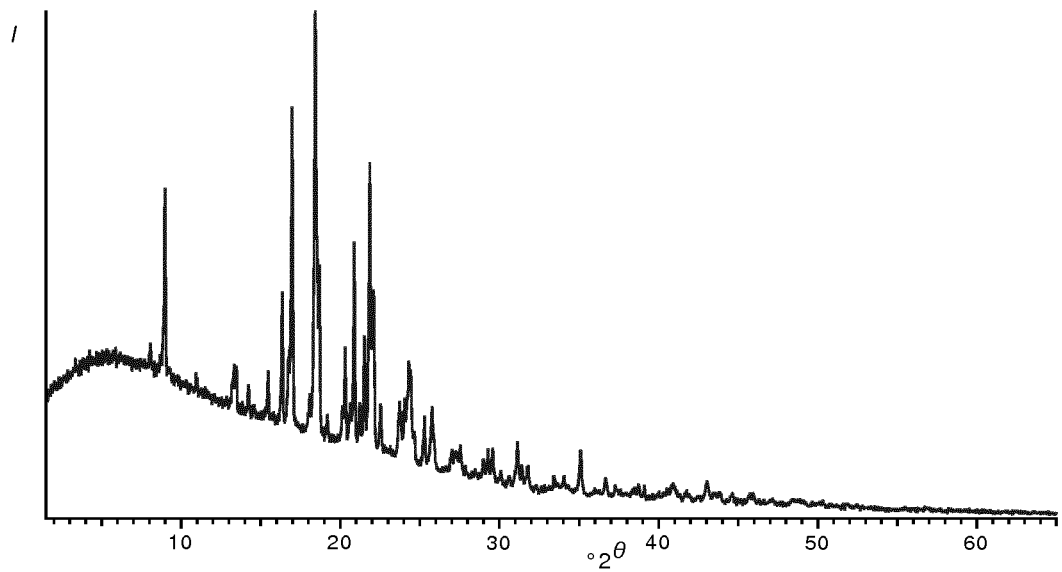
FIG. 38: Powder X-ray diffractogram of Fumarate salt form Fumarate-NF1.
Figure 39:
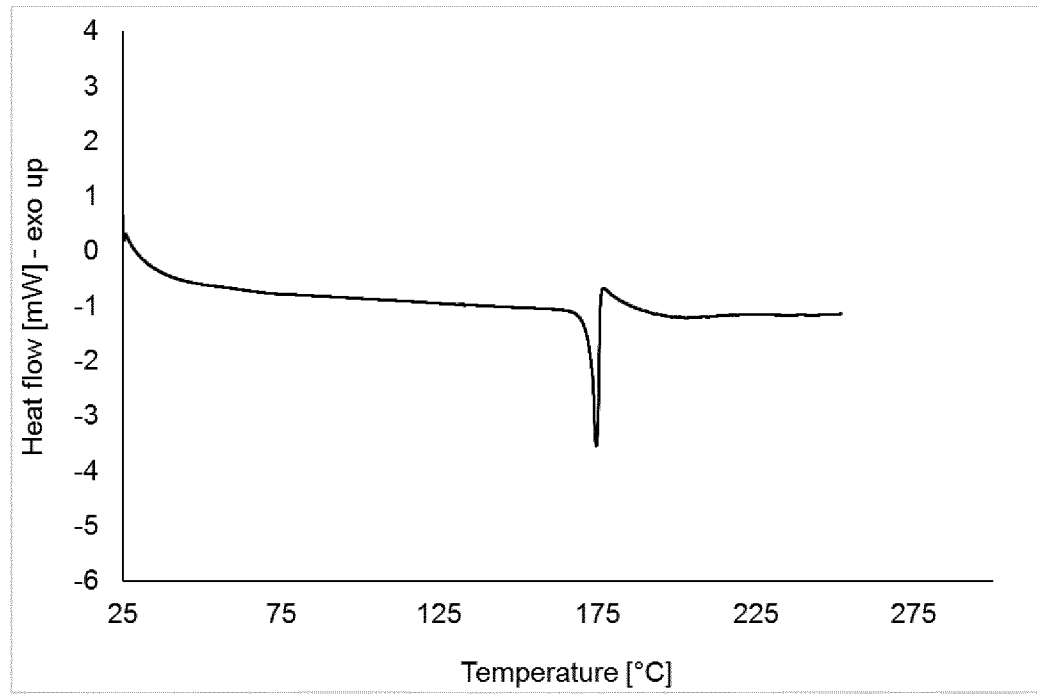
FIG. 39: DSC scan of Fumarate salt form Fumarate-NF1 (5 K/min).
Figure 40:
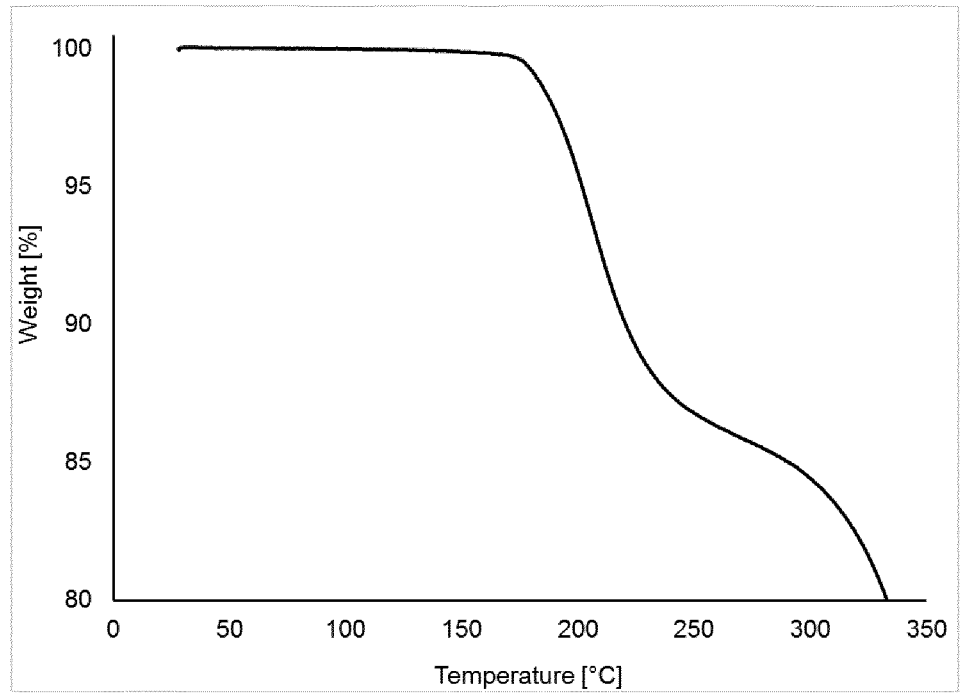
FIG. 40: TGA scan of Fumarate salt form Fumarate-NF1 (5 K/min).
Figure 41:
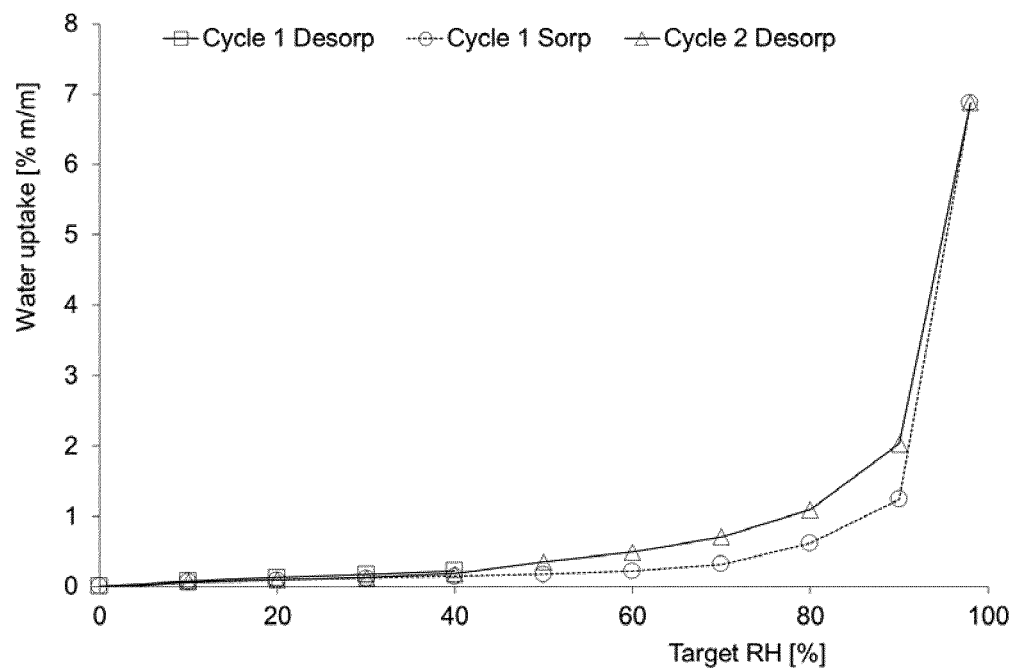
FIG. 41: Water Vapour Sorption Isotherm (25° C.) of Fumarate salt form Fumarate-NF1.

In another embodiment, form Fumarate-NF1 is characterized by a diffraction pattern substantially similar to that of FIG. 38.

A Powder X-Ray Diffraction pattern of free base form Fumarate-NF1 was obtained by standard techniques as described in the European Pharmacopeia 6$^{th}$ Edition chapter 2.9.33, and was characterised by the following X-ray powder diffractogram (monochromatic Cu-Kα₁ radiation, λ=1.5406 Å, Stoe StadiP 611 KL transmission diffractometer).

In another embodiment, form Fumarate-NF1 is characterized as a crystalline anhydrous form.

Other physical properties of form Fumarate-NF1 include the following: Thermal behaviour of Fumarate salt form Fumarate-NF1 showed a melting peak onset at approx. 173° C. Thermogravimetric analysis revealed a low weight loss of approx. 0.3% m/m up to this temperature. DSC and TGA profiles are displayed in the figures. DSC scan of Fumarate salt form Fumarate-NF1 was acquired on a Mettler-Toledo DSC 821e with a heating rate of 5 K/min, using nitrogen purge gas at 50 mL/min. TGA scan of Fumarate salt form Fumarate-NF1 was acquired on a Mettler-Toledo TGA 851 with a heating rate of 5 K/min, using nitrogen purge gas at 50 mL/min. Water Vapour Sorption behaviour of Fumarate salt form Fumarate-NF1 revealed small water uptake levels ≤1% m/m in the relative humidity (rh) range 0-80% rh, and elevated water uptake levels ≥5% m/m in the relative humidity (rh) range 90-98% rh. Fumarate salt form Fumarate-NF1 can be classified as slightly hygroscopic acc. to Ph. Eur. Criteria (section 5.11.). Water Vapor Sorption isotherm (25° C.) of Fumarate salt form Fumarate-NF1 is displayed in the figures. Water Vapour Sorption isotherm was acquired on a DVS-Intrinsic system from SMS. Dissolution level of Fumarate salt form Fumarate-NF1 in Fasted-State Simulated Intestinal Fluid [FaSSIF, pH 6.5] at 37° C. was determined to be approx. 27 μg/mL after 2 h (see example 7). Overall, Fumarate salt form Fumarate-NF1 revealed good solid-state properties (good crystallinity, slightly hygroscopic, high thermal stability).

In one embodiment, the invention provides for Compound 1 characterized as fumarate form Fumarate-NF2.

In certain embodiments, form Fumarate-NF2 is characterized by one or more 2θ peaks at 18.4, 19.2, and 20.3 degrees. In certain embodiments, form Fumarate-NF2 is characterized by two or more 2θ peaks at 18.4, 19.2, and 20.3 degrees. In certain embodiments, form Fumarate-NF2 is characterized by 2θ peaks at 18.4, 19.2, and 20.3 degrees.

In certain embodiments, form Fumarate-NF2 is characterized by one or more 2θ peaks at 9.6, 10.6, 13.9, 14.9, 18.4, 19.2, and 20.3 degrees. In certain embodiments, form Fumarate-NF2 is characterized by two or more 2θ peaks at 9.6, 10.6, 13.9, 14.9, 18.4, 19.2, and 20.3 degrees. In certain embodiments, form Fumarate-NF2 is characterized by three or more 2θ peaks at 9.6, 10.6, 13.9, 14.9, 18.4, 19.2, and 20.3 degrees. In certain embodiments, form Fumarate-NF2 is characterized by four or more 2θ peaks at 9.6, 10.6, 13.9, 14.9, 18.4, 19.2, and 20.3 degrees. In certain embodiments, form Fumarate-NF2 is characterized by five or more 2θ peaks at 9.6, 10.6, 13.9, 14.9, 18.4, 19.2, and 20.3 degrees. In certain embodiments, form Fumarate-NF2 is characterized by 2θ peaks at 9.6, 10.6, 13.9, 14.9, 18.4, 19.2, and 20.3 degrees.

In certain embodiments, form Fumarate-NF2 is characterized by 2θ peaks at

| No. | °2θ (Cu-Kα₁ radiation) ± 0.2° |
|---|---|
| 1 | 9.2 |
| 2 | 9.6 |
| 3 | 10.6 |
| 4 | 12.6 |
| 5 | 13.9 |
| 6 | 14.9 |
| 7 | 16.3 |
| 8 | 17 |
| 9 | 17.4 |
| 10 | 18.4 |
| 11 | 19.2 |
| 12 | 20.3 |
| 13 | 20.9 |
| 14 | 21.9 |
| 15 | 22.7 |
| 16 | 23.4 |
| 17 | 23.8 |
| 18 | 25 |
| 19 | 27.9 |

Figure 42:
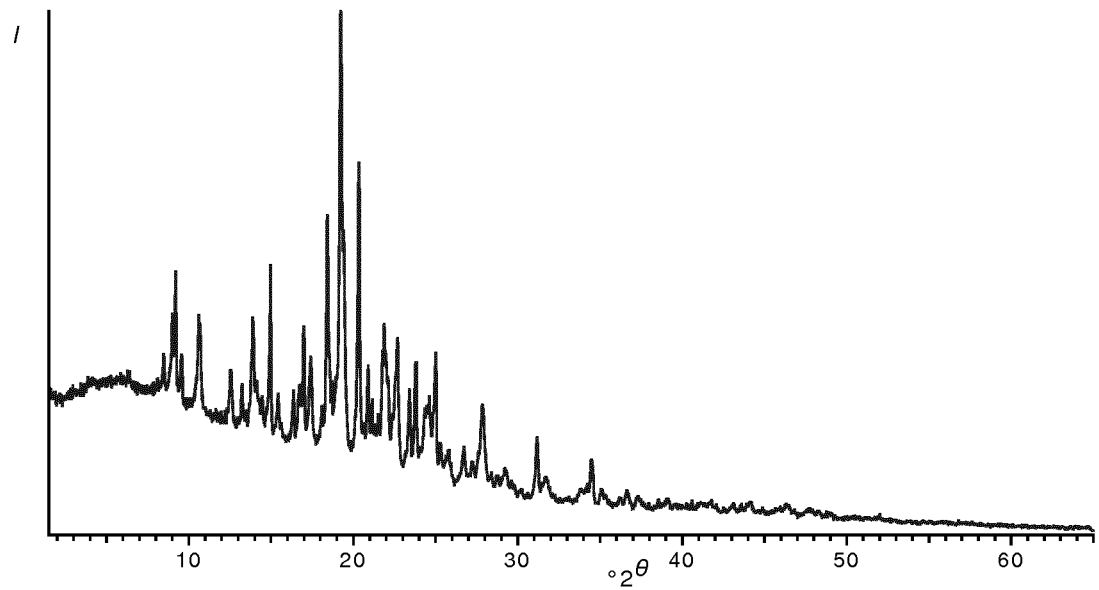
FIG. 42: Powder X-ray diffractogram of Fumarate salt form Fumarate-NF2.
Figure 43:
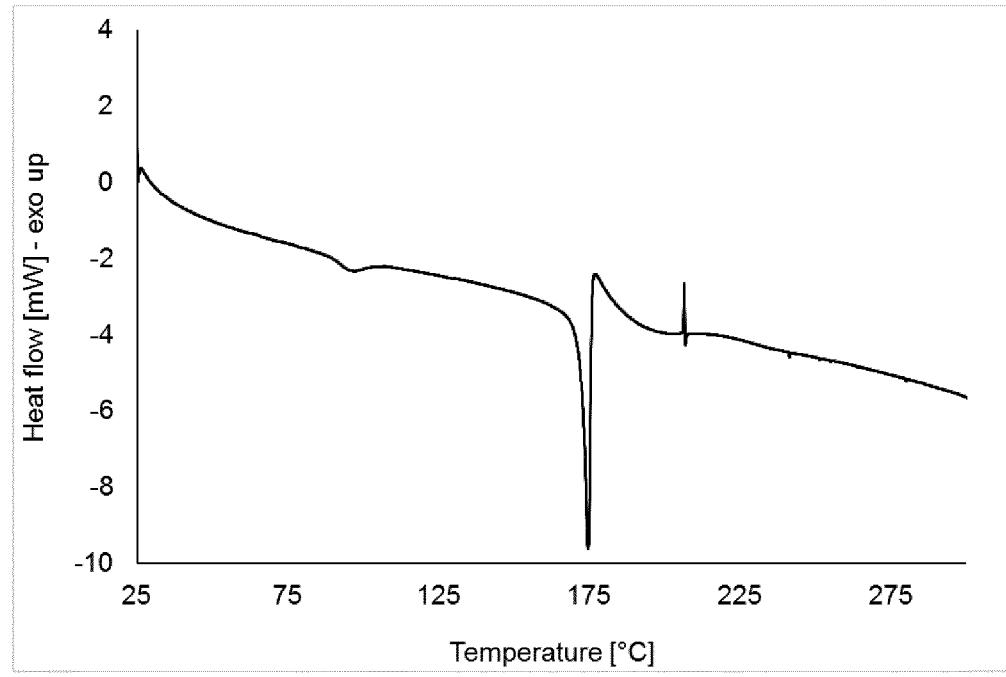
FIG. 43: DSC scan of Fumarate salt form Fumarate-NF2 (5 K/min).
Figure 44:
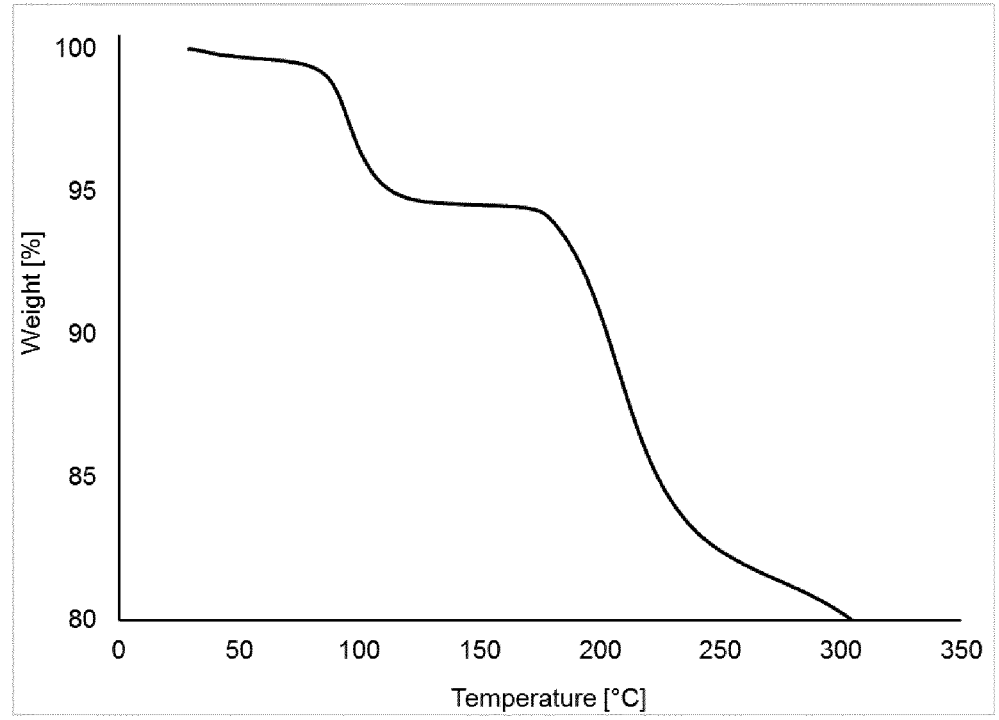
FIG. 44: TGA scan of Fumarate salt form Fumarate-NF2 (5 K/min).

In another embodiment, form Fumarate-NF2 is characterized by a diffraction pattern substantially similar to that of FIG. 42.

A Powder X-Ray Diffraction pattern of free base form Fumarate-NF2 was obtained by standard techniques as described in the European Pharmacopeia 6$^{th}$ Edition chapter 2.9.33, and was characterised by the following X-ray powder diffractogram (monochromatic Cu-Kα₁ radiation, λ=1.5406 Å, Stoe StadiP 611 KL transmission diffractometer).

In another embodiment, form Fumarate-NF2 is characterized as a crystalline solvate form.

Other physical properties of form Fumarate-NF2 include the following: Thermal behaviour of Fumarate salt form Fumarate-NF2 showed a phase transition at approx. 90° C. to Fumarate salt form Fumarate-NF1 and a melting peak onset at approx. 172° C. of Fumarate salt form Fumarate-NF1. Thermogravimetric analysis revealed a weight loss of approx. 6% m/m up to this temperature. DSC and TGA profiles are displayed in the figures. DSC scan of Fumarate salt form Fumarate-NF2 was acquired on a Mettler-Toledo DSC 821e with a heating rate of 5 K/min, using nitrogen purge gas at 50 mL/min. TGA scan of Fumarate salt form Fumarate-NF2 was acquired on a Mettler-Toledo TGA 851 with a heating rate of 5 K/min, using nitrogen purge gas at 50 mL/min. Overall, Fumarate salt form Fumarate-NF2 revealed good solid-state properties (good crystallinity, thermal stability).

In one embodiment, the invention provides for Compound 1 characterized as fumarate form Fumarate-NF3.

In certain embodiments, form Fumarate-NF3 is characterized by one or more 2θ peaks at 6.9, 10.3, 17.4, and 21.1 degrees. In certain embodiments, form Fumarate-NF3 is characterized by two or more 2θ peaks at 6.9, 10.3, 17.4, and 21.1 degrees. In certain embodiments, form Fumarate-NF3 is characterized by 2θ peaks at 6.9, 10.3, 17.4, and 21.1 degrees.

In certain embodiments, form Fumarate-NF3 is characterized by one or more 2θ peaks at 6.9, 10.3, 17.4, 21.1, 21.4, and 25.7 degrees. In certain embodiments, form Fumarate-NF3 is characterized by two or more 2θ peaks at 6.9, 10.3, 17.4, 21.1, 21.4, and 25.7 degrees. In certain embodiments, form Fumarate-NF3 is characterized by three or more 2θ peaks 6.9, 10.3, 17.4, 21.1, 21.4, and 25.7 degrees. In certain embodiments, form Fumarate-NF3 is characterized by four or more 2θ peaks at 96.9, 10.3, 17.4, 21.1, 21.4, and 25.7 degrees. In certain embodiments, form Fumarate-NF3 is characterized by five or more 2θ peaks at 6.9, 10.3, 17.4, 21.1, 21.4, and 25.7 degrees. In certain embodiments, form Fumarate-NF3 is characterized by 2θ peaks at 6.9, 10.3, 17.4, 21.1, 21.4, and 25.7 degrees.

In certain embodiments, form Fumarate-NF3 is characterized by 2θ peaks at

| No. | °2θ (Cu-Kα$_1$ radiation) ± 0.2° |
|---|---|
| 1 | 6.9 |
| 2 | 8.5 |
| 3 | 10.3 |
| 4 | 11 |
| 5 | 11.3 |
| 6 | 14 |
| 7 | 15.8 |
| 8 | 16.8 |
| 9 | 17.2 |
| 10 | 17.4 |
| 11 | 17.7 |
| 12 | 19.3 |
| 13 | 19.6 |
| 14 | 19.9 |
| 15 | 20.2 |
| 16 | 20.7 |
| 17 | 21.1 |
| 18 | 21.4 |
| 19 | 21.8 |
| 20 | 23.4 |
| 21 | 25.7 |

Figure 45:
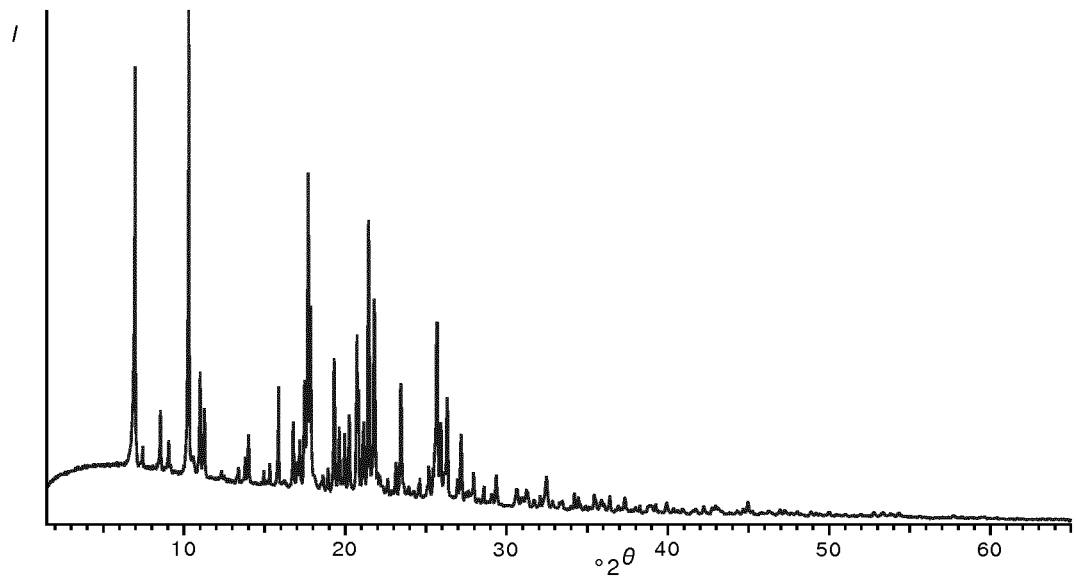
FIG. 45: Powder X-ray diffractogram of Fumarate salt form Fumarate-NF3.
Figure 46:
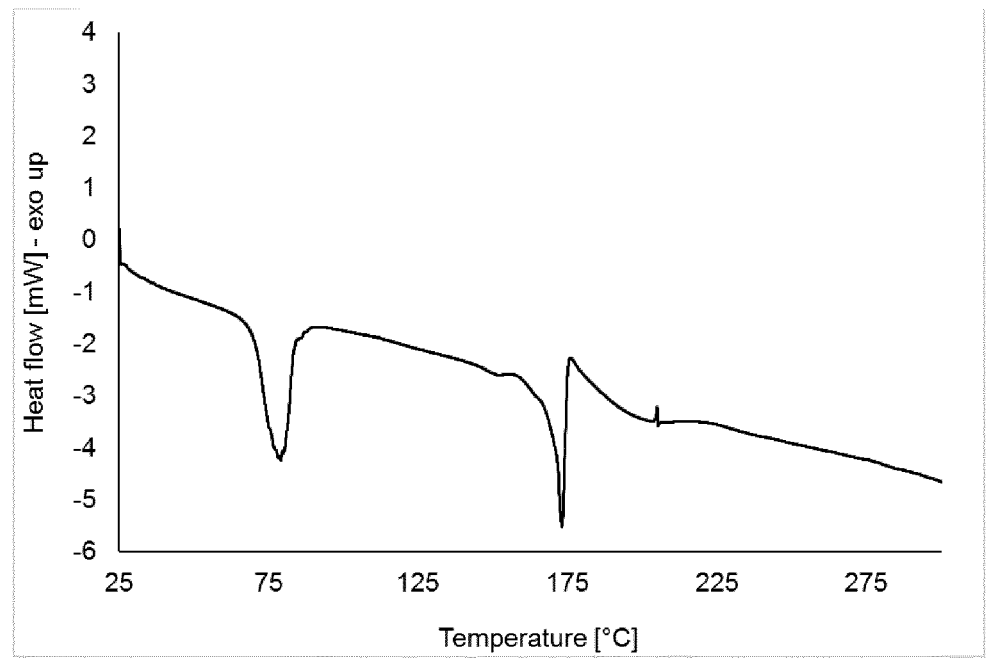
FIG. 46: DSC scan of Fumarate salt form Fumarate-NF3 (5 K/min).
Figure 47:
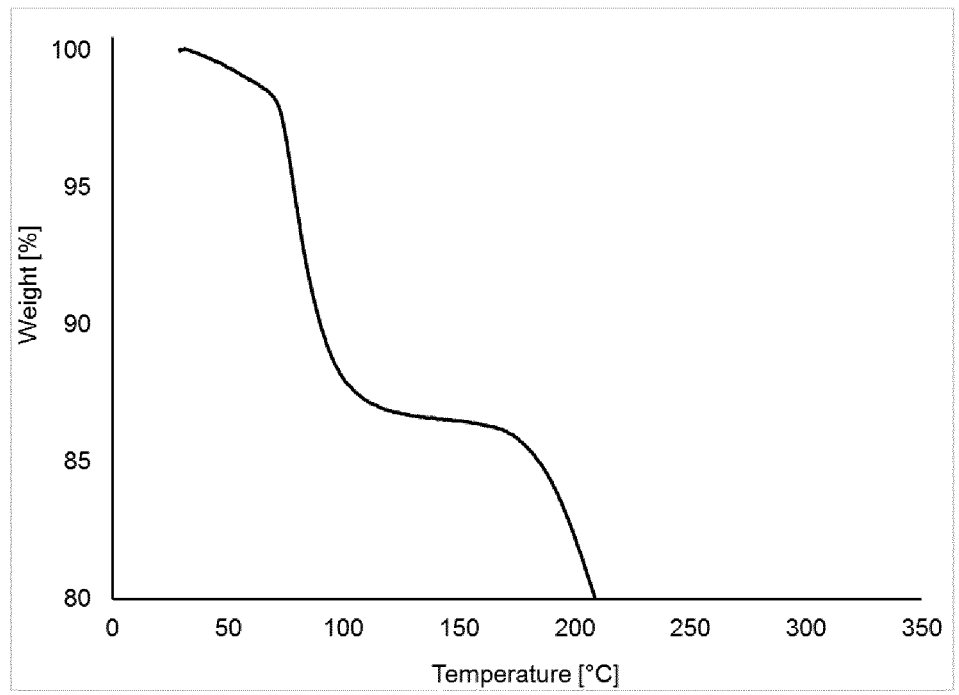
FIG. 47: TGA scan of Fumarate salt form Fumarate-NF3 (5 K/min).

In another embodiment, form Fumarate-NF3 is characterized by a diffraction pattern substantially similar to that of FIG. 45.

A Powder X-Ray Diffraction pattern of free base form Fumarate-NF3 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form Fumarate-NF3 is characterized as a crystalline solvate form.

Other physical properties of form Fumarate-NF3 include the following: Thermal behaviour of Fumarate salt form Fumarate-NF3 showed a phase transition at approx. 70° C. to Fumarate salt form Fumarate-NF1 and a melting peak onset at approx. 170° C. of Fumarate salt form Fumarate-NF1. Thermogravimetric analysis revealed a weight loss of approx. 14% m/m up to this temperature. DSC and TGA profiles are displayed in the figures. DSC scan of Fumarate salt form Fumarate-NF3 was acquired on a Mettler-Toledo DSC 821e with a heating rate of 5 K/min, using nitrogen purge gas at 50 mL/min. TGA scan of Fumarate salt form Fumarate-NF3 was acquired on a Mettler-Toledo TGA 851 with a heating rate of 5 K/min, using nitrogen purge gas at 50 mL/min. Overall, Fumarate salt form Fumarate-NF3 revealed good solid-state properties (good crystallinity, thermal stability).

In one embodiment, the invention provides for Compound 1 characterized as fumarate form Fumarate-NF4.

In certain embodiments, form Fumarate-NF4 is characterized by one or more 2θ peaks at 7.9, 15.8, 18.4, and 19.4 degrees. In certain embodiments, form Fumarate-NF4 is characterized by two or more 2θ peaks at 7.9, 15.8, 18.4, and 19.4 degrees. In certain embodiments, form Fumarate-NF4 is characterized by 2θ peaks at 7.9, 15.8, 18.4, and 19.4 degrees.

In certain embodiments, form Fumarate-NF4 is characterized by one or more 2θ peaks at 7.9, 8.9, 11.7, 12.9, 15.8, 18.4, 19.4, and 21.8 degrees. In certain embodiments, form Fumarate-NF4 is characterized by two or more 2θ peaks at 7.9, 8.9, 11.7, 12.9, 15.8, 18.4, 19.4, and 21.8 degrees. In certain embodiments, form Fumarate-NF4 is characterized by three or more 2θ peaks 7.9, 8.9, 11.7, 12.9, 15.8, 18.4, 19.4, and 21.8 degrees. In certain embodiments, form Fumarate-NF4 is characterized by four or more 2θ peaks at 7.9, 8.9, 11.7, 12.9, 15.8, 18.4, 19.4, and 21.8 degrees. In certain embodiments, form Fumarate-NF4 is characterized by five or more 2θ peaks at 7.9, 8.9, 11.7, 12.9, 15.8, 18.4, 19.4, and 21.8 degrees. In certain embodiments, form Fumarate-NF4 is characterized by 2θ peaks at 7.9, 8.9, 11.7, 12.9, 15.8, 18.4, 19.4, and 21.8 degrees.

In certain embodiments, form Fumarate-NF4 is characterized by 2θ peaks at

| No. | °2θ (Cu-Kα$_1$ radiation) ± 0.2° |
|---|---|
| 1 | 7.9 |
| 2 | 8.9 |
| 3 | 11.7 |
| 4 | 12.9 |
| 5 | 14.8 |
| 6 | 15.8 |
| 7 | 16.9 |
| 8 | 17.9 |
| 9 | 18.4 |
| 10 | 19.4 |
| 11 | 20.4 |
| 12 | 20.9 |
| 13 | 21.8 |
| 14 | 22.2 |
| 15 | 22.7 |
| 16 | 23.4 |
| 17 | 26.2 |
| 18 | 28 |
| 19 | 28.8 |

Figure 48:
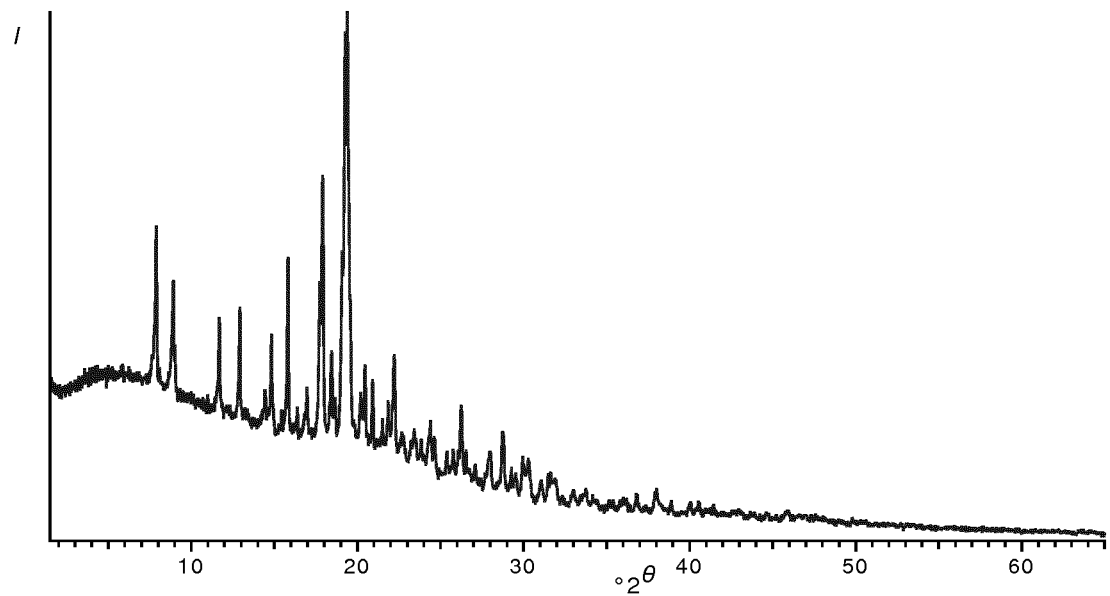
FIG. 48: Powder X-ray diffractogram of Fumarate salt form Fumarate-NF4.
Figure 49:
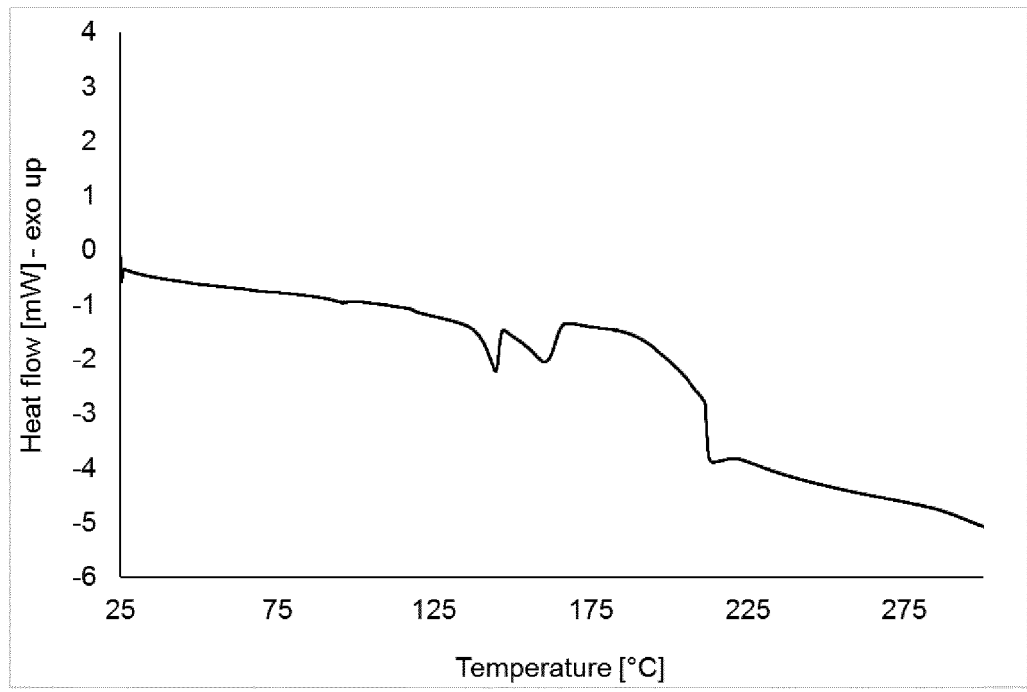
FIG. 49: DSC scan of Fumarate salt form Fumarate-NF4 (5 K/min).
Figure 50:
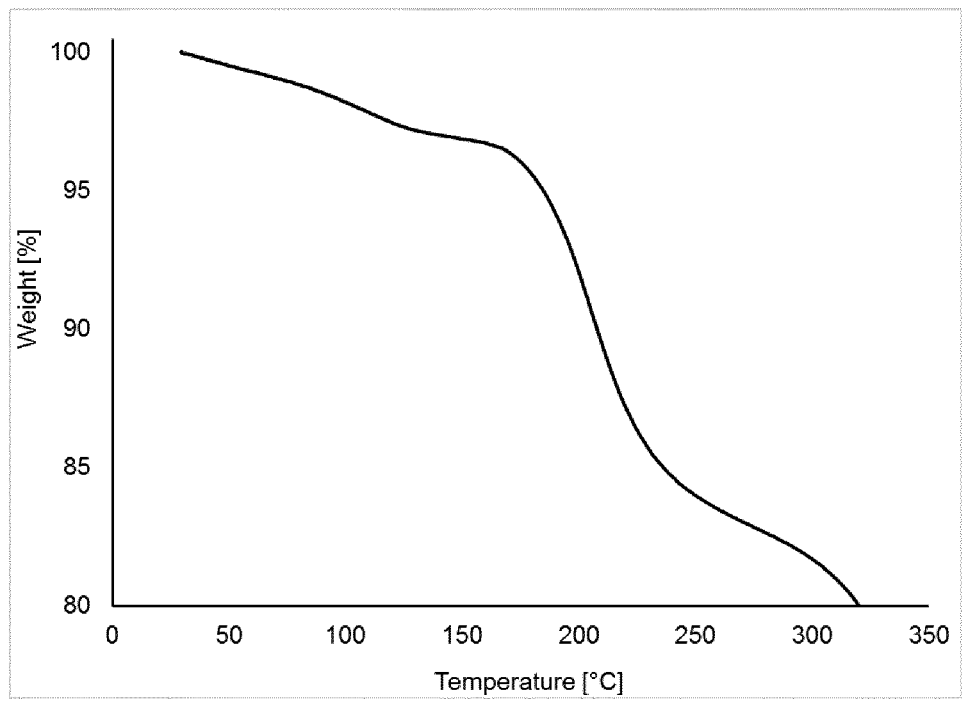
FIG. 50: TGA scan of Fumarate salt form Fumarate-NF4 (5 K/min)

In another embodiment, form Fumarate-NF4 is characterized by a diffraction pattern substantially similar to that of FIG. 48.

A Powder X-Ray Diffraction pattern of free base form Fumarate-NF4 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form Fumarate-NF4 is characterized as a crystalline solvate form.

Other physical properties of form Fumarate-NF4 include the following: Thermal behaviour of Fumarate salt form Fumarate-NF4 showed a melting peak onset at approx. 140° C. Thermogravimetric analysis revealed a low weight loss of approx. 3% m/m up to this temperature. DSC and TGA profiles are displayed in the figures. DSC scan of Fumarate salt form Fumarate-NF4 was acquired on a Mettler-Toledo DSC 821e with a heating rate of 5 K/min, using nitrogen purge gas at 50 mL/min. TGA scan of Fumarate salt form Fumarate-NF4 was acquired on a Mettler-Toledo TGA 851 with a heating rate of 5 K/min, using nitrogen purge gas at 50 mL/min. Overall, Fumarate salt form Fumarate-NF4 revealed good solid-state properties (good crystallinity, high thermal stability).

In one embodiment, the invention provides for Compound 1 characterized as fumarate form Fumarate-NF5.

In certain embodiments, form Fumarate-NF5 is characterized by one or more 2θ peaks at 16.0, 19.8, 22.2, and 23.4 degrees. In certain embodiments, form Fumarate-NF5 is characterized by two or more 2θ peaks at 16.0, 19.8, 22.2, and 23.4 degrees. In certain embodiments, form Fumarate-NF5 is characterized by 2θ peaks at 16.0, 19.8, 22.2, and 23.4 degrees.

In certain embodiments, form Fumarate-NF5 is characterized by 2θ peaks at

| No. | °2θ (Cu-Kα$_1$ radiation) ± 0.2° |
|---|---|
| 1 | 8.4 |
| 2 | 11.2 |
| 3 | 16.0 |
| 4 | 19.8 |
| 5 | 22.2 |
| 6 | 23.4 |
| 7 | 28.0 |
| 8 | 28.5 |

Figure 51:
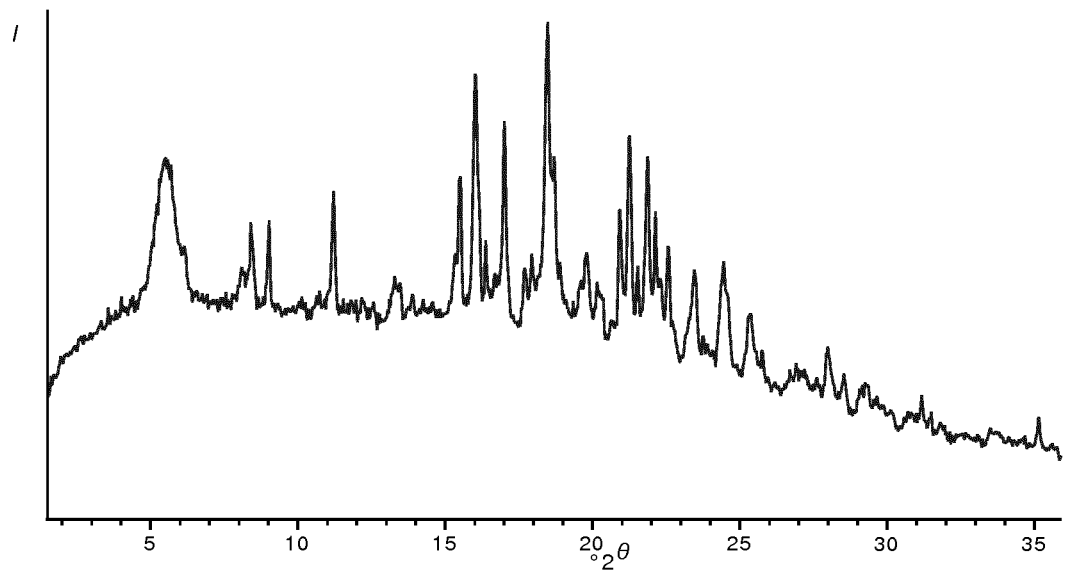
FIG. 51: Powder X-ray diffractogram of Fumarate salt form Fumarate-NF5.
Figure 52:
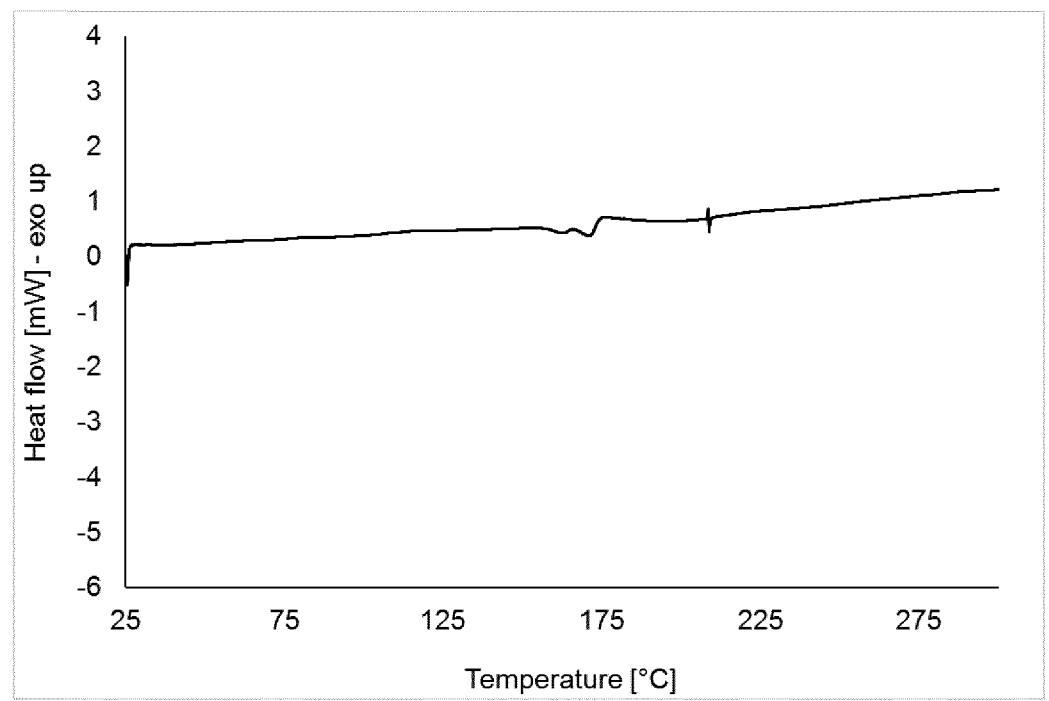
FIG. 52: DSC scan of Fumarate salt form Fumarate-NF5 (5 K/min).
Figure 53:
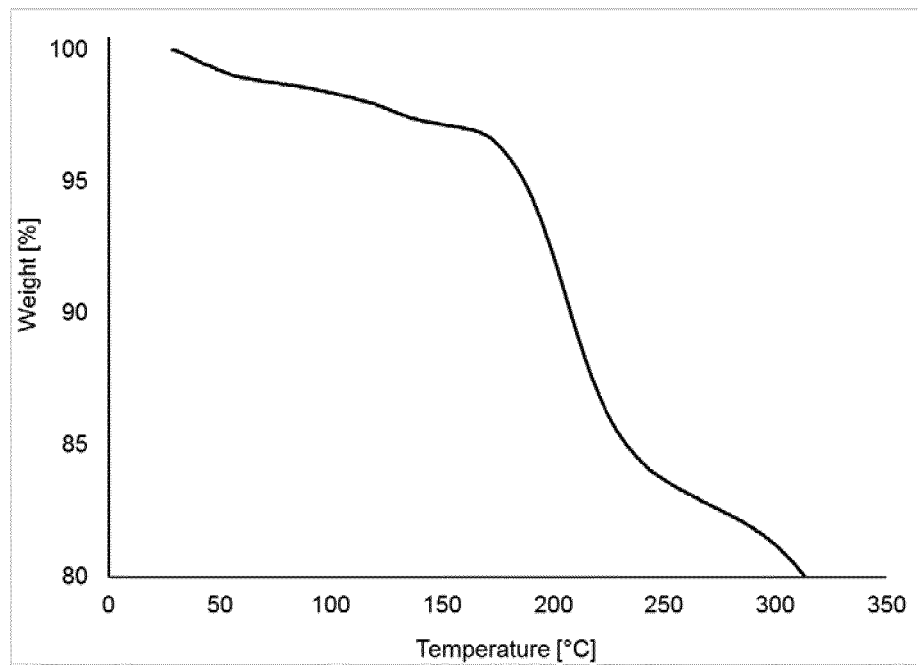
FIG. 53: TGA scan of Fumarate salt form Fumarate-NF5 (5 K/min).

In another embodiment, form Fumarate-NF5 is characterized by a diffraction pattern substantially similar to that of FIG. 51.

A Powder X-Ray Diffraction pattern of free base form Fumarate-NF5 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form Fumarate-NF5 is characterized as a crystalline form.

Other physical properties of form Fumarate-NF5 include the following: Thermal behaviour of Fumarate salt form Fumarate-NF5 showed a melting peak onset at approx. 158° C. Thermogravimetric analysis revealed a low weight loss of approx. 3% m/m up to this temperature. DSC and TGA profiles are displayed in the figures. DSC scan of Fumarate salt form Fumarate-NF5 was acquired on a Mettler-Toledo DSC 821e with a heating rate of 5 K/min, using nitrogen purge gas at 50 mL/min. TGA scan of Fumarate salt form Fumarate-NF5 was acquired on a Mettler-Toledo TGA 851 with a heating rate of 5 K/min, using nitrogen purge gas at 50 mL/min. Overall, Fumarate salt form Fumarate-NF5 revealed good solid-state properties (crystallinity, high thermal stability).

In one embodiment, the invention provides for Compound 1 characterized as mesylate salt form Mesylate-NF1.

In certain embodiments, form Mesylate-NF1 is characterized by one or more 2θ peaks at 18.7, 19.5, and 21.1 degrees. In certain embodiments, form Mesylate-NF1 is characterized by two or more 2θ peaks at 18.7, 19.5, and 21.1 degrees. In certain embodiments, form Mesylate-NF1 is characterized by 2θ peaks at 18.7, 19.5, and 21.1 degrees.

In certain embodiments, form Mesylate-NF1 is characterized by one or more 2θ peaks at 11.2, 12.4, 13.1, 18.7, 19.5, and 21.1 degrees. In certain embodiments, form Mesylate-NF1 is characterized by two or more 2θ peaks at 11.2, 12.4, 13.1, 18.7, 19.5, and 21.1 degrees. In certain embodiments, form Mesylate-NF1 is characterized by three or more 2θ peaks 11.2, 12.4, 13.1, 18.7, 19.5, and 21.1 degrees. In certain embodiments, form Mesylate-NF1 is characterized by four or more 2θ peaks at 11.2, 12.4, 13.1, 18.7, 19.5, and 21.17 degrees. In certain embodiments, form Mesylate-NF1 is characterized by 2θ peaks at 11.2, 12.4, 13.1, 18.7, 19.5, and 21.1 degrees.

In certain embodiments, form Mesylate-NF1 is characterized by 2θ peaks at

| No. | °2θ (Cu-Kα$_1$ radiation) ± 0.2° |
|---|---|
| 1 | 6.2 |
| 2 | 11.2 |
| 3 | 12.4 |
| 4 | 13.1 |
| 5 | 14.4 |
| 6 | 16.5 |
| 7 | 16.7 |
| 8 | 17.5 |
| 9 | 17.7 |
| 10 | 18 |
| 11 | 18.7 |
| 12 | 19.5 |
| 13 | 20.2 |
| 14 | 20.8 |
| 15 | 21.1 |
| 16 | 21.5 |
| 17 | 23.2 |
| 18 | 24.2 |
| 19 | 24.8 |
| 20 | 25.1 |
| 21 | 25.6 |

Figure 54:
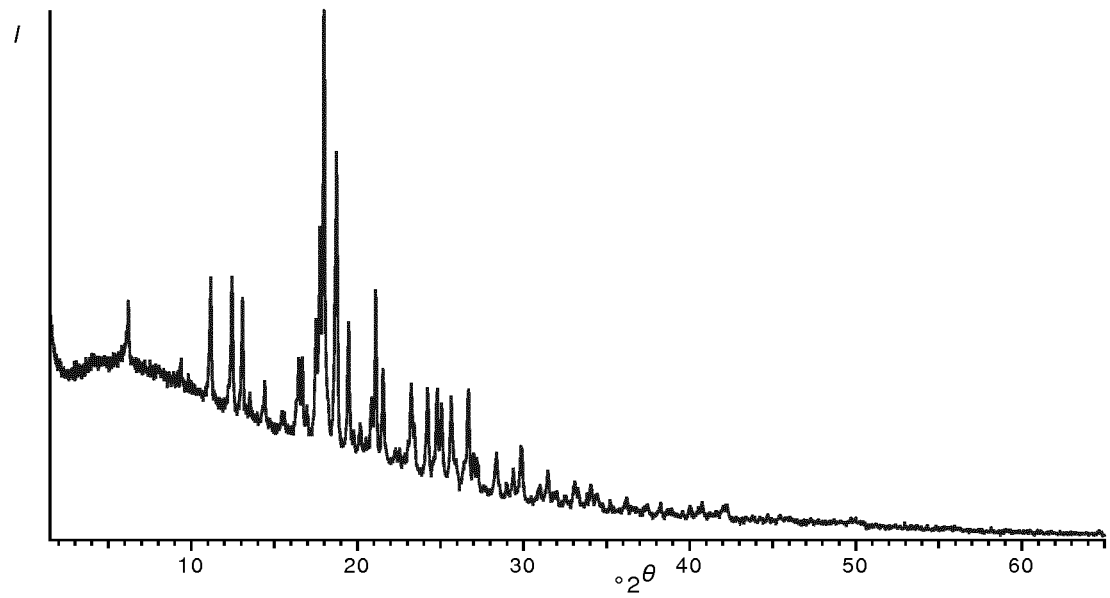
FIG. 54: Powder X-ray diffractogram of Mesylate salt form Mesylate-NF1.
Figure 55:
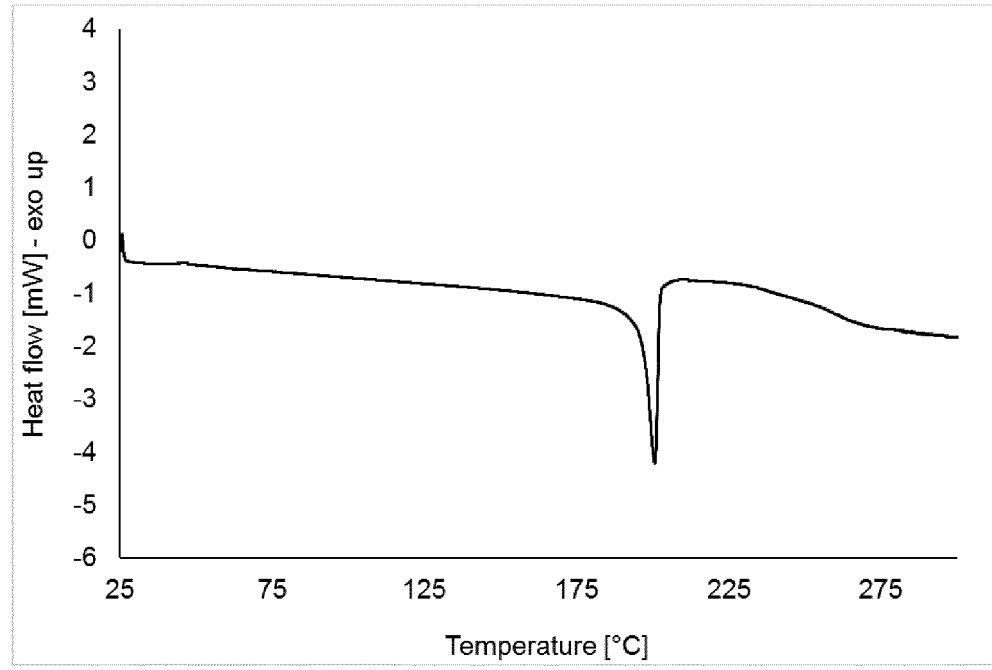
FIG. 55: DSC scan of Mesylate salt form Mesylate-NF1 (5 K/min).
Figure 56:
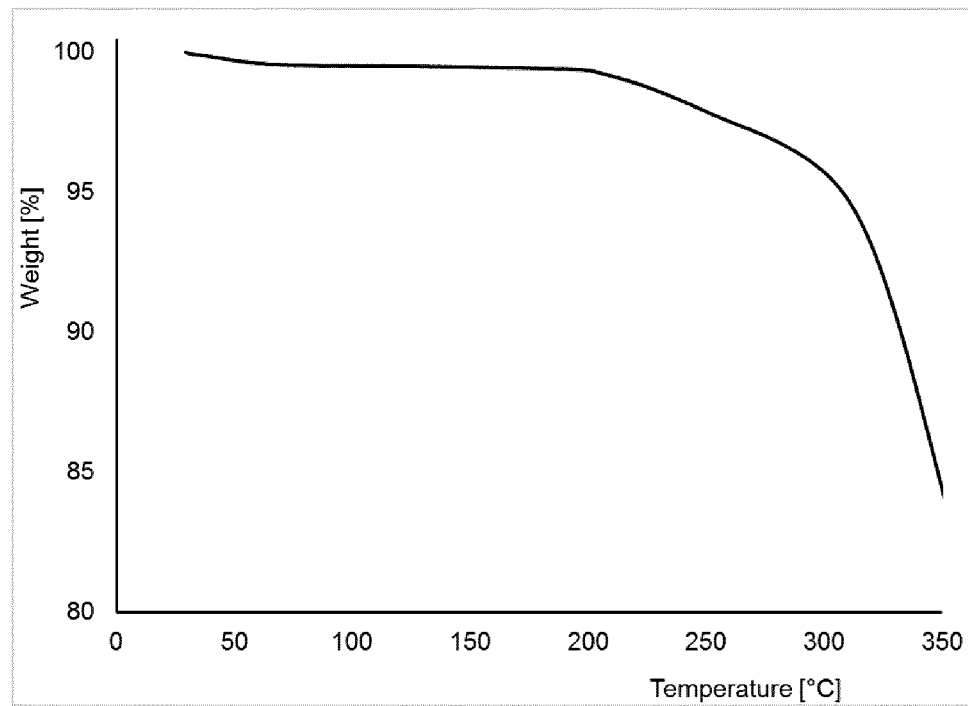
FIG. 56: TGA scan of Mesylate salt form Mesylate-NF1 (5 K/min).
Figure 57:
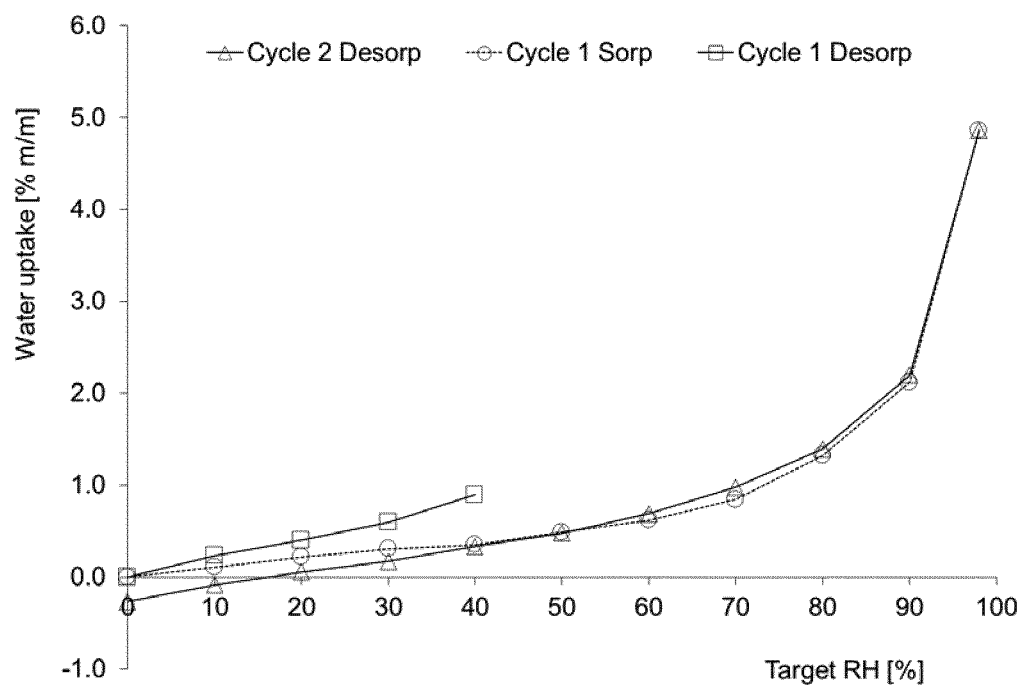
FIG. 57: Water Vapour Sorption Isotherm (25° C.) of Mesylate salt form Mesylate-NF1.

In another embodiment, form Mesylate-NF1 is characterized by a diffraction pattern substantially similar to that of FIG. 54.

A Powder X-Ray Diffraction pattern of free base form Mesylate-NF1 was obtained by standard techniques as described in the European Pharmacopeia 6$^{th}$ Edition chapter 2.9.33, and was characterised by the following X-ray powder diffractogram (monochromatic Cu-Kα$_1$ radiation, λ=1.5406 Å, Stoe StadiP 611 KL transmission diffractometer).

In another embodiment, form Mesylate-NF1 is characterized as a crystalline anhydrous form.

Other physical properties of form Mesylate-NF1 include the following: Thermal behaviour of Mesylate salt form Mesylate-NF1 showed a melting peak onset at approx. 196° C. Thermogravimetric analysis revealed a low weight loss of approx. 0.6% m/m up to this temperature. DSC and TGA profiles are displayed in the figures. DSC scan of Mesylate salt form Mesylate-NF1 was acquired on a Mettler-Toledo DSC 821e with a heating rate of 5 K/min, using nitrogen purge gas at 50 mL/min. TGA scan of Mesylate salt form Mesylate-NF1 was acquired on a Mettler-Toledo TGA 851 with a heating rate of 5 K/min, using nitrogen purge gas at 50 mL/min. Water Vapour Sorption behaviour of Mesylate salt form Mesylate-NF1 revealed small water uptake levels ≤1% m/m in the relative humidity (rh) range 0-80% rh, and slightly elevated water uptake levels ≤5 m/m in the relative humidity (rh) range 90-98% rh. Mesylate salt form Mesylate-NF1 can be classified as slightly hygroscopic acc. to Ph. Eur. Criteria (section 5.11.). Water Vapor Sorption isotherm (25° C.) of Mesylate salt form Mesylate-NF1 is displayed in the figures. Water Vapour Sorption isotherm was acquired on a DVS-Advantage system from SMS. Overall, Mesylate salt form Mesylate-NF1 revealed good solid-state properties (good crystallinity, slightly hygroscopic, high thermal stability).

In one embodiment, the invention provides for Compound 1 characterized as a mixture of crystalline forms A1 and A2.

The development of solid-state preparation routes was mainly based on solvent crystallisation approaches to enable scalability to large scale as well as providing powder material with good manufacturability properties.

A mixture of morphic forms is not favorable from a regulatory and quality perspective, as phase compositions of mixtures are challenging to control from batch to batch. Variability of phase compositions requires extensive characterisation to assess impact on critical quality attributes (e.g. oral absorption behavior, stability behavior) and may also jeopardise robust DP manufacturability if parameters such as particle habit are different for different forms and mixtures thereof.

Surprisingly, the invention provides preparation routes for the thermodynamically stable phase-pure crystalline form A2 of Compound 1, which provides powder material with good manufacturability properties in large scale.

In another aspect, the invention features a pharmaceutical composition comprising any of the forms and salts described above, and a pharmaceutically acceptable carrier. In another embodiment, the pharmaceutical composition further comprises an additional therapeutic agent.

In another aspect, the invention features a process of preparing Form A1 or A2 comprising dissolving Compound 1 in an organic solvent, water, or a mixture thereof. In certain embodiments, the solvent is Ethanol, 1-Propanol, 2-Propanol, 2-Butanol, Acetone, Methyl ethyl ketone, Methyl isobutyl ketone, Ethyl acetate, 1,4-Dioxane, Di ethyl ether, Methyl tert butyl ether, Tetrahydrofuran, Acetonitrile, Dichloromethane, Chloroform, Toluene, or Pyridine, or a mixture thereof. In certain embodiments, the solvent is Ethanol, 1-Propanol, 1-Butanol, Iso-Butanol, Methyl ethyl ketone, Methyl isobutyl ketone, Ethyl acetate, 1,4-Dioxane, Di ethyl ether, Methyl tert butyl ether, Tetrahydrofuran, Acetonitrile, Dichloromethane, Chloroform, N,N-Dimethylformamide, Toluene, ortho-Xylene, para-Xylene, or Pyridine, or a mixture thereof.

In certain embodiments, the solvent is Ethanol, 2-Propanol, Acetone, Methyl isobutyl ketone, Ethyl acetate, Acetonitrile, or Toluene, or a mixture thereof.

In certain embodiments, Compound 1 is dissolved in the organic solvent between about 20 and 75° C. In certain embodiments, Compound 1 is dissolved in the organic solvent at about 25° C. In certain embodiments, Compound 1 is dissolved in the organic solvent at about 50° C.

In certain embodiments, the invention features a process of preparing Form A2 comprising dissolving Compound 1 or form A1 of Compound 1 in an alcohol, water, or a mixture thereof.

In certain embodiments, the process comprises a mixture of alcohol and water. In certain embodiments, the alcohol is methanol, ethanol, or 2-propanol.

In certain embodiments, the compounds and solid forms of the invention were synthesized in accordance with the schemes provided in the Examples below.

4. Uses, Formulation and Administration

Pharmaceutically Acceptable Compositions

According to another embodiment, the invention provides a composition comprising a solid form of compound 1 of this invention or a pharmaceutically acceptable derivative thereof and a pharmaceutically acceptable carrier, adjuvant, or vehicle. The amount of solid form of compound 1 in compositions of this invention is such that is effective to measurably inhibit BTK, or a mutant thereof, in a biological sample or in a patient. In certain embodiments, the amount of solid form of compound 1 in compositions of this invention is such that is effective to measurably inhibit BTK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the solid form of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting BTK, or a mutant thereof, in a patient or in a biological sample comprising the step of administering to said patient or contacting said biological sample with a solid form of compound 1, or pharmaceutically acceptable salts thereof, according to the invention.

In certain embodiments, the invention is directed to the use of a solid form of compound 1, or pharmaceutically acceptable salts thereof, for modulating or inhibiting a BTK enzyme. The term "modulation" denotes any change in BTK-mediated signal transduction, which is based on the action of the specific inventive compounds capable to interact with the BTK target in such a manner that makes recognition, binding and activating possible. The compounds are characterized by such a high affinity to BTK, which ensures a reliable binding of BTK. In certain embodiments, the substances are highly selective for BTK over most other kinases in order to guarantee an exclusive and directed recognition with the single BTK target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present protein/ligand(enzyme-inhibitor)- interaction is characterized by high affinity, high selectivity and minimal or even lacking cross-reactivity to other target molecules to exclude unhealthy and harmful impacts to the treated subject.

In certain embodiments, the present invention relates to a method for inhibiting a BTK enzyme, with at least a solid form of compound 1, or pharmaceutically acceptable salts thereof, under conditions such that said BTK enzyme is inhibited. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating a BTK enzyme is performed in-vitro. The prior teaching of the present specification concerning a solid form of compound 1, or pharmaceutically acceptable salts thereof, including any embodiments thereof, is valid and applicable without restrictions to the compounds when used in the method for inhibiting BTK. The prior teaching of the present specification concerning a solid form of compound 1, or pharmaceutically acceptable salts thereof, is valid and applicable without restrictions to the compounds when used in the method for inhibiting BTK.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc epsilon RI). BTK deficient murine mast cells have reduced degranulation and decreased production of proinflammatory cytokines following Fc epsilon RI cross-linking (Kawakami et al. Journal of Leukocyte Biology 65: 286-290).

Provided solid forms of compound 1, or pharmaceutically acceptable salts thereof, are inhibitors of BTK and are therefore useful for treating one or more disorders associated with activity of BTK. Thus, in some embodiments, the present invention provides a method for treating a BTK-mediated disorder comprising the step of administering to a patient in need thereof a solid form of compound 1, or pharmaceutically acceptable salts thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In certain embodiments, the cancer is Non-Hodgkin's Lymphoma mantle cell lymphoma or Non-Hodgkins's Lymphoma diffuse large b-cell lymphoma, including the abc subtype.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE or lupus), lupus nephritis, vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In certain embodiments, the disease or condition is systemic lupus erythematosus (SLE or lupus) or lupus nephritis.

In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder or cardiovascular disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. In certain embodiments, the present invention provides an anti-thrombotic agent because Btk is also involved in the activation of platelets.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, diabetes (e.g. type I diabetes), irritable bowel syndrome, Crohn's disease, lupus and renal transplant.

In certain embodiments, the invention provides a method for the treatment and/or prophylaxis of multiple sclerosis (MS), including relapsing MS (RMS), relapsing-remitting MS (RRMS), progressive MS (PMS), secondary-progressive MS (SPMS), primary-progressive MS (PPMS), and progressive-relapsing MS (PRMS), comprising administering to a subject a solid form of compound 1.

It is another object of the invention to provide a method for treating diseases that are caused, mediated and/or propagated by BTK activity, wherein a solid form of compound 1, or pharmaceutically acceptable salts thereof is administered to a mammal in need of such treatment. In certain embodiments, the invention provides a method for treating lupus, wherein a solid form of compound 1, or pharmaceutically acceptable salts thereof is administered to a mammal in need of such treatment. In certain embodiments, the compound is administered in an effective amount as defined above. In certain embodiments, the treatment is an oral administration.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit BTK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing BTK-dependent signal transduction pathways in animals and/or cell culture models or in the clinical diseases mentioned in this application.

Moreover, the subsequent teaching of the present specification concerning the use of a solid form of compound 1, or pharmaceutically acceptable salts thereof for the production of a medicament for the prophylactic or therapeutic treatment and/or monitoring is considered as valid and applicable without restrictions to the use of the compound for the inhibition of BTK activity if expedient.

The invention also relates to the use of a solid form of compound 1, or pharmaceutically acceptable salts thereof for the prophylactic or therapeutic treatment and/or monitoring of diseases that are caused, mediated and/or propagated by BTK activity. Furthermore, the invention relates to the use of a solid form of compound 1, or pharmaceutically acceptable salts thereof for the production of a medicament for the prophylactic or therapeutic treatment and/or monitoring of diseases that are caused, mediated and/or propagated by BTK activity. In certain embodiments, the invention provides the use of a solid form of compound 1, or pharmaceutically acceptable salts thereof, for the production of a medicament for the prophylactic or therapeutic treatment of a BTK-mediated disorder.

Another object of the present invention is a solid form of compound 1, or pharmaceutically acceptable salts thereof for use in the prophylactic or therapeutic treatment and/or monitoring of diseases that are caused, mediated and/or propagated by BTK activity. Another preferred object of the invention concerns a solid form of compound 1, or pharmaceutically acceptable salts thereof for use in the prophylactic or therapeutic treatment and/or monitoring of lupus.

The solid form of compound 1, or pharmaceutically acceptable salts thereof can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with BTK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one solid form of compound 1, or pharmaceutically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with BTK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2] Rec. INN (Recommended International Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting BTK activity in a biological sample comprising the step of contacting said biological sample with a compound of this invention, or a composition comprising said compound.

According to another embodiment, the invention relates to a method of inhibiting BTK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of BTK, including the evaluation of the many factors thought to influence, and be influenced by, the production of BTK and the interaction of BTK. The present compounds are also useful in the development of other compounds that interact with BTK since the present compounds provide important structure-activity relationship (SAR) information that facilitate that development. Compounds of the present invention that bind to BTK can be used as reagents for detecting BTK in living cells, fixed cells, in biological fluids, in tissue homogenates, in purified, natural biological materials, etc. For example, by labeling such compounds, one can identify cells expressing BTK. In addition, based on their ability to bind BTK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing BTK inside permeabilized cells. The compounds of the invention can also be utilized as commercial research reagents for various medical research and diagnostic uses. Such uses can include but are not limited to: use as a calibration standard for quantifying the activities of candidate BTK inhibitors in a variety of functional assays; use as blocking reagents in random compound screening, i.e. in looking for new families of BTK ligands, the compounds can be used to block recovery of the described BTK compounds; use in the co-crystallization with BTK enzyme, i.e. the compounds of the present invention will allow formation of crystals of the compound bound to BTK, enabling the determination of enzyme/compound structure by x-ray crystallography; other research and diagnostic applications, wherein BTK is preferably activated or such activation is conveniently calibrated against a known quantity of an BTK inhibitor, etc.; use in assays as probes for determining the expression of BTK in cells; and developing assays for detecting compounds which bind to the same site as the BTK binding ligands.

The compounds of the invention can be applied either themselves and/or in combination with physical measurements for diagnostics of treatment effectiveness. Pharmaceutical compositions containing said compounds and the use of said compounds to treat BTK-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of BTK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

All forms were characterized according to standard methods which are found in e.g. Rolf Hilfiker, 'Polymorphism in the Pharmaceutical Industry', Wiley-VCH. Weinheim 2006 (Chapter 6: X-Ray Diffraction, Chapter 6: Vibrational Spectroscopy, Chapter 3: Thermal Analysis, Chapter 9: Water Vapour Sorption, and references therein); and H. G. Brittain, 'Polymorphism in Pharmaceutical Solids, Vol. 95, Marcel Dekker Inc., New York 1999 (Chapter 6 and references therein).

Unless otherwise indicated, all temperatures are expressed in ° C. (degrees Centigrade). All reactions were conducted at room temperature unless otherwise noted. All compounds of the present invention were synthesized by processes developed by the inventors.

$^1$H-NMR spectra were recorded on a Bruker Avance III 400 MHz. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), m (multiplet), or br (broad).

Mass spectra were obtained on Agilent 1200 Series mass spectrometers from Agilent technologies, using either Atmospheric Chemical Ionization (APCI) or Electrospray Ionization (ESI). Column: XBridge C8, 3.5 µm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B.

HPLC data were obtained using Agilent 1100 series HPLC from Agilent technologies using XBridge column (C8, 3.5 µm, 4.6×50 mm). Solvent A: water+0.1% TFA; Solvent B: ACN; Flow: 2 ml/min; Gradient: 0 min: 5% B, 8 min: 100% B, 8.1 min: 100% B, 8.5 min: 5% B, 10 min 5% B.

The microwave reactions were conducted using Biotage Initiator Microwave Synthesizer using standard protocols that are known in the art.

Some abbreviations that may appear in this application are as follows:

| | |
|---|---|
| δ | chemical shift |
| API | Active pharmaceutical ingredient |
| d | deuterium or doublet |
| dd | doublet of doublets |
| DCM | dichloromethane |
| DMF | dimethylformamide |
| DMSO | dimethylsulfoxide |
| THF | tetrhydrofuran |
| eq. | equivalent |
| h | hour |
| $^1$H | proton |
| HPLC | high pressure liquid chromatography |
| J | coupling constant |
| LC | liquid chromatography |
| m | multiplet |
| M | molecular ion |
| MHz | Megahertz |
| min | minute |
| mL | milliliter |
| MS | mass spectrometry |

-continued

| | |
|---|---|
| m/z | mass-to-charge ratio |
| NMR | nuclear magnetic resonance |
| RBF | Round Bottom Flask |
| RT | room temperature |
| s | singlet |
| TLC | thin layer chromatography |
| UV | ultraviolet |

Compound numbers utilized in the Examples below correspond to compound numbers set forth supra.

Example 1: Lyophilisation Experiments from 0.1% TFA-H2O/ACN Mixtures (Following Variations as Described in WO2012/170976, Method S4A)

a) Lyophilisation from 0.1% TFA-H2O:ACN 90:10 (v:v):

Approx. 200 mg purified free base were dissolved in 50 mL of a mixture 0.1% TFA-H2O:ACN 90:10 (v:v) at RT (approx. 22° C.). The substance was almost completely dissolved. To obtain a clear solution, a filtration through a 0.45 µm syringe filter was carried out. This solution was flash-frozen in liquid nitrogen in a 100 mL round-bottom flask, and frozen sample attached to lyophilisator (Steris, Lyovac GT2) operating at approx. 0.8 mbar. After 1 day, a white solid residue was collected.

NMR: stoichiometry API:TFA ca. 1:1.1

$^1$H NMR (400 MHz, DMSO-d6) δ 8.36 (s, 1H), 7.48-7.41 (m, 2H), 7.32-7.25 (m, 2H), 7.23-7.07 (m, 7H), 6.87 (t, J=6.5 Hz, 1H), 6.80 (dd, J=16.7, 10.5 Hz, 1H), 6.09 (dd, J=16.8, 2.4 Hz, 1H), 5.67 (dd, J=10.4, 2.4 Hz, 1H), 4.28-4.18 (m, 1H), 3.97-3.87 (m, 1H), 3.64 (dd, J=20.6, 6.5 Hz, 2H), 3.24 (t, J=12.7 Hz, 1H), 2.88 (t, J=12.6 Hz, 1H), 1.78-1.68 (m, 2H), 1.68-1.44 (m, 2H)

b) Lyophilisation from 0.1% TFA-H2O:ACN 50:50 (v:v):

Approx. 200 mg purified free base were dissolved in 15 mL of a mixture 0.1% TFA-H2O:ACN 50:50 (v:v) at RT (approx. 22° C.). The substance was almost completely dissolved. To obtain a clear solution, a filtration through a 0.45 µm syringe filter was carried out. This solution was flash-frozen in liquid nitrogen in a 100 mL round-bottom flask, and frozen sample attached to lyophilisator (Steris, Lyovac GT2) operating at approx. 0.8 mbar. After 1 day, a white solid residue was collected.

NMR: stoichiometry API:TFA ca. 1:0.3

$^1$H NMR (400 MHz, DMSO-d6) δ 8.06 (s, 1H), 7.46-7.39 (m, 2H), 7.27-7.22 (m, 2H), 7.21-7.15 (m, 1H), 7.15-7.09 (m, 4H), 6.80 (dd, J=16.7, 10.4 Hz, 1H), 6.09 (dd, J=16.7, 2.4 Hz, 1H), 6.01-5.90 (m, 2H), 5.71-5.62 (m, 1H), 5.66 (dd, J=10.5, 2.4 Hz, 1H), 4.25-4.14 (m, 1H), 3.95-3.85 (m, 1H), 3.60 (dd, J=20.8, 6.4 Hz, 2H), 2.94-2.85 (m, 1H), 1.76-1.66 (m, 2H), 1.66-1.45 (m, 2H)

c) Lyophilisation from 0.1% TFA-H2O:ACN 10:90 (v:v):

Approx. 200 mg purified free base were dissolved in 8 mL of a mixture 0.1% TFA-H2O:ACN 10:90 (v:v) at RT (approx. 22° C.). The substance was almost completely dissolved. To obtain a clear solution, a filtration through a 0.45 µm syringe filter was carried out. This solution was flash-frozen in liquid nitrogen in a 100 mL round-bottom flask, and frozen sample attached to lyophilisator (Steris, Lyovac GT2) operating at approx. 0.8 mbar. After 1 day, a white solid residue was collected.

NMR: stoichiometry API:TFA ca. 1:0.02

$^1$H NMR (400 MHz, DMSO-d6) δ 7.96 (s, 1H), 7.46-7.38 (m, 2H), 7.27-7.21 (m, 2H), 7.20-7.14 (m, 1H), 7.14-7.08 (m, 4H), 6.80 (dd, J=16.7, 10.5 Hz, 1H), 6.09 (dd, J=16.6, 2.4 Hz, 1H), 5.65 (dd, J=10.5, 2.4 Hz, 1H), 5.60-5.51 (m,

2H), 5.20 (t, J=6.4 Hz, 1H), 4.24-4.13 (m, 1H), 3.95-3.85 (m, 1H), 3.58 (dd, J=20.9, 6.4 Hz, 2H), 3.28-3.19 (m, 1H), 2.90 (t, J=12.7 Hz, 1H), 1.76-1.66 (m, 2H), 1.65-1.45 (m, 2H)

Example 2: Crystallisation Processes of Free Base to Obtain Pure Form A1 a) Small Scale: Crystallisation from Several Solvents by Isothermal Solvent Evaporation Approx. 10 mg free base were dispersed or dissolved in 500 µL up to 4 mL (depending on solubility) of several solvents at RT or 50° C. All suspension/solutions were filtered using a 0.2 µm syringe filter. Vials with clear filtrates were open placed in a tempered aluminium rack for isothermal solvent evaporation until a dry solid residue was obtained. In following solvents, form A1 was obtained: 25° C.: Ethanol, 1-Propanol, 2-Propanol, 2-Butanol, Acetone, Methyl ethyl ketone, Methyl isobutyl ketone, Ethyl acetate, 1,4-Dioxane, Di ethyl ether, Methyl tert butyl ether, Tetrahydrofuran, Acetonitrile, Dichloromethane, Chloroform, Toluene, Pyridine; 50° C.: Ethanol, 1-Propanol, 1-Butanol, Iso-Butanol, Methyl ethyl ketone, Methyl isobutyl ketone, Ethyl acetate, 1,4-Dioxane, Di ethyl ether, Methyl tert butyl ether, Tetrahydrofuran, Acetonitrile, Dichloromethane, Chloroform, N,N-Dimethylformamide, Toluene, ortho-Xylene, para-Xylene, Pyridine.

b) Small Scale: Cooling Crystallisation from Several Solvents

Approx. 14 mg free base were dispersed or dissolved in 200 µL up to 1 mL (depending on solubility) of several solvents at 50° C. All suspension/solutions were filtered using a 0.2 µm syringe filter. Vials with clear filtrates were closed placed in a tempered aluminium rack and cooled down to 5° C. at 0.1 K/min. Obtained solids were solid-/liquid separated by centrifugation using PE centrifuge vials. In following solvents, form A1 was obtained:

Ethanol, 2-Propanol, Acetone, Methyl isobutyl ketone, Ethyl acetate, Acetonitrile, Toluene.

c) Large Scale: Combination of Evaporation and Cooling Crystallisation

The 65 L enamel reactor was made inert with nitrogen. Using the feed vessel, 25 L Ethanol absolute was filled into the reactor. Stirring, condenser 0° C. and jacket temperature 30° C. were started. Then the product was filled in (3980 g of several batches of free base). The jacket temperature was raised up to 95° C. After 30 min the reaction temperature was 78° C. (reflux conditions) and a turbid solution was formed. The hot mixture was filtered over the pressure filter and rinsed with 2 L Ethanol. In the vessel and on the filter a small amount of a brown residue was detected. The filtrate was transferred into the rotary evaporator. There were approximately 13 L Ethanol distilled off until crystallisation has started. The mixture was filled into a steel pot and stirred for 2 h under ice cooling, while a precipitate was formed. The precipitate was filtered with suction and rinsed with 1 L Ethanol. Then it was dried for 2 days in the vacuum dryer at 51° C. and 30 mbar. The product was milled in the comil U5 (mesh size 1 mm).

$^1$H NMR (400 MHz, DMSO-d6) δ 7.96 (s, 1H), 7.46-7.39 (m, 2H), 7.27-7.21 (m, 2H), 7.20-7.14 (m, 1H), 7.14-7.09 (m, 4H), 6.79 (dd, J=16.7, 10.5 Hz, 1H), 6.09 (dd, J=16.7, 2.4 Hz, 1H), 5.65 (dd, J=10.5, 2.4 Hz, 1H), 5.62-5.50 (m, 2H), 5.20 (t, J=6.4 Hz, 1H), 4.24-4.13 (m, 1H), 3.95-3.84 (m, 1H), 3.59 (dd, J=20.9, 6.4 Hz, 2H), 3.24 (t, J=12.9 Hz, 1H), 2.91 (t, J=12.2 Hz, 1H), 1.77-1.65 (m, 2H), 1.67-1.45 (m, 2H).

Example 3: Crystallisation Processes of Free Base to Obtain Pure Form A2 a) Small Scale: Cooling Crystallisation from 2-Propanol

Approx. 14 mg free base were completely dissolved in 200 µL 2-Propanol. The solution was filtered using a 0.2 µm syringe filter. The vial with clear filtrate was closed placed in a tempered aluminium rack and cooled down to 5° C. at 0.1 K/min. Obtained solid was solid-/liquid separated by centrifugation using a PE centrifuge vial.

b) Small Scale: Slurry Conversion Form A1 in Ethanol

Approx. 2.5 g free base form A1 and 25 mL Ethanol were added to a 50 mL Erlenmeyer flask. Obtained suspension was heated to 50° C. and stirred for approx. 3 h. Approx. 50 mg seeds of form A2 were added to the suspension. In process control (IPC 1) after ca. 20 h by PXRD showed form A1. An additional amount of approx. 100 mg seeds of form A2 was given to the suspension. Second IPC after 30 h stirring at 50° C. showed still form A1. After stirring for further 10 h the material converted completely to form A2 (IPC 3). The Ethanol was evaporated in rotary evaporator under vacuum to dryness. The material was final dried at 80° C. in a dry Nitrogen flow.

c) Large Scale: Slurry Conversion Form A1 in Ethanol 3.2 kg of several drug substance batches and 9 L Ethanol absolute GR for analysis were added to the reaction mixture of Compound 1 into the 25 L enamel reactor (25 L enamel reactor (POS 1065) and a white suspension was obtained. A sample was taken (IPC1, 0 h) and PXRD quantification showed a mixture of 13% form A1 and 87% form A2. The suspension was heated to 35° C. (reactor) and stirred overnight. A sample was taken (IPC2, 18 h) and PXRD quantification showed a mixture of 11% form A1 and 89% form A2. Tempering was stopped and the mixture was cooled down slowly to room temperature. 30 g of form A2 were triturated in a mortar and added stepwise within 10 minutes at 28° C. (reactor). The mixture was stirred overnight at room temperature. A sample was taken (IPC3, 41 h) and PXRD quantification showed a mixture of 11% form A1 and 89% form A2. 4×5 g of form A2 were triturated in a mortar and added within 4 h at 25° C. (reactor). The suspension was heated to 35° C. (reactor) and stirred over weekend at this temperature. A sample was taken (IPC4, 113 h) and PXRD quantification showed a mixture of 10% form A1 and 90% form A2. 5 h later the tempering was stopped. 3×8 g of form A2 were triturated in a mortar and added within 3 h at 33-35° C. (reactor). The mixture was stirred overnight at 25° C. A sample was taken (IPC5, 137 h) and PXRD quantification showed a mixture of 7% form A1 and 93% form A2. The mixture was heated to 35° C. (reactor). 3×8 g of form A2 were triturated in a mortar and added within 3 h at 33-35° C. (reactor). Tempering was stopped and the mixture was cooled down slowly to room temperature. The mixture was stirred overnight at 25° C. (reactor). A sample was taken (IPC5, 161 h) and PXRD quantification showed 100% A2. The suspension was heated to 35° C. and then tempering was stopped. 3×8 g of form A2 were triturated in a mortar and added within 3 h at 33-35° C. (reactor). The suspension was cooled down slowly to room temperature and stirred overnight. The solvent was removed by distillation in a rotary evaporator (Büchi R220 EX). The concentrated suspension was stored overnight at room temperature. The suspension was filtered with suction. The cake was dried over weekend at 50° C. and 20 mbar to constant mass. were milled with the comil U5 (mesh size 1 mm).

¹H NMR (500 MHz, DMSO-d6) δ 8.32 (s, 1H), 7.47-7.42 (m, 2H), 7.30-7.26 (m, 2H), 7.22-7.18 (m, 1H), 7.17-7.11 (m, 4H), 6.96-6.85 (m, 2H), 6.83-6.76 (m, 2H), 6.09 (dd, J=16.7, 2.4 Hz, 1H), 5.66 (dd, J=10.4, 2.4 Hz, 1H), 4.27-4.18 (m, 1H), 3.96-3.87 (m, 1H), 3.69-3.58 (m, 2H), 3.24 (t, J=12.8 Hz, 1H), 2.88 (t, J=12.5 Hz, 1H), 1.78-1.68 (m, 2H), 1.67-1.46 (m, 2H).

d) Small Scale: Cooling Crystallisation in Methanol by Seeding Form A2

30.0 g drug substance and 120 g Methanol were added to a 250 mL jacketed reactor. The suspension was heated to 65° C. After approx. 45 min at reflux conditions a clear, slightly yellowish solution was obtained. The jacket temperature was subsequently cooled down fast to 58° C. While cooling, 300 mg seed crystals of form A2 (formerly triturated in a porcelain mortar) were added to the solution at 59° C. The resulting suspension was further cooled down to −28° C. with a cooling rate of −0.23 K/min and finally filtered under vacuum using a funnel filter. The isolated filter cake was washed twice with 30 mL pre-cooled methanol (at −30° C.) and dried 16 h at 40° C. under vacuum (<10 mbar) affording 27.3 g of crystals of pure form A2 (90% yield).

e) Small Scale: Cooling Crystallisation in Ethanol by Seeding Form A2

5.0 g drug substance and 66.4 g Ethanol were added to a 250 mL jacketed reactor. The suspension was heated and dissolved at 76° C. forming a clear, slightly yellowish solution. The jacket temperature was subsequently cooled down fast to 58° C. 50 mg seed crystals of form A2 (formerly triturated in a porcelain mortar) were added to the solution at 58° C. and the resulting suspension was further cooled down to −30° C. with a cooling rate of −0.62 K/min. At the final temperature the suspension was further stirred 22 h (overnight) and finally filtered under vacuum using a funnel filter. The isolated filter cake was washed twice with 5 mL pre-cooled ethanol (at −30° C.) and dried 24 h at 40° C. under vacuum (<10 mbar) affording 4.17 g of crystals of pure form A2 (83% yield).

f) Large Scale: Cooling Crystallisation in Methanol by Seeding Form A2

82 L of Methanol (7 Vol.) were charged to a 250 L reactor and warmed to external temperature of 70° C. 11.72 kg of drug substance were slowly charged to the pre-warmed (reflux) Methanol. In roughly 15 min the solid was completely dissolved. The hot solution was filtered thought 0.45 µm cartridge. The filtrate was charged back to the cleaned reactor, pre-warmed at 70° C. The temperature ramp started: external temperature from +70° C. down to −20° C. in 900 min. When the internal temperature reached 50° C., the seeding crystals were added (1% wt/wt, with respect of the crude API). When the external temperature reached −20° C., the mixture was stirred for 30 min and then the solid was isolated by filtration, the cake was washed with MeOH and dried at 50° C. for 12 hrs.

¹H NMR (500 MHz, DMSO-d6) δ 7.96 (s, 1H), 7.45-7.39 (m, 2H), 7.26-7.21 (m, 2H), 7.19-7.15 (m, 1H), 7.14-7.09 (m, 4H), 6.79 (dd, J=16.7, 10.5 Hz, 1H), 6.09 (dd, J=16.7, 2.4 Hz, 1H), 5.65 (dd, J=10.5, 2.4 Hz, 1H), 5.61-5.50 (m, 2H), 5.19 (t, J=6.4 Hz, 1H), 4.23-4.13 (m, 1H), 3.94-3.85 (m, 1H), 3.59 (dd, J=21.1, 6.7 Hz, 2H), 3.24 (t, J=12.9 Hz, 1H), 2.90 (t, J=12.3 Hz, 1H), 1.77-1.67 (m, 2H), 1.67-1.47 (m, 2H).

g) Kilo-Lab: Cooling Crystallisation in Methanol without Seeding, to Form A2

2300 ml of Methanol (6.5 Vol) were charged to a 5 L oil jacketed reactor and warmed to ET=70° C. 353.2 g of crude drug substance were slowly charged to the pre-warmed Methanol. When the IT reached the 58° C. the mixture was still a turbid solution with the presence of undissolved material. Further 180 ml (0.5 Vol) of Methanol were added and the ET increased to 75° C. (reflux at IT=62° C.). In roughly 30 min the solid was completely dissolved and the hot solution was filtered on a 2.5 um paper filter (Whatman 42). The filtrate was charged back to the cleaned reactor pre-warmed at 70° C. Since during the under vacuum filtration, some product precipitated out (turbid solution observed, it was necessary to increase the ET to 75° C. to obtain a clear solution. Then ET was lowered to 70° C. and the temperature ramp started: ET from +70° C. up to −20° C. in 900 min.

Example 4: Preparation Processes for First Setup of Salt Screening

First setup of salt screening was carried out with Sulfuric Acid, Phosphoric Acid, Toluene Sulfonic Acid and Succinic Acid.

Cooling crystallisations with stoichiometric 1:1 (base: acid) combinations in 2-Propanol, Toluene and THF/Water (0.5:1; v:v) were started. Approx. 20 mg API was dissolved at high temperature and the acid was dosed in the respective amount to the solution. Solid acids were weighed and added as solid into the API solution and liquid acids were dissolved in the respective solvent and given by a pipette to the API solution. In no case a spontaneous salt precipitation after dosage of acid could be observed. Then the solution was cooled down to 5° C. with a slow cooling rate, e.g. 1 K/min (in experiments with 2-PrOH 3-fold cycles heating→cooling were run). In cases where no crystallisation occurred, the vials were placed for further days in the fridge. From Acetone evaporation crystallisations were carried out at RT.

From cooling crystallisations either no solid residues, amorphous solid residues or parent form A1 were obtained. From evaporation crystallisations in Acetone only amorphous residues were obtained. These residues were further treated by dissolving in Ethanol and carrying out of vapour diffusion experiments with Diethyl ether. In no case a crystalline residue was obtained.

Example 5: Preparation Processes for Novel Salt Forms a) Hydrochloride Salt Form HCl-NF1:

i) Experiment from Acetone and Subsequent Crystallisation of Obtained Amorphous Material from Ethanol:

Approx. 49 mg of free base and 108 µL Hydrochloric acid (32%, diluted 1:10 in Acetone) were dissolved in 2 mL Acetone at RT. No spontaneous precipitation was observed. The vial was open placed in a fume hood to evaporate the solvent. A glassy residue was obtained. To this residue 1 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. Again, a glassy residue was obtained. To the solution with glassy residue few mg seeds of Hydrochlochlorid salt form HCl-NF2 was added. Within one minute a white powder crystallised. 1 mL Diethyl ether was added to the suspension and it was solid-/liquid separated by centrifugation using a PE centrifuge vial.

ii) Experiment Directly from Ethanol:

Approx. 1 g free base was completely dissolved in 10 mL Ethanol under reflux conditions in a 100 mL round bottom flask over a water bath on a heating plate. By addition of 22 µL Hydrochloric acid (32%) no spontaneous precipitation was observed. The solution was cooled fast to 70° C., 60° C., 50° C., respectively. At no step did a precipitation occur. At 50° C. and 40° C. few mg seeds of HCl-NF1 was added to the solution, respectively. At both temperatures the seed dissolved. The solution was cooled fast to 20° C. and no precipitation occurred. At 20° C. few mg seeds of HCl-NF1 was added and small crumbs were formed. The solution was cooled fast to 5° C. and again few mg seeds of HCl-NF1 was added. A turbid solution was obtained. To the turbid solution 20 mL Diethyl ether were added and a fine suspension was observed. Further addition of 20 mL Diethyl ether led to yellow doughy residue on glass surface. Then 45 mL Diethyl ether were added fast and stirred overnight. A yellow sticky residue was scratched into solution by spatula and 10 mL Diethyl ether were fast dosed. The bath was heated to 40° C. and the sticky residue 20 min stirred. Then the batch was cooled from 40° C. to 5° C. within 1 h and further 5 mL Diethyl ether were added at 25° C. A fine white crystallisate was obtained. The solid/liquid separation was done by centrifugation using PE centrifuge vials. The obtained powder was dried for ca. 2 h at RT under Nitrogen flow.

b) Hydrochloride Salt Form HCl-NF2:

Approx. 20 mg of free base and 45 µL Hydrochloric acid (32%, diluted 1:10 in Acetone) were dissolved in 0.8 mL Acetone at RT. No spontaneous precipitation was observed. The vial was open placed in a fume hood to evaporate the solvent. A glassy residue was obtained. To this residue 0.4 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. A white residue was obtained and it was solid-/liquid separated by centrifugation using a PE centrifuge vial.

c) Hydrochloride Salt Form HCl-NF3:

Approx. 25 mg of free base and 56 µL Hydrochloric acid (32%, diluted 1:10 in Acetone) were dissolved in 0.8 mL Acetone at RT. No spontaneous precipitation was observed. There were 250 µL Diethyl ether added dropwise to the solution and it became turbid. A few mg seeds of form HCl-NF1 and further 250 µL Diethyl ether were added. After few minutes a white residue was obtained and it was stirred overnight. The obtained suspension was solid-/liquid separated by centrifugation using a PE centrifuge vial.

d) Hydrobromide Salt Form HBr-NF1:

Approx. 51 mg of free base and 133 µL Hydrobromic acid (48%, diluted 1:10 in Acetone) were dissolved in 2 mL Acetone at RT. No spontaneous precipitation was observed. The vial was open placed in a fume hood to evaporate the solvent. A glassy residue was obtained. To this residue 1 mL Ethanol was added and a clear solution was obtained. The vial with the clear solution was placed open in a closed bigger vial with Diethyl ether at the bottom as anti-solvent reservoir for vapour diffusion processes. Again, a glassy residue was obtained. To the solution with glassy residue few mg seeds of Hydrobromic salt form HBr-NF2 was added. Within one minute a white powder crystallised. 1 mL Diethyl ether was added to the suspension and it was solid-/liquid separated by centrifugation using a PE centrifuge vial.

e) Hydrobromide Salt Form HBr-NF2:

Approx. 20 mg of free base and 50 µL Hydrobromic acid (48%, diluted 1:10 in Acetone) were dissolved in 0.8 mL Acetone at RT. No spontaneous precipitation was observed. The vial was open placed in a fume hood to evaporate the solvent. A glassy residue was obtained. To this residue 0.4 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. A white residue was obtained and it was solid-/liquid separated by centrifugation using a PE centrifuge vial.

f) Oxalate Salt Form Oxalate-NF1:

i) Experiment from Acetone and Subsequent Crystallisation of Obtained Amorphous Material from Ethanol:

Approx. 19 mg of free base were dissolved in 0.8 mL Acetone at RT and approx. 5 mg Oxalic acid were added to the solution. No spontaneous precipitation was observed. The vial was open placed in a fume hood to evaporate the solvent. A glassy residue was obtained. To this residue 0.4 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. A white residue was obtained and it was solid-/liquid separated by centrifugation using a PE centrifuge vial.

ii) Experiment Directly from Acetone by Anti-Solvent Precipitation:

Approx. 989 mg free base were completely dissolved in 15 mL Acetone under reflux conditions in a 250 mL round bottom flask over a water bath on a heating plate. By addition of 202 mg Oxalic acid dissolved in 1 mL Acetone no spontaneous precipitation was observed. Few mg seeds of Oxalate-NF1 was added and a turbid solution was obtained. The temperature of the water bath was set to 60° C. and further mg of seeds of form Oxalate-NF1 was added. The temperature of the water bath was decreased to 40° C. and a clear solution containing fine white particles was observed. At the temperature of 5° C. (water bath), a clear solution with fine white particles and dark chunks was obtained. To the solution 25 mL Diethyl ether were added dropwise and during addition the solution showed local white precipitation, then a turbid solution and finally sticky yellow residue at the glass wall. After fast dosage of further 100 mL Diethyl ether a white turbid solution and sticky yellow residue at the wall was obtained. Additional few mg of seeds of form Oxalate-NF1 and 10 mL Diethyl ether were added to the suspension and heated to RT. The obtained white suspension was cooled again to 5° C. At this temperature, the solid/liquid separation was done by centrifugation using PE centrifuge vials. The obtained powder was dried for ca. 2 h at RT under Nitrogen flow.

g) Maleate Salt Form Maleate-NF1:

i) Experiment from THF/Water and Subsequent Crystallisation of Obtained Amorphous Material from 2-Propanol:

Approx. 21 mg of free base were dissolved in a mixture of 500 µL THF+1 mL Water at 50° C. and approx. 6 mg Maleic acid were added to the solution. No spontaneous precipitation was observed. The solution was cooled to 5° C. and no crystallisation occurred. The vial was open placed in a fume hood to evaporate the solvent. A glassy residue was obtained. This residue was dissolved in 2-Propanol at 50° C. and cooled again to 5° C. No crystallisation occurred and the vial was placed in the fridge. After few days a white residue was obtained and it was solid-/liquid separated by centrifugation using a PE centrifuge vial.

ii) Experiment Directly from Toluene by Cooling Crystallisation:

Approx. 19 mg of free base were dissolved in 1 mL Toluene at 80° C. and approx. 5 mg Maleic acid were added to the solution. No spontaneous precipitation was observed. The solution was cooled to 5° C. A white powder was obtained and it was solid-/liquid separated by centrifugation using a PE centrifuge vial.

$^1$H NMR (500 MHz, DMSO-d6) δ 8.16 (s, 1H), 7.46-7.41 (m, 2H), 7.27-7.24 (m, 2H), 7.21-7.17 (m, 1H), 7.16-7.11 (m, 4H), 6.80 (dd, J=16.7, 10.5 Hz, 1H), 6.40-6.21 (m, 2H), 6.12 (s, 2H), 6.09 (dd, J=16.7, 2.4 Hz, 1H), 5.66 (dd, J=10.4, 2.4 Hz, 1H), 4.25-4.16 (m, 1H), 3.96-3.86 (m, 1H), 3.61 (dd, J=20.6, 6.4 Hz, 2H), 3.28-3.21 (m, 1H), 2.93-2.85 (m, 1H), 1.76-1.68 (m, 2H), 1.67-1.47 (m, 2H)

h) Maleate Salt Form Maleate-NF2:

Approx. 19 mg of free base were dissolved in 0.8 mL Acetone at RT and approx. 5 mg Maleic acid were added to the solution. No spontaneous precipitation was observed. The vial was open placed in a fume hood to evaporate the solvent. A glassy residue was obtained. To this residue 0.4 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. A white residue was obtained and it was solid-/liquid separated by centrifugation using a PE centrifuge vial.

$^1$H NMR (500 MHz, DMSO-d6) δ 8.14-8.10 (m, 1H), 7.45-7.41 (m, 2H), 7.27-7.24 (m, 2H), 7.21-7.16 (m, 1H), 7.16-7.09 (m, 4H), 6.80 (dd, J=16.7, 10.5 Hz, 1H), 6.10 (s, 2H), 6.11-6.07 (m, 1H), 6.30-5.76 (m, 2H), 5.66 (dd, J=10.5, 2.4 Hz, 1H), 4.23-4.16 (m, 1H), 3.94-3.86 (m, 1H), 3.60 (dd, J=20.7, 6.5 Hz, 2H), 3.46-3.37 (m, 1H), 2.93-2.85 (m, 1H), 1.75-1.67 (m, 2H), 1.67-1.46 (m, 2H)

i) Fumarate Salt Form Fumarate-NF1:

Approx. 6 mg of Fumarate-NF2 were weighed into a 40 μL Aluminium pan and heated in a DSC oven to approx. 130° C. for desolvation. DSC run was acquired on a Mettler-Toledo DSC 821e with a heating rate of 5 K/min, using nitrogen purge gas at 50 mL/min.

$^1$H NMR (500 MHz, DMSO-d6) δ 7.96 (s, 1H), 7.45-7.40 (m, 2H), 7.25-7.22 (m, 2H), 7.20-7.15 (m, 1H), 7.14-7.10 (m, 4H), 6.79 (dd, J=16.7, 10.5 Hz, 1H), 6.58 (s, 2H), 6.09 (dd, J=16.7, 2.5 Hz, 1H), 5.65 (dd, J=10.5, 2.4 Hz, 1H), 5.59-5.52 (m, 2H), 5.20 (t, J=6.4 Hz, 1H), 4.21-4.15 (m, 1H), 3.93-3.85 (m, 1H), 3.58 (dd, J=21.0, 6.5 Hz, 2H), 3.40-3.18 (m, 1H), 2.94-2.86 (m, 1H), 1.74-1.67 (m, 2H), 1.65-1.48 (m, 2H)

j) Fumarate Salt Form Fumarate-NF2:

Approx. 20 mg of free base were dissolved in 1 mL Toluene at 80° C. and approx. 5 mg Fumaric acid were added to the solution. No spontaneous precipitation was observed. The solution was cooled to 5° C. A white powder was obtained and it was solid-/liquid separated by centrifugation using a PE centrifuge vial.

$^1$H NMR (500 MHz, DMSO-d6) δ 7.96 (s, 1H), 7.44-7.39 (m, 2H), 7.27-7.22 (m, 2H), 7.19-7.10 (m, 5H), 6.79 (dd, J=16.7, 10.5 Hz, 1H), 6.62 (s, 2H), 6.09 (dd, J=16.7, 2.4 Hz, 1H), 5.65 (dd, J=10.5, 2.4 Hz, 1H), 5.60-5.51 (m, 2H), 5.20 (t, J=6.4 Hz, 1H), 4.22-4.15 (m, 1H), 3.93-3.86 (m, 1H), 3.62-3.55 (m, 2H), 3.25 (s, 1H), 2.94-2.86 (m, 1H), 1.75-1.66 (m, 2H), 1.66-1.47 (m, 2H)

k) Fumarate Salt Form Fumarate-NF3:

Approx. 20 mg of free base were dissolved in 0.8 mL Acetone at RT and approx. 5 mg Fumaric acid were added to the solution. No spontaneous precipitation was observed. The vial was open placed in a fume hood to evaporate the solvent. A glassy residue and a fraction of off-white powder was obtained. The off-white powder was extracted after solid-/liquid separated by centrifugation using a PE centrifuge vial.

$^1$H NMR (500 MHz, DMSO-d6) δ 7.96 (s, 1H), 7.44-7.40 (m, 2H), 7.25-7.22 (m, 2H), 7.19-7.15 (m, 1H), 7.14-7.10 (m, 4H), 6.79 (dd, J=16.7, 10.5 Hz, 1H), 6.62 (s, 2H), 6.09 (dd, J=16.7, 2.4 Hz, 1H), 5.65 (dd, J=10.5, 2.4 Hz, 1H), 5.58-5.54 (m, 2H), 5.20 (t, J=6.4 Hz, 1H), 4.22-4.15 (m, 1H), 3.93-3.86 (m, 1H), 3.64-3.55 (m, 2H), 3.27-3.19 (m, 1H), 2.95-2.86 (m, 1H), 1.75-1.67 (m, 2H), 1.66-1.47 (m, 2H)

l) Fumarate Salt Form Fumarate-NF4:

Approx. 50 mg of free base were dissolved in 2.5 mL 2-Propanol at RT and approx. 13 mg Fumaric acid were added to the solution. No spontaneous precipitation was observed. The vial was open placed in a fume hood to evaporate the solvent. A glassy residue was obtained. 2-Propanol was added and a suspension was obtained. It was solid-/liquid separated by centrifugation using a PE centrifuge vial.

m) Fumarate Salt Form Fumarate-NF5 (Mixture with Fumarate-NF1):

The clear mother liquor of a Fumarate salt crystallisation experiment in 2-Propanol with original composition of approx. 20 mg free base, 5 mg Fumaric acid and 1 mL 2-Propanol, was evaporated at RT. A glassy residue and a fraction of white crystals was obtained. The white crystals were extracted for analyses.

$^1$H NMR (500 MHz, DMSO-d6) δ 7.96 (s, 1H), 7.45-7.39 (m, 2H), 7.26-7.22 (m, 2H), 7.19-7.14 (m, 1H), 7.14-7.10 (m, 4H), 6.80 (dd, J=16.7, 10.5 Hz, 1H), 6.62 (s, 2H), 6.09 (dd, J=16.7, 2.4 Hz, 1H), 5.65 (dd, J=10.5, 2.4 Hz, 1H), 5.60-5.53 (m, 2H), 5.20 (t, J=6.4 Hz, 1H), 4.22-4.14 (m, 1H), 3.94-3.85 (m, 1H), 3.58 (dd, J=21.0, 6.4 Hz, 2H), 3.28-3.19 (m, 1H), 2.95-2.86 (m, 1H), 1.75-1.67 (m, 2H), 1.66-1.48 (m, 2H)

n) Mesylate Salt Form Mesylate-NF1:

Approx. 20 mg of free base were dissolved in 0.8 mL Acetone at RT and approx. 3 μL Methane sulfonic acid were added to the solution. No spontaneous precipitation was observed. The vial was open placed in a fume hood to evaporate the solvent. A glassy residue was obtained. To this residue 0.4 mL Ethanol was added and a clear solution was obtained at 50° C. which was cooled down to 5° C. within 16 h. No crystallisation occurred. The vial with the clear solution was placed open in a closed bigger vial with Diethyl ether at the bottom as anti-solvent reservoir for vapour diffusion processes. A white residue was obtained and it was solid-/liquid separated by centrifugation using a PE centrifuge vial.

$^1$H NMR (500 MHz, DMSO-d6) δ 8.30 (s, 1H), 7.47-7.42 (m, 2H), 7.29-7.25 (m, 2H), 7.22-7.18 (m, 1H), 7.18-7.11 (m, 4H), 6.92-6.69 (m, 2H), 6.81 (dd, J=16.7, 10.5 Hz, 1H), 6.10 (dd, J=16.7, 2.4 Hz, 1H), 5.67 (dd, J=10.4, 2.4 Hz, 1H), 4.27-4.19 (m, 1H), 3.97-3.88 (m, 1H), 3.69-3.57 (m, 2H), 3.28-3.19 (m, 1H), 2.92-2.83 (m, 1H), 2.30 (s, 3H), 1.76-1.67 (m, 2H), 1.67-1.46 (m, 2H)

Example 6: Solubility Data of Free Base Forms

Thermodynamic solubility data at 37° C. of free base forms A1 and A2

Approximately 10-20 mg of 1-(4-{[6-Amino-5-(4-phenoxy-phenyl)-pyrimidin-4-ylamino]-methyl}-4-fluoro-piperidin-1-yl)-propenone were weighed into a 4 mL glass vial.

1 mL of FaSSIF medium (pH 6.5) or USP Phosphate buffer pH 7.4 was added and the suspension was shaken for 24 h at 450 rpm at 37° C. After 1 h, 6 h and after 24 h the vials were checked for presence of undissolved compound and the pH was measured. If necessary, the pH was adjusted after 1 h and 6 h. The solid liquid separation was carried out using 1 mL syringe and 0.2 μm syringe filter. Clear filtrate was analysed by HPLC after suitable dilution to measure the amount of API dissolved.

Results from thermodynamic solubility determinations are summarised below.

| Form | Thermodynamic solubility FaSSIF pH 6.5 | Thermodynamic solubility PBS buffer 7.4 |
| --- | --- | --- |
| Free base form A1 | 17 μg/mL | 1 μg/mL |
| Free base form A2 | 10 μg/mL | 2 μg/mL |

Example 7: Mini-Dissolution Data of Novel Salt Forms Vs Parent

Approximately 10-20 mg of 1-(4-{[6-Amino-5-(4-phenoxy-phenyl)-pyrimidin-4-ylamino]-methyl}-4-fluoro-piperidin-1-yl)-propenone were weighed into glass vials. 7 mL of FaSSIF medium (pH 6.5, prewarmed to 37° C.) were added and the suspension was shaken at 450 rpm at 37° C. After 30 min, 60 min and 120 min, 1 mL suspension was withdrawn and filtered through a 0.2 μm syringe filter. Clear filtrate was analysed by HPLC after suitable dilution to measure the amount of API dissolved.

Results from mini dissolution studies are summarised below.

| | Dissolution levels in FaSSIF pH 6.5 (μg/mL) | | | |
| --- | --- | --- | --- | --- |
| Time | Free base form A1 | Free base form A2 | HCl-NF1 | HBr-NF1 |
| 30 min | 16 | 7 | 55 | 23 |
| 60 min | 17 | 8 | 43 | 27 |
| 120 min | 17 | 8 | 46 | 35 |

| Time | Oxalate-NF1 | Fumarate-NF1 |
| --- | --- | --- |
| 30 min | 22 | 14 |
| 60 min | 39 | 18 |
| 120 min | 53 | 27 |

While a number of embodiments of this invention are described herein, it is apparent that the basic examples may be altered to provide other embodiments that utilize the compounds and methods of this invention. Therefore, it will be appreciated that the scope of this invention is to be defined by the previously described embodiments rather than by the specific embodiments that have been represented by way of example.

We claim:
1. A substantially crystalline solid form of compound 1,

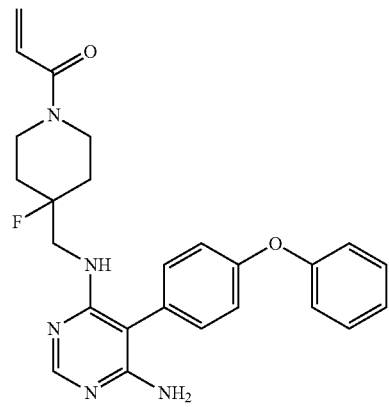

wherein the solid form is a crystalline anhydrous form.

2. A substantially crystalline solid form of compound 1,

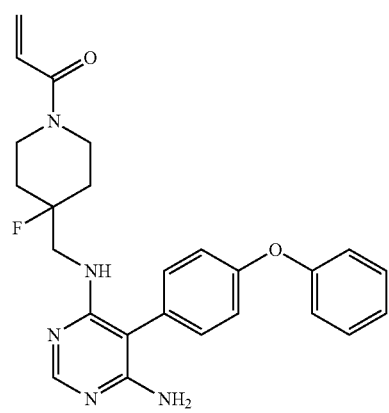

wherein the solid form is a crystalline anhydrous form A2, wherein form A2 is characterized by four or more 2θ XRPD peaks at 7.5±0.2°, 10.8±0.2°, 17.0±0.2°, 17.5±0.2°, 18.7±0.2°, 20.5±0.2°, 21.7±0.2°, 22.3±0.2°, 23.6±0.2°, and 24.0±0.2° degrees.

3. A substantially crystalline solid form of compound 1,

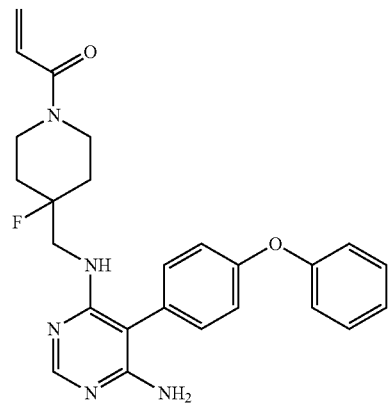

wherein the solid form is a crystalline form A2, having has a space group P-1 with the lattice parameters a=9.5±0.1 Å, b=10.7±0.1 Å, c=12.8±0.1 Å, and α=71.0±0.1°, β=68.99±0.1°, γ=71.9±0.1°.

4. A substantially crystalline solid form of compound 1,

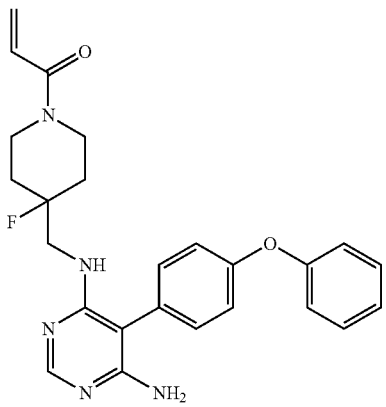

wherein the solid form is A1, having a space group P21/n with the lattice parameters a=12.8±0.1 Å, b=12.9±0.1 Å, c=28.6±0.1 Å, and β=98.0±0.1° with α=γ=90°.

5. A substantially crystalline solid form of compound 1,

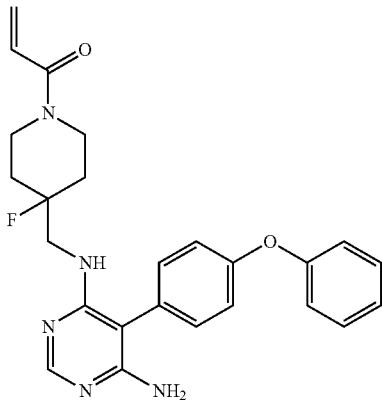

wherein the solid form is a crystalline form A2, wherein form A2 is characterized by a 2θ XRPD spectrum, comprising peaks at 17.0±0.2°, 18.7±0.2°, and 21.7±0.2° degrees.

6. A pharmaceutical composition comprising the solid form of compound 1 of claim 5, and a pharmaceutically acceptable adjuvant, carrier, or vehicle.

7. A method for treating a BTK-mediated disorder in a patient in need thereof, the method comprising:
administering to said patient the solid form of compound 1 of claim 5.

8. A method for producing a medicament for the prophylactic or therapeutic treatment of a BTK-mediated disorder, the method comprising:
formulating the solid form of compound 1 of claim 5, or physiologically acceptable salts thereof.

9. A substantially crystalline solid form of compound 1,

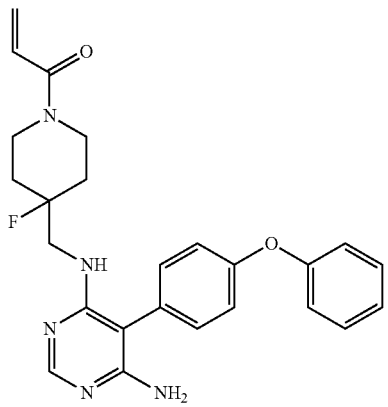

wherein the solid form is A1,
wherein form A1 is characterized by four or more 2θ XRPD peaks at 17.1±0.2°, 17.4±0.2°, 18.8±0.2°, 20.0±0.2°, and 21.1±0.2° degrees.

10. A pharmaceutical composition comprising the solid form of compound 1 of claim 9, a pharmaceutically acceptable adjuvant, carrier, or vehicle.

11. A method for treating a BTK-mediated disorder in a patient in need thereof, the method comprising:
administering to said patient the solid form of compound 1 of claim 9.

12. A method for producing a medicament for the prophylactic or therapeutic treatment of a BTK-mediated disorder, the method comprising: formulating the solid form of compound 1 of claim 9.

13. A pharmaceutically acceptable salt of a substantially crystalline solid form of compound 1,

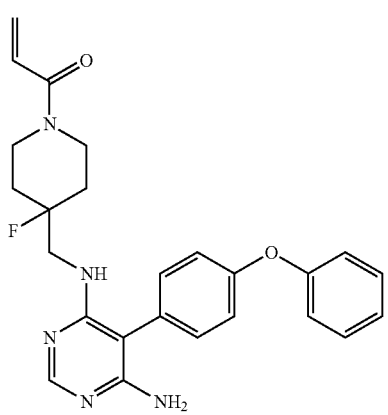

which is selected from the group consisting of HCl salt HCl-NF1 of compound 1, HCl salt HCl-NF2 of compound 1, HCl salt HCl-NF3 of compound 1, HBr salt HBr-NF1 of compound 1, HBr salt HBr-NF2 of compound 1, oxalate salt form oxalate-NF1 of compound 1, maleate salt form maleate-NF1 of compound 1, maleate salt form maleate-NF2 of compound 1, fumarate salt form fumarate-NF1 of compound 1, fumarate salt form fumarate-NF2 of compound 1, fumarate salt form fumarate-NF3 of compound 1, fumarate salt form fumarate-NF4 of compound 1, fumarate salt form fumarate-NF5 of compound 1, and mesylate salt form mesylate-NF1 of compound 1.

14. The pharmaceutically acceptable salt of claim 13, which is HCl-NF1 salt and is characterized by two or more 2θ XRPD peaks at 15.7±0.2°, 19.1±0.2°, 20.3±0.2°, and 20.8±0.2° degrees.

15. The pharmaceutically acceptable salt of claim 13, which is HCl-NF2 salt and is characterized by two or more 2θ XRPD peaks at 7.8±0.2°, 13.0±0.2°, and 15.6±0.2° degrees.

16. The pharmaceutically acceptable salt of claim 13, which is HCl-NF3 salt and is characterized by two or more 2θ XRPD peaks at 14.8±0.2°, 16.8±0.2°, 20.1±0.2°, and 20.4±0.2° degrees.

17. The pharmaceutically acceptable salt of claim 13, which is HBr-NF1 salt and is characterized by two or more 2θ XRPD peaks at 6.9±0.2°, 19.1±0.2°, 20.4±0.2°, 20.8±0.2°, and 21.9±0.2° degrees.

18. The pharmaceutically acceptable salt of claim 13, which is HBr-NF2 salt and is characterized by two or more 2θ XRPD peaks at 4.9±0.2°, 13.2±0.2°, and 20.0±0.2° degrees.

19. The pharmaceutically acceptable salt of claim 13, which is oxalate-NF1 salt and is characterized by two or more 2θ XRPD peaks at 16.2±0.2°, 17.7±0.2°, 18.6±0.2°, 21.1±0.2°, and 21.3±0.2° degrees.

20. The pharmaceutically acceptable salt maleate of claim 13, which is maleate-NF1 salt and is characterized by two or more 2θ XRPD peaks at 18.1±0.2°, 19.1±0.2°, 20.8±0.2°, and 24.8±0.2° degrees.

21. The pharmaceutically acceptable salt of claim 13, which is maleate-NF2 salt and is characterized by two or more 2θ XRPD peaks at 10.8±0.2°, 17.1±0.2°, 19.2±0.2°, and 20.7±0.2° degrees.

22. The pharmaceutically acceptable salt of claim 13, is fumarate-NF1 salt and is characterized by two or more 2θ XRPD peaks at 9.0±0.2°, 17.0±0.2°, 18.4±0.2°, and 22.1±0.2° degrees.

23. The pharmaceutically acceptable salt of claim 13, which is mesylate-NF1 salt and is characterized by two or more 2θ XRPD peaks at 18.7±0.2°, 19.5±0.2°, and 21.1±0.2° degrees.

* * * * *